(12) United States Patent
Marineau et al.

(10) Patent No.: US 12,240,869 B2
(45) Date of Patent: *Mar. 4, 2025

(54) INHIBITORS OF CYCLIN-DEPENDENT KINASE 7 (CDK7)

(71) Applicant: Syros Pharmaceuticals, Inc., Cambridge, MA (US)

(72) Inventors: Jason J. Marineau, Franklin, MA (US); Michael Bradley, Houston, TX (US); Claudio Chuaqui, Arlington, MA (US); Stephane Ciblat, Montreal (CA); Anzhelika Kabro, Lachine (CA)

(73) Assignee: Syros Pharmaceuticals, Inc., Cambridge, MA (US)

( * ) Notice: Subject to any disclaimer, the term of this patent is extended or adjusted under 35 U.S.C. 154(b) by 777 days.

This patent is subject to a terminal disclaimer.

(21) Appl. No.: 17/289,861

(22) PCT Filed: Nov. 1, 2019

(86) PCT No.: PCT/US2019/059542
§ 371 (c)(1),
(2) Date: Apr. 29, 2021

(87) PCT Pub. No.: WO2020/093011
PCT Pub. Date: May 7, 2020

(65) Prior Publication Data
US 2021/0403495 A1 Dec. 30, 2021

Related U.S. Application Data

(60) Provisional application No. 62/927,469, filed on Oct. 29, 2019, provisional application No. 62/915,983, filed on Oct. 16, 2019, provisional application No. 62/877,189, filed on Jul. 22, 2019, provisional application No. 62/754,398, filed on Nov. 1, 2018.

(51) Int. Cl.
| | | |
|---|---|---|
| *C07F 9/6558* | (2006.01) |
| *A61K 9/00* | (2006.01) |
| *A61K 9/20* | (2006.01) |
| *A61K 9/48* | (2006.01) |
| *A61K 31/675* | (2006.01) |
| *A61K 47/26* | (2006.01) |
| *A61K 47/36* | (2006.01) |
| *A61K 47/38* | (2006.01) |
| *A61P 35/00* | (2006.01) |

(52) U.S. Cl.
CPC ........ *C07F 9/65583* (2013.01); *A61K 9/0053* (2013.01); *A61K 9/20* (2013.01); *A61K 9/48* (2013.01); *A61K 31/675* (2013.01); *A61K 47/26* (2013.01); *A61K 47/36* (2013.01); *A61K 47/38* (2013.01); *A61P 35/00* (2018.01); *C07B 2200/05* (2013.01)

(58) Field of Classification Search
CPC .... C07F 9/65583; A61P 35/00; A61K 9/0053; A61K 9/20; A61K 9/48; A61K 31/675; A61K 47/26; A61K 47/36; A61K 47/38; C07B 2200/05
See application file for complete search history.

(56) References Cited

U.S. PATENT DOCUMENTS

| | | |
|---|---|---|
| 6,774,122 B2 | 8/2004 | Evans et al. |
| 7,235,576 B1 | 6/2007 | Riedl et al. |
| 7,351,834 B1 | 4/2008 | Riedl et al. |
| 7,456,160 B2 | 11/2008 | Evans et al. |
| 7,615,562 B2 | 11/2009 | Bollbuck et al. |
| 7,897,623 B2 | 3/2011 | Riedl et al. |
| 7,973,031 B2 | 7/2011 | Griffin et al. |
| 8,114,874 B2 | 2/2012 | Zou et al. |
| 8,124,630 B2 | 2/2012 | Riedl et al. |
| 8,222,244 B2 | 7/2012 | Griffin et al. |
| 8,329,680 B2 | 12/2012 | Evans et al. |
| 8,466,139 B2 | 6/2013 | Evans et al. |
| 8,546,399 B2 | 10/2013 | Bruncko et al. |

(Continued)

FOREIGN PATENT DOCUMENTS

| | | |
|---|---|---|
| CA | 3069829 A1 | 1/2019 |
| JP | 2008526824 A | 2/2009 |

(Continued)

OTHER PUBLICATIONS

Browne et al. "A Chemoproteomic Strategy for Direct and Proteome-Wide Covalent Inhibitor Target-Site Identification," Journal of the American Chemical Society, 2019, 141:191-203.
Gao et al. "Overcoming Resistance to the THZ Series of Covalent Transcriptional CDK Inhibitors," Cell Chemical Biology, 2018, 25:135-142.
Geng et al. "Targeting CDK12-mediated transcription regulation in anaplastic thyroid carcinoma," Biochemical and Biophysical Research Communications, 2019, 520:544-550.
Hu et al., "An Oral and Selective CDK7 Inhibitor Demonstrates Substantial Anti-tumor Effect in Breast and Ovarian Cancer Models," 30th EORTC-NCI-AACR Molecular Targets and Cancer Symposium, Abstract No. 96, 2018.

(Continued)

*Primary Examiner* — Matthew P Coughlin
*Assistant Examiner* — Quincy McKoy
(74) *Attorney, Agent, or Firm* — Leber IP Law; Shelly M. Fujikawa

(57) ABSTRACT

The present invention provides various compositions, including compounds of Formula (I) or (Ia), or a species thereof, and pharmaceutically acceptable salts, solvates (e.g., hydrates), stereoisomer, tautomers, isotopic and other specified forms thereof. Also provided are methods (or uses) and kits involving the compounds or pharmaceutically acceptable compositions containing them for treating or preventing a disease (e.g., a proliferative disease such as cancer) in a subject. Administration of a compound or pharmaceutical composition described herein is expected to inhibit cyclin-dependent kinase 7 (CDK7), and thereby, induce apoptosis in tumor cells in the subject.

27 Claims, 8 Drawing Sheets

Specification includes a Sequence Listing.

(56) References Cited

U.S. PATENT DOCUMENTS

| | | | |
|---|---|---|---|
| 8,618,141 | B2 | 12/2013 | Dumas et al. |
| 8,841,330 | B2 | 9/2014 | Riedl et al. |
| 8,877,933 | B2 | 11/2014 | Grunenberg et al. |
| 9,012,462 | B2 | 4/2015 | Wang et al. |
| 9,029,533 | B2 | 5/2015 | Zou et al. |
| 9,174,982 | B2 | 11/2015 | Bruncko et al. |
| 9,493,470 | B2 | 11/2016 | Murray et al. |
| 9,539,251 | B2 | 1/2017 | Sampath et al. |
| 9,561,228 | B2 | 2/2017 | Haq et al. |
| 9,737,488 | B2 | 8/2017 | Schuckler et al. |
| 10,308,648 | B2 | 6/2019 | Ciblat et al. |
| 10,336,760 | B2 | 7/2019 | Marineau et al. |
| 10,738,067 | B2 * | 8/2020 | Marineau ............ A61K 31/555 |
| 11,311,542 | B2 | 4/2022 | Marineau et al. |
| 2011/0160237 | A1 | 6/2011 | Ali et al. |
| 2013/0017194 | A1 | 1/2013 | Holmes et al. |
| 2014/0031360 | A1 | 1/2014 | Wang et al. |
| 2016/0264552 | A1 | 9/2016 | Ciblat et al. |
| 2016/0264554 | A1 | 9/2016 | Gray et al. |
| 2017/0174692 | A1 | 6/2017 | Marineau et al. |
| 2017/0183355 | A1 | 6/2017 | Sprott et al. |
| 2017/0327496 | A1 | 11/2017 | Ciblat et al. |
| 2019/0276440 | A1 | 9/2019 | Zhao et al. |
| 2019/0330218 | A1 | 10/2019 | Marineau et al. |
| 2019/0337940 | A1 | 11/2019 | Ciblat et al. |
| 2020/0010473 | A1 | 1/2020 | Marineau et al. |
| 2020/0190126 | A1 | 6/2020 | Marineau et al. |
| 2021/0401859 | A1 * | 12/2021 | Hodgson ............ A61K 9/20 |
| 2023/0210852 | A1 * | 7/2023 | Hodgson ............ A61K 31/337 514/247 |

FOREIGN PATENT DOCUMENTS

| | | |
|---|---|---|
| JP | 2006522768 A | 1/2011 |
| JP | 2011523646 A | 7/2012 |
| JP | 2014500277 A | 1/2014 |
| JP | 2017510651 A | 10/2019 |
| JP | 2018515434 A1 | 4/2021 |
| RU | 2461559 C2 | 9/2012 |
| RU | 2014139705 A | 10/2014 |
| WO | WO-2006038001 A1 | 4/2006 |
| WO | WO-2006096564 A1 | 9/2006 |
| WO | 2006125974 A1 | 11/2006 |
| WO | WO-2008137105 A1 | 11/2008 |
| WO | 2011082266 A2 | 7/2011 |
| WO | WO-2012078777 A1 | 6/2012 |
| WO | WO-2015058126 A1 | 4/2015 |
| WO | WO-2015058163 A2 | 4/2015 |
| WO | 2015154038 A1 | 10/2015 |
| WO | WO-2015154039 A2 | 10/2015 |
| WO | WO-2015/195228 A1 | 12/2015 |
| WO | WO-2015188777 A1 | 12/2015 |
| WO | 2016058544 A1 | 4/2016 |
| WO | 2016160617 A2 | 10/2016 |
| WO | WO-2018013867 A1 | 1/2018 |
| WO | WO-2018098473 A1 | 5/2018 |
| WO | WO-2019143719 A1 | 7/2019 |
| WO | WO-2019143730 A1 | 7/2019 |
| WO | WO-2019204781 A1 | 10/2019 |
| WO | WO-2019217757 A1 | 11/2019 |

OTHER PUBLICATIONS

Hu et al., "SY-5609, an Orally Available Selective CDK7 Inhibitor, Demonstrates Broad Anti-tumor Activity In Vivo," American Association for Cancer Research (AACH) Annual Meeting, Abstract No. 4421, 2019.

Iniguez et al. "EWS/FLI Confers Tumor Cell Synthetic Lethality to CDK12 Inhibition in Ewing Sarcoma," Cancer Cell, 2018, 33:202-216.

International Search Report for PCT/US2017/042017 dated Oct. 13, 2017.

International Search Report for PCT/US2019/013845 dated Mar. 14, 2019.

International Search Report for PCT/US2019/013860 dated Mar. 22, 2019.

International Search Report for PCT/US2019/59542 dated Feb. 11, 2020.

Ito et al. "Discovery of 3-Benzyl-1-(trans-4-((5-cyanopyridin-2-yl)amino)cyclohexyl)-1-arylurea Derivatives as Novel and Selective Cyclin-Dependent Kinase 12 (CDK12) Inhibitors," Journal of Medicinal Chemistry, 2018, 61:7710-7728.

Johannes et al. "Structure-Based Design of Selective Noncovalent CDK12 Inhibitors," ChemMedChem, 2018, 13:231-235.

Johannessen et al., "Preclinical Evaluation of PK, PD, and Antitumor Activity of the Oral, Non-covalent, Potent and Highly Selective CDK7 Inhibitor, SY-5609, Provides Rationale for Clinical Development in Multiple Solid Tumor Indications," 31st EORTC-NCI-AACR Molecular Targets and Cancer Symposium, Abstract No. C091, 2019.

Krajewska et al. "CDK12 loss in cancer cells affects DNA damage response genes through premature cleavage and polyadenylation," Nature Communications, 2019, 10(1):1-16.

Olson et al. "Development of a Selective CDK7 Covalent Inhibitor Reveals Predominant Cell-Cycle Phenotype," Cell Chemical Biology, 2019, 26:792-803.

Zhang et al. "Covalent targeting of remote cysteine residues to develop CDK12 and CDK13 inhibitors," Nature Chemical Biology, 2016, 12:876-884.

English Translation of Russian Patent Application No. 2021115458 Search Report dated Apr. 26, 2023, 2 pages.

European Patent Application No. 23177402.7, partial European Search Report dated Feb. 19, 2024, 13 pages.

Singapore Patent Application No. 11202104438V, Search Report and Written Opinion dated Aug. 19, 2022, 10 pages.

\* cited by examiner

| Compound 100 | CDK7 K$_D$ (nM) = 0.057 | | Comparator 1 | CDK7 K$_D$ (nM) = 0.18 | |
|---|---|---|---|---|---|
| | CDK12 K$_i$ (nM) 230 | (K$_i$/K$_{D\,CDK7}$) 4100 | | CDK12 K$_i$ (nM) 51 | (K$_i$/K$_{D\,CDK7}$) 280 |
| | CDK2 K$_i$ (nM) 1500 | (K$_i$/K$_{D\,CDK7}$) 26000 | | CDK2 K$_i$ (nM) 210 | (K$_i$/K$_{D\,CDK7}$) 1100 |
| | CDK9 K$_i$ (nM) 800 | (K$_i$/K$_{D\,CDK7}$) 14000 | | CDK9 K$_i$ (nM) 140 | (K$_i$/K$_{D\,CDK7}$) 790 |
| Compound 101 | CDK7 K$_D$ (nM) = 0.065 | | Comparator 2 | CDK7 K$_D$ (nM) = 0.45 | |
| | CDK12 K$_i$ (nM) 870 | (K$_i$/K$_{D\,CDK7}$) 13000 | | CDK12 K$_i$ (nM) 140 | (K$_i$/K$_{D\,CDK7}$) 320 |
| | CDK2 K$_i$ (nM) 2600 | (K$_i$/K$_{D\,CDK7}$) 40000 | | CDK2 K$_i$ (nM) 810 | (K$_i$/K$_{D\,CDK7}$) 1800 |
| | CDK9 K$_i$ (nM) 960 | (K$_i$/K$_{D\,CDK7}$) 15000 | | CDK9 K$_i$ (nM) 130 | (K$_i$/K$_{D\,CDK7}$) 280 |
| Compound 102 | CDK7 K$_D$ (nM) = 0.059 | | Comparator 3 | CDK7 K$_D$ (nM) = 0.21 | |
| | CDK12 K$_i$ (nM) 78 | (K$_i$/K$_{D\,CDK7}$) 1300 | | CDK12 K$_i$ (nM) 18 | (K$_i$/K$_{D\,CDK7}$) 89 |
| | CDK2 K$_i$ (nM) 390 | (K$_i$/K$_{D\,CDK7}$) 6800 | | CDK2 K$_i$ (nM) 26 | (K$_i$/K$_{D\,CDK7}$) 130 |
| | CDK9 K$_i$ (nM) 290 | (K$_i$/K$_{D\,CDK7}$) 4900 | | CDK9 K$_i$ (nM) 20 | (K$_i$/K$_{D\,CDK7}$) 99 |
| | | | Comparator 4 | CDK7 K$_D$ (nM) = 0.34 | |
| | | | | CDK12 K$_i$ (nM) 48 | (K$_i$/K$_{D\,CDK7}$) 140 |
| | | | | CDK2 K$_i$ (nM) 64 | (K$_i$/K$_{D\,CDK7}$) 190 |
| | | | | CDK9 K$_i$ (nM) 36 | (K$_i$/K$_{D\,CDK7}$) 100 |

FIG. 1

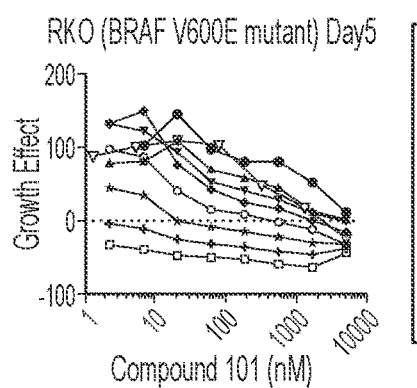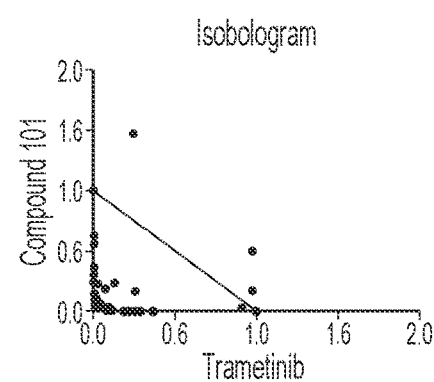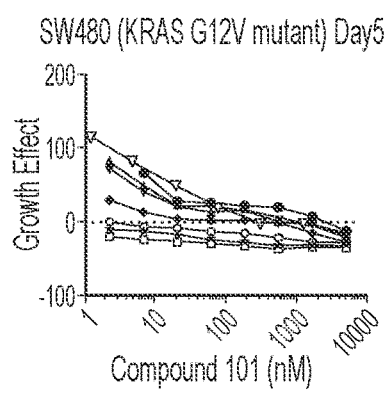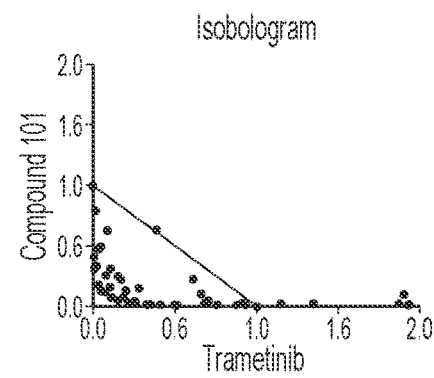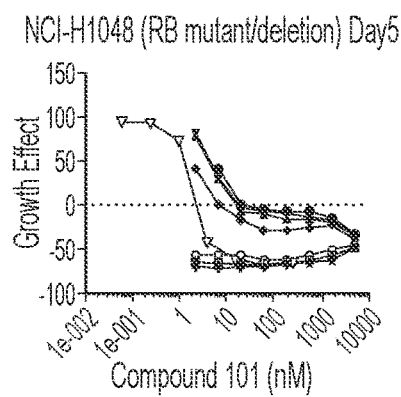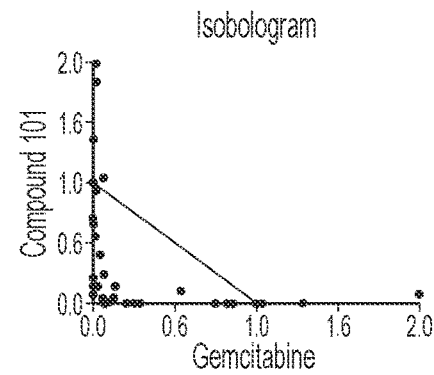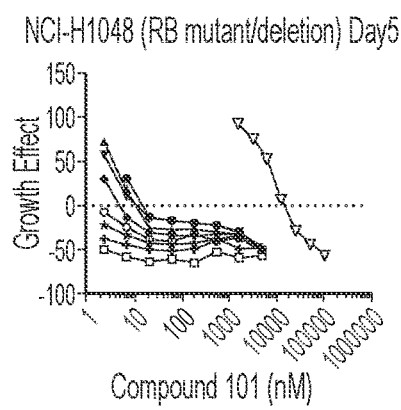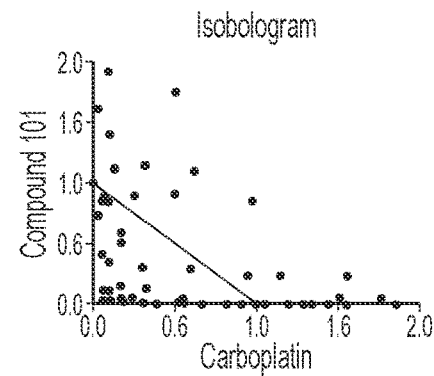
FIG. 5 (cont.)

| PDX model | End of Treatment Day 21 | | Post-treatment Day 42 | | RB pathway genetics |
| --- | --- | --- | --- | --- | --- |
| | % TGI | % Regression | % TGI | % Regression | |
| OV15398 | >100 | 80 | >100 | 98 | RB1 (CN=1, p.Q637*) |
| LU5180 | >100 | 72 | >100 | 93 | CDKN2A (CN=1) |
| LU5178 | >100 | 64 | >100 | 73 | RB1 (CN=0) |
| BR5010 | >100 | 55 | >100 | 27 | CCNE1 (CN=21) |
| LU5210 | 82 | 0 | >100 | 8 | RB1 (p.L343SfsTer3) |
| BR1458 | 90 | 0 | 95 | 0 | CDKN2A (CN=0) / RB1 (CN=1, p.Y155C) |
| BR5399 | 82 | 0 | 95 | 0 | RB1 (CN=1) |
| LU5192 | 94 | 0 | 69 | 0 | None |
| BR10014 | 91 | 0 | 67 | 0 | None |
| OV5392 | 92 | 0 | 64 | 0 | None |
| OV15631 | 70 | 0 | 71 | 0 | None |
| LU5173 | 74 | 0 | 33 | 0 | None |

FIG. 7

INHIBITORS OF CYCLIN-DEPENDENT KINASE 7 (CDK7)

CROSS-REFERENCE TO RELATED APPLICATIONS

This application is a U.S. national phase application filed under 35 U.S.C. § 371 of International application no. PCT/US2019/059542, filed Nov. 1, 2019, which claims the benefit of the filing date of U.S. provisional application No. 62/754,398, filed Nov. 1, 2018; U.S. provisional application No. 62/877,189, filed Jul. 22, 2019; U.S. provisional application No. 62/915,983, filed Oct. 16, 2019, and U.S. provisional application No. 62/927,469, filed Oct. 29, 2019. The content of each of these prior applications is hereby incorporated by reference herein in its entirety.

SEQUENCE LISTING

The instant application contains a Sequence Listing which has been submitted electronically in ASCII format and is hereby incorporated by reference in its entirety. The ASCII copy, created on Jan. 7, 2020, is named SL.txt and is 976 bytes in size.

BACKGROUND OF THE INVENTION

Members of the cyclin-dependent kinase (CDK) family are believed to play important roles in regulating cellular proliferation. The predominant target of the inhibitors described herein, CDK7, exists as a heterotrimeric complex in the cytosol and also forms the kinase core of the RNA polymerase (RNAP) II general transcription factor complex in the nucleus. Within that complex, CDK7 phosphorylates the C-terminal domain (CTD) of RNAP II, which is a requisite step in initiating gene transcription.

SUMMARY OF THE INVENTION

The present invention provides selective CDK7 inhibitors that are chemical compounds having a formula disclosed herein (e.g., Formula (I) or a subgenus (e.g., Formula (Ia)) or species thereof) and, in various embodiments, pharmaceutically acceptable salts, solvates (e.g., hydrates), stereoisomers or mixtures of stereoisomers (e.g., racemic mixtures), tautomers, and isotopic forms (e.g., deuterated forms) thereof, wherein various component parts of the compounds (e.g., elements $R^1$, $R^2$, $R^3$, and $R^4$ of Formula (I) and subvariables thereof) are as described herein. Compounds of the invention demonstrate surprising and unexpected superiority over other, comparator compounds in terms of selectivity for CDK7 over each of CDK2, CDK9 and CDK12; affinity for CDK7/cyclin H complexes; and anti-proliferative activity in cell line models, including a cell line model of triple-negative breast cancer. In addition, compounds of the invention demonstrate good bioavailability in a rat model. Accordingly, in a first embodiment, the present invention provides a compound of Formula (I) or (Ia) or species thereof, in a second embodiment, the invention provides a salt thereof, in a third embodiment, the invention provides a solvate thereof; in a fourth embodiment, the invention provides a stereoisomer thereof of a mixture of stereoisomers (e.g., a racemic mixture); in a fifth embodiment, the invention provides a tautomer thereof, and in a sixth embodiment, the invention provides an isotopic form thereof. We may refer to these forms of a compound (i.e., to the salt form, a solvate, stereoisomer, tautomer, or isotopic form) as "specified forms" of the compound. Also within the meaning of "specified form" are forms of a compound that manifest a combination of the attributes, features, or properties of a salt, solvate, stereoisomer, tautomer, or isotopic form. For example, the methods and uses of the invention can be carried out with a salt that has been solvated (e.g., a hydrated) or a salt of a stereoisomer, tautomer, or isotopic form of a compound of Formula I, I(a), or a species thereof; with a solvate (e.g., hydrate) containing a salt, stereoisomer, tautomer, or isotopic form of a compound of Formula I, I(a), or a species thereof, with a stereoisomer of a compound of Formula I, or a species thereof, that is in the form of a salt or solvate (e.g., hydrate) or is a tautomer or isotopic form of a compound of Formula I, or a species thereof, with a tautomer of a compound of Formula I, I(a), or a species thereof that is in the form of a salt or solvate (e.g., hydrate) or that is a stereoisomer or isotopic form of a compound of Formula I, I(a), or a species thereof; or with an isotopic form of a compound of Formula I, I(a), or a species thereof that is a salt, solvate (e.g., hydrate), stereoisomer, or tautomer of a compound of Formula I, I(a), or a species thereof. Any of these specified forms can be pharmaceutically acceptable and/or contained within a pharmaceutically acceptable composition (e.g., formulated for oral administration). For example, a salt of a compound can be solvated; a stereoisomer can be solvated; a tautomer can be in a salt form and/or include isotopes; etc. Thus, the invention encompasses, as a specified form, salts of the compound per se as well as salts of the stereoisomer, tautomeric, and isotopic forms of the compound. Similarly, and in case of doubt, either a given compound or a specified form thereof can be solvated or made as an isotopic form. For example, the invention encompasses, as specified forms, solvates of the compound per se as well as solvates of a salt, stereoisomer, tautomer, or isotopic form thereof, the invention encompasses isotopic forms of the compound per se as well as isotopic forms of the salt, solvate, stereoisomer, or tautomer thereof. These compositions (e.g., salts of a compound, stereoisomer, tautomer, or isotopic form; solvates of a compound, a stereoisomer thereof, tautomer, or isotopic form; isotopic forms of a salt, solvate, stereoisomer, or isomeric form of a compound; and so forth) constitute compositions of the invention useful as described herein. Accordingly, a pharmaceutical composition of the invention, including any of those formulated as described further below (e.g., for oral administration), can include a compound described herein or any one or more of the specified forms thereof. In one embodiment, the invention features a compound of structural Formula (I):

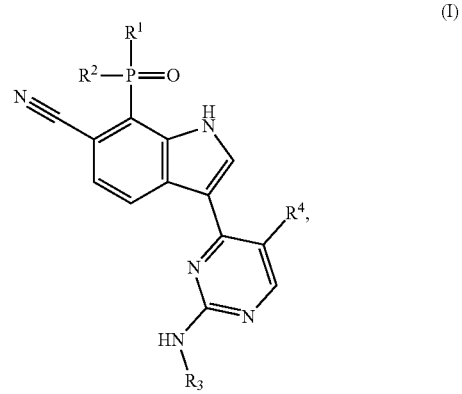

or a pharmaceutically acceptable salt, solvate, stereoisomer or mixture of stereoisomers, tautomer, or isotopic form thereof, wherein $R^1$ is methyl or ethyl; $R^2$ is methyl or ethyl; $R^3$ is 5-methylpiperidin-3-yl, 5,5-dimethylpiperidin-3-yl, 6-methylpiperidin-3-yl, or 6,6-dimethylpiperidin-3-yl, wherein one or more hydrogen atoms in $R^3$ is optionally replaced by deuterium; and $R^4$ is —$CF_3$ or chloro. More specifically, in a compound of Formula (I) or in the pharmaceutically acceptable salt, solvate, stereoisomer or mixture of stereoisomers, tautomer, isotopic form, or other specified form thereof (i) $R^1$ is methyl and $R^2$ is methyl or (ii) $R^1$ is methyl and $R^2$ is ethyl. In other embodiments, $R^1$ is ethyl and $R^2$ is ethyl. In some aspects of any one of these embodiments, $R^4$ is —$CF_3$. In other aspects of any one of these embodiments, $R^4$ is chloro. In various aspects of any of the preceding embodiments, $R^3$ is 5-methylpiperidin-3-yl, $R^3$ is 5,5-dimethylpiperidin-3-yl, $R^3$ is 6-methylpiperidin-3-yl, or $R^3$ is 6,6-dimethylpiperidin-3-yl, wherein one or more hydrogen atoms in $R^3$ is optionally replaced by deuterium. A compound of Formula (I) can have structural Formula (Ia):

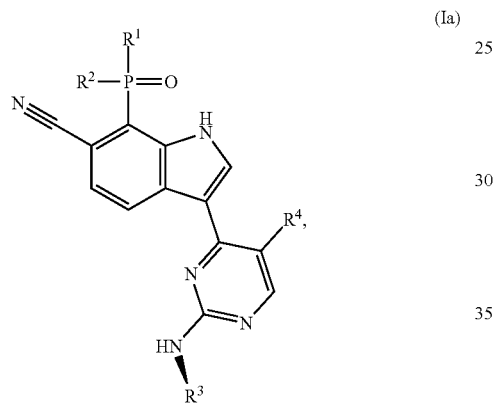

(Ia)

and the invention encompasses pharmaceutically acceptable salts, solvates (e.g., hydrates), tautomers, isotopic forms, or other specified forms of a compound of Formula (Ia), wherein $R^3$ is

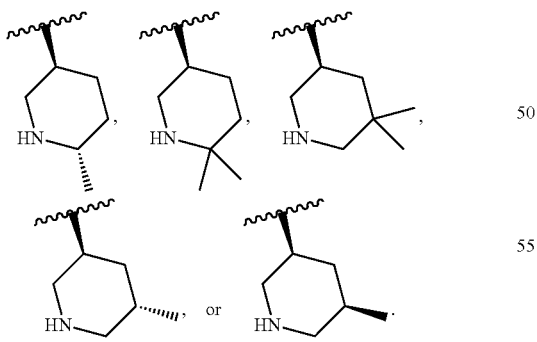

More specifically, in a compound of Formula (Ia) or a pharmaceutically acceptable salt, solvate, tautomer, isotopic form, or other specified form thereof (i) $R^1$ is methyl and $R^2$ is methyl or (ii) $R^1$ is methyl and $R^2$ is ethyl. In other embodiments, $R^1$ is ethyl and $R^2$ is ethyl. In some embodiments, in a compound of Formula (Ia) or a specified form thereof, $R^4$ is —$CF_3$. In other embodiments, in a compound of Formula (Ia) or a specified form thereof, $R^4$ is chloro. In some embodiments, a compound of Formula (I) or (Ia) is:

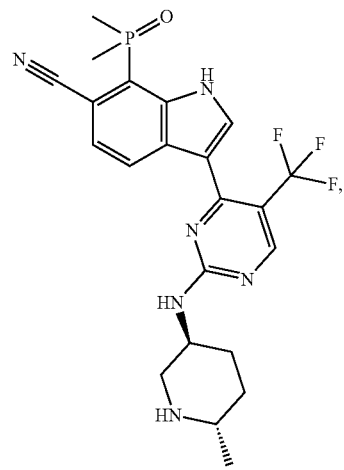

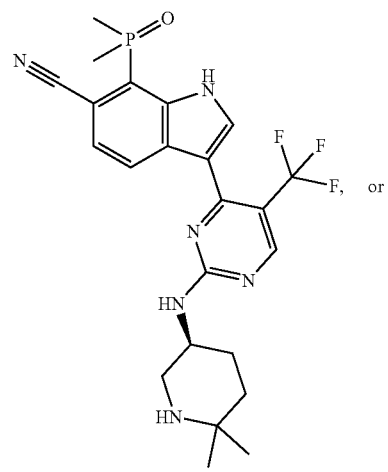

, or

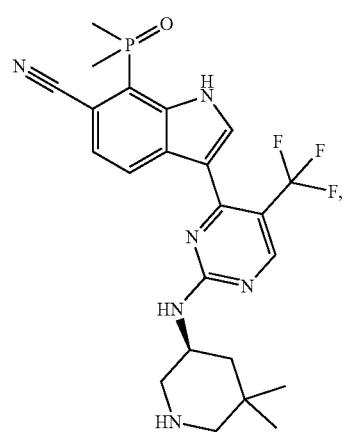

and the invention encompasses pharmaceutically acceptable salts, solvates (e.g., hydrates), tautomers, isotopic forms or other specified forms of any one of the three foregoing compounds. In one embodiment, the compound is

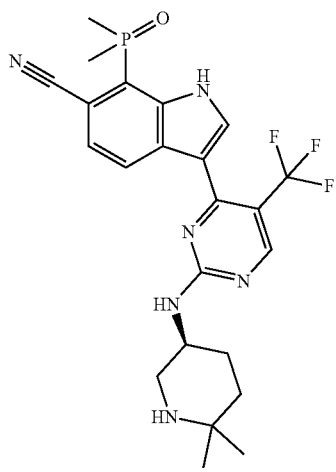

or a pharmaceutically acceptable salt thereof. The invention also encompasses solvates (e.g., hydrates), tautomers, isotopic forms or other specified forms of the foregoing compound. In isotopic forms, one or more hydrogen atoms in $R^3$ is replaced with deuterium. In other embodiments, none of the hydrogen atoms of a compound (e.g., none of the hydrogen atoms in $R^3$) are replaced with deuterium. In other embodiments, the invention features a solvate (e.g., a hydrate) of a compound of Formula (I), (Ia), or a species thereof, with the elements $R^1$, $R^2$, $R^3$, and $R^4$ as described herein. In other embodiments, the invention features a solvate (e.g., a hydrate) of a salt of a compound of Formula (I), (Ia), or a species thereof; a solvate (e.g., a hydrate) of a tautomer of a compound of Formula (I), (Ia), or a species thereof; and a solvate (e.g., a hydrate) of an isomeric form of a compound of Formula (I), (Ia), or a species thereof. The solvate, in any of these embodiments, can be pharmaceutically acceptable and incorporated within a pharmaceutical composition, including any of those formulated as described below (e.g., for oral administration).

In another aspect, the invention features a pharmaceutical composition, which we may also refer to as a pharmaceutical formulation, including a compound as described above (i.e., a compound of Formula (I), (Ia), a species thereof or a specified form thereof (e.g., a pharmaceutically acceptable salt), and a pharmaceutically acceptable carrier. Pharmaceutical compositions of the invention can be formulated for oral administration and/or formulated in unit dosage form (including, e.g., a compound of Formula (I), (Ia), a species thereof, or a salt thereof).

In another aspect, the invention features methods or "use" of a pharmaceutical composition described herein in treating or preventing a disease, wherein the disease is a proliferative disease, inflammatory disease, autoinflammatory disease, autoimmune disease, or infectious disease (each encompassing the specific diseases described herein; see, e.g., the definitions provided herein) in a subject in need thereof. Methods of treatment may include a step of administering a pharmaceutical composition and "use" of the present compositions may be in the preparation of a medicament. In one embodiment, the disease is a proliferative disease (e.g., a cancer, benign neoplasm, or pathologic angiogenesis). For example, the cancer can be a blood cancer (e.g., a leukemia (e.g., AML) or lymphoma). In other embodiments, the cancer is characterized by the presence of a solid tumor (in, e.g., the breast (e.g., a TNBC, HR+, or other type of breast cancer described herein), GI tract (e.g., a CRC), lung (e.g., NSCLC or other type of lung cancer described herein), pancreas, or prostate). In other embodiments, the cancer is a fallopian tube cancer; an ovarian cancer (e.g., a high grade serous ovarian cancer, epithelial ovarian cancer, or clear cell ovarian cancer); a cancer of the central nervous system (e.g., a glioma); a melanoma. or Ewing's sarcoma. In other embodiments, the cancer is a pancreatic cancer; a primary peritoneal cancer; prostate cancer; retinoblastoma; or a squamous cell cancer of the head or neck. In one embodiment, the various methods and uses described herein (e.g., in treating or preventing a proliferative disease, including but not limited to those just described, an inflammatory disease, autoinflammatory disease, autoimmune disease, or infectious disease) are applied to a subject who has been determined to have one or more of the following (as determined in, for example, a biological sample of disease cells obtained from the subject): a high grade cancer (e.g., high grade serous ovarian cancer (HGSOC) or breast cancer); a cellular phenotype in which a steroid receptor is present and/or overexpressed or otherwise aberrant; a triple-negative breast cancer; and/or resistance to a previously administered chemotherapeutic agent (e.g., a Bcl-2 inhibitor such as venetoclax, a BET inhibitor, a CDK4/6 inhibitor such as palbociclib or ribociclib, a CDK9 inhibitor such as alvocidib, a FLT3 inhibitor, a MEK inhibitor such as trametinib, cobimetinib, or binimetinib (useful in combination with a compound of Formula (I), (Ia), a species thereof or specified form thereof in treating melanoma), a PARP inhibitor, such as olaparib or niraparib, a PI3K inhibitor, such as alpelisib, apitolisib (GDC-0980), idelalisib, copanlisib, duvelisib, pictilisib, or capecitabine (useful in combination with a compound of Formula (I), (Ia), a species thereof or specified form thereof in treating, e.g., HR+ breast cancer, TNBC, lymphoma (e.g., follicular lymphoma or non-Hodgkin lymphoma), or leukemia (e.g., CLL), an inhibitor of the PI3K/AKT/mTOR pathway (e.g., gedatolisib), a platinum-based therapeutic agent such as cisplatin, oxaliplatin, nedaplatin, carboplatin, phenanthriplatin, picoplatin, satraplatin (JM216), or triplatin tetranitrate (useful in combination with a compound of Formula (I), (Ia), a species thereof or specified form thereof in treating, e.g., a lung cancer such as SCLC or a GI tract cancer such as CRC), a SERM, such as tamoxifen, raloxifene, or toremifene, a steroid receptor degrading agent (e.g., a SERD, such as fulvestrant), or an agent that inhibits the production of estrogen (e.g., an aromatase inhibitor such as anastrozole (available as Arimidex®), exemestane (available as Aromasin®), and letrozole (available as Femara®). Combination therapies including one or more of these agents (e.g., for a total of two or three administered agents) are also within the scope of the invention and are discussed further herein. For example, in one embodiment, the methods encompass the use of or administration of a compound of Formula (I), (Ia), a species thereof or a specified form thereof, in combination with a SERD, such as fulvestrant, or an aromatase inhibitor such as letrozole, to treat a cancer (e.g., a breast cancer (e.g., an HR+/ER+ breast cancer)) resistant to treatment with a CDK4/6 inhibitor such as palbociclib or ribociclib. In one embodiment, the methods encompass the use of or administration of a compound of Formula (I), (Ia), a species thereof or a specified form thereof, in combination with a MEK inhibitor, such as trametinib, which can be used in further combination with dabrafenib, vemurafenib, or encorafenib.

In another aspect, the invention features kits comprising a pharmaceutical composition or formulation described herein and instructions for use, and, optionally, a "second" agent selected from an anti-proliferative agent, an anti-cancer agent, an immunosuppressant agent, and a pain-relieving agent, including any one or more of those specifically disclosed below). The kits can comprise a container with a compound described herein or a specified form thereof (e.g., a pharmaceutically acceptable salt, solvate, stereoisomer, tautomer, or isotopic form thereof), or a composition (e.g., a pharmaceutically acceptable composition or formulation, as described herein) comprising the compound, salt, solvate, stereoisomer, tautomer or isotopic form thereof. In any embodiment of the kit, instructions for use can be included, and that use can be in treating a disease described herein (e.g., a blood cancer, a cancer characterized by the presence of a solid tumor (in, e.g., the breast, GI tract (e.g., a CRC), lung (e.g., NSCLC), pancreas, or prostate), or Ewing's sarcoma.

The pharmaceutically acceptable compositions of the invention include a composition of the invention (e.g., a compound described herein or a specified form thereof (e.g., a pharmaceutically acceptable salt, solvate (e.g., hydrate), stereoisomer, tautomer, or isotopic form thereof (or another specified form, such as a solvate of a salt of a compound of Formula (I))) and a pharmaceutically acceptable carrier. In certain embodiments, the pharmaceutical compositions include a therapeutically or prophylactically effective amount of a compound of Formula (I) or a subgenus (e.g., Formula (Ia)) or species thereof, or a specified form thereof (e.g., a pharmaceutically acceptable salt, solvate, stereoisomer, tautomer, isotopic form, or other specified form thereof). The pharmaceutical composition may be useful in treating and/or preventing a proliferative or infectious disease, as described further 0 below. The present invention also provides methods of making and using the compounds and other compositions described herein (e.g., any one of the specified forms or pharmaceutical compositions containing a compound of the invention or a specified form thereof) as therapeutics for the prevention and/or treatment of diseases associated with overexpression and/or aberrant activity of CDK7. Amenable diseases include proliferative diseases (e.g., cancers (e.g., a breast cancer, a leukemia or other blood cancer, melanoma, multiple myeloma (MM), ovarian cancer, a cancer of the GI tract (e.g., a CRC) or lung (e.g., NSCLC), pancreatic cancer, prostate cancer, or Ewing's sarcoma), benign neoplasms, and pathologic angiogenesis), inflammatory diseases, autoinflammatory diseases, autoimmune diseases, and infectious diseases, as described herein (see, e.g., the definitions).

BRIEF DESCRIPTION OF THE DRAWINGS

FIG. 1 is a table depicting the inhibitory and dissociation constants and selectivity of the indicated compounds (three compounds of the invention and four comparators) against CDK2, CDK7, CDK9, and CDK12.

FIG. 7 is a Table summarizing the TGI values and genetic status of the 12 PDX models studied as described in Example 12. Models in the table are sorted based on highest to lowest response at end of study. BID, CNV, RB, SCLC, and TNBC are as defined for FIG. 6 and elsewhere herein. In case of doubt, CCNE1=cyclin E1; CDKN2A=cyclin-dependent kinase inhibitor 2A, EoS=end of study, EoT=end of treatment, HGSOC=high-grade serous ovarian cancer, OVA=ovarian cancer, and TGI=tumor growth inhibition. For the LU5210 model, tissue was not available for confirmation of RB pathway genetics.

DETAILED DESCRIPTION

Figure 2:
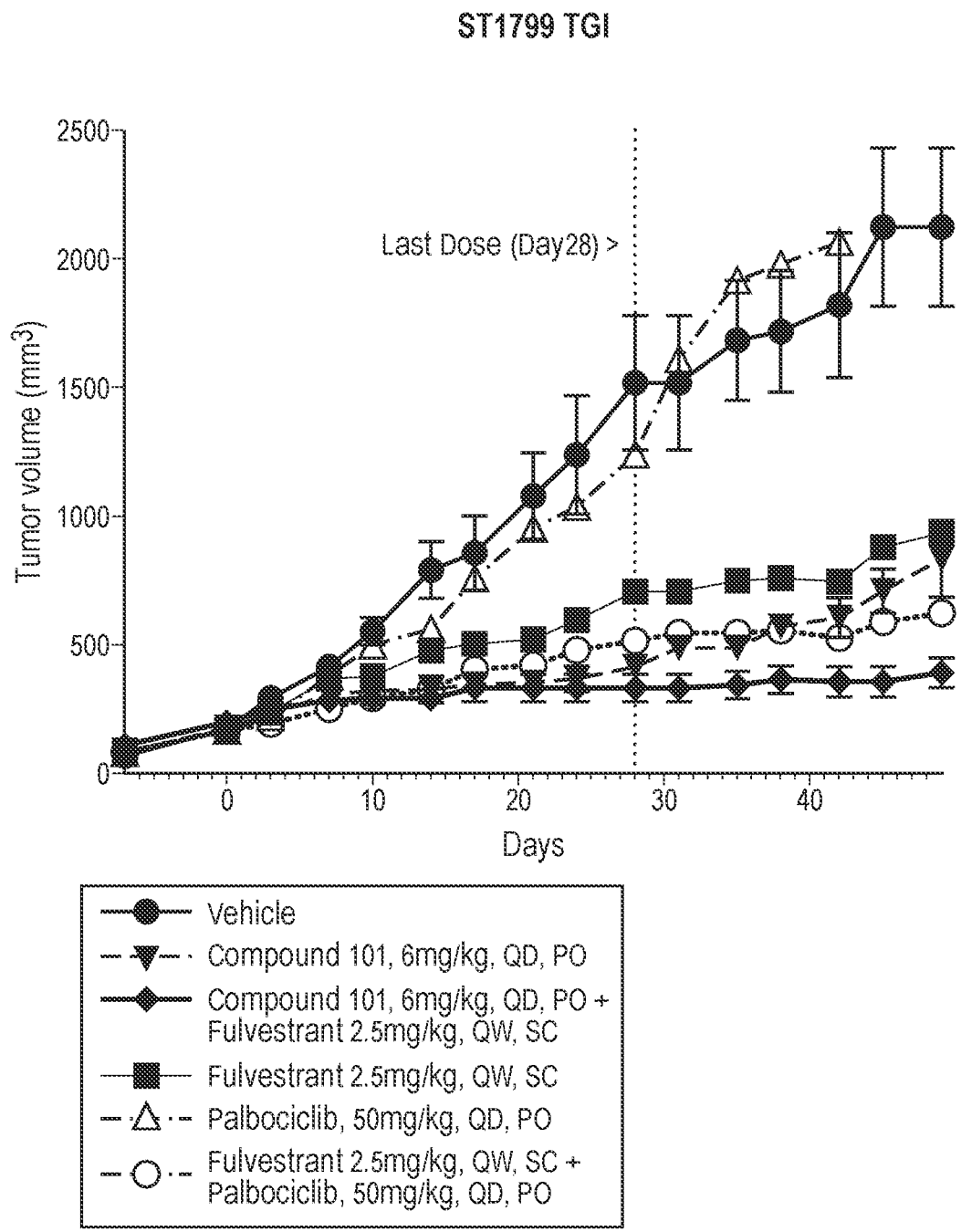
FIG. 2 is a line graph depicting changes in tumor volume (mm$^3$) over time (days) in the palbociclib-resistant HR+BC PDX model ST1799 (as described further in the Examples below).

The following definitions apply to the compositions, methods, and uses described herein unless the context clearly indicates otherwise, and it is to be understood that the claims may be amended to include language within a definition if needed or desired. Moreover, the definitions apply to linguistic and grammatical variants of the defined terms (e.g., the singular and plural forms of a term), and some linguistic variants are particularly mentioned below (e.g., "administration" and "administering" and "biologically active" and "biological activity"). The chemical elements are identified in accordance with the Periodic Table of the Elements, CAS version, Handbook of Chemistry and Physics, 75$^{th}$ Ed. Additionally, general principles of organic chemistry are well established and one of ordinary skill in the art can consult, if desired, *Organic Chemistry* by Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The term "about," when used in reference to a value, signifies any value or range of values that is plus-or-minus 10% of the stated value (e.g., within plus-or-minus 1%, 2%, 3%, 4%, 5%, 6%, 7%, 8%, 9% or 10% of the stated value). For example, a dose of about 10 mg means any dose as low as 10% less than 10 mg (9 mg), any dose as high as 10% more than 10 mg (11 mg), and any dose or dosage range therebetween (e.g., 9-11 mg; 9.1-10.9 mg; 9.2-10.8 mg; and so on). Where a stated value cannot be exceeded (e.g., 100%), "about" signifies any value or range of values that is up to and including 10% less than the stated value (e.g., a purity of about 100% means 90%-100% pure (e.g., 95%-100% pure, 96%-100% pure, 97%-100% pure etc . . . )). In the event an instrument or technique measuring a value has a margin of error greater than 10%, a given value will be about the same as a stated value when they are both within the margin of error for that instrument or technique.

The term "administration" and variants thereof, such as "administering," refer to the administration of a compound described herein (e.g., a compound of Formula (I), (Ia), a species thereof or a specified form thereof (e.g., a pharmaceutically acceptable salt thereof), or one or more additional/second agent(s)), or a composition containing the compound to a subject (e.g., a human patient) or system (e.g., a cell- or tissue-based system that is maintained ex vivo); as a result of the administration, the compound or composition containing the compound is introduced to the subject or system. In addition to compositions of the invention and second agents useful in combination therapies, items used as positive controls, negative controls, and placebos, any of which can also be a compound, can also be "administered." One of ordinary skill in the art will be aware of a variety of routes that can, in appropriate circumstances, be utilized for administration to a subject or system. For example, the route of administration can be oral (i.e., by swallowing a pharmaceutical composition) or may be parenteral. More specifically, the route of administration can be bronchial (e.g., by bronchial instillation), by mouth (i.e., oral), dermal (which may be or comprise topical application to the dermis or intradermal, interdermal, or transdermal administration), intragastric or enteral (i.e., directly to the stomach or intestine, respectively), intramedullary, intramuscular, intranasal, intraperitoneal, intrathecal, intratumoral, intravenous (or intra-arterial), intraventricular, by application to or injection into a specific organ (e.g., intrahepatic), mucosal (e.g., buccal, rectal, sublingual, or vaginal), subcutaneous, tracheal (e.g., by intratracheal instillation), or ocular (e.g., topical, subconjunctival, or intravitreal). Administration can involve intermittent dosing (i.e., doses separated by various times) and/or periodic dosing (i.e., doses separated by a common period of time (e.g., every so many hours, daily (e.g., once daily oral dosing), weekly, twice per week, etc.)). In other embodiments, administration may involve continuous dosing (e.g., perfusion) for a selected time (e.g., about 1-2 hours).

The term "angiogenesis" refers to the formation and growth of new blood vessels. Normal angiogenesis occurs in healthy subjects during development and in the context of wound healing. However, patients suffering from many different disease states, including cancer, diabetes (particularly the progression to blindness associated therewith), age-related macular degeneration, rheumatoid arthritis, and psoriasis, experience excessive and detrimental angiogenesis. Angiogenesis is detrimental when, e.g., it produces blood vessels that support diseased cells (e.g., tumor cells), destroy normal tissues (e.g., tissue within the eye), or facilitate tumor metastases. We may refer to angiogenesis that accompanies and/or facilitates a disease state as "pathologic angiogenesis."

Two events, two entities, or an event and an entity are "associated" with one another if one or more features of the first (e.g., its presence, level and/or form) are correlated with a feature of the second. For example, a first entity (e.g., an enzyme (e.g., CDK7)), gene expression profile, genetic signature (i.e., a single or combined group of genes in a cell with a uniquely characteristic pattern of gene expression), metabolite, or event (e.g., myeloid infiltration)) is associated with an event (e.g., the onset or progression of a particular disease), if its presence, level and/or form correlates with the incidence of, severity of, and/or susceptibility to the disease (e.g., a cancer disclosed herein). Associations are typically assessed across a relevant population. Two or more entities are physically "associated" with one another if they interact, directly or indirectly, so that they are and/or remain in physical proximity with one another in a given circumstance (e.g., within a cell maintained under physiological conditions (e.g., within cell culture) or within a pharmaceutical composition). Entities that are physically associated with one another can be covalently linked to one another or non-covalently associated by, for example, hydrogen bonds, van der Waals forces, hydrophobic interactions, magnetism, or combinations thereof. A compound of Formula (I), (Ia), a species thereof, or a specified form thereof (e.g., a pharmaceutically acceptable salt) can be non-covalently associated with CDK7.

The term "autoimmune disease" refers to a disease arising from an inappropriate immune response against substances and tissues normally present in the body. Stated more simply, a subject's immune system mistakes some part of the body as a pathogen and attacks its own cells. The attack may be restricted to certain organs (e.g., in autoimmune thyroiditis) or may involve a particular tissue in different places (e.g., Goodpasture's disease affects the basement membrane in both the lung and kidney). Autoimmune diseases include, but are not limited to, ANCA-associated vasculitis (e.g., Wegener's granulomatosis, microscopic polyangiitis), ankylosing spondylitis, anti-phospholipid antibody syndrome, autoimmune thyroiditis, cardiomyopathy, Crohn's disease, dermatomyositis or polymyositis, glomerulonephritis, Goodpasture's disease, Guillain-Barre disease, Hashimoto's thyroiditis, lyme arthritis, lymphadenitis, necrotizing vasculitis, peri-arteritis nodosa, psoriasis, pemphigus vulgaris, psoriatic arthritis, Reiter's syndrome, rheumatoid arthritis, scleroderma, Sjogren's syndrome, systemic lupus erythematosus (SLE), systemic sclerosis, ulcerative colitis, and uveitis. Patients having some autoimmune diseases also experience significant inflammation (e.g., rheumatoid arthritis and SLE) and, so, some diseases can be properly referred to as either an autoimmune disease or an inflammatory disease.

An "autoinflammatory disease," which may also be referred to as "periodic fever syndrome," refers to a disease characterized by recurrent (episodic) fevers and evidence of systemic inflammation on blood testing (see, e.g., Ciccarelli et al., Curr. Med. Chem. 21(3):261-269, 2013). The episodes of inflammation can be intense and accompanied by rash or joint swelling, and patients are at risk of amyloidosis, a potentially fatal buildup of a blood protein in vital organs. These diseases are distinct from autoimmune disease and do not involve auto-reactive T-lymphocytes or auto-antibodies. They include, but are not limited to, Behcet's disease, Blau's Syndrome, chronic recurrent multifocal osteomyelitis (CRMO) and synovitis acne pustulosis hyperostosis osteitis (SAPHO) syndrome, cryopyrin-associated periodic syndromes (CAPS), deficiency of the interleukin-1 receptor antagonist (DIRA), familial Mediterranean fever (FMF), NLRP12-associated autoinflammatory disorders, neonatal onset multisystem inflammatory disease (NOMID), Majeed Syndrome, periodic fever associated with mevalonate kinase deficiency (hyperimmunoglobulin D Syndrome), periodic fever, aphthous stomatitis, pharyngitis and adenopathy syndrome (PFAPA), pyogenic arthritis-pyoderma gangrenosum-acne (PAPA) syndrome, Schnitzier's Syndrome, Sweet's Sydrome, systemic juvenile idiopathic arthritis (sJIA) or Still's Disease and adult-onset Still's Disease (AOSD), and tumor necrosis factor (TNF) receptor-associated periodic syndrome (TRAPS).

The terms "binding" and variants thereof (such as "bound" and "bind(s)"), particularly when used in reference to two or more entities, refers to a covalent or non-covalent association of the entities (e.g., a compound and an agent within a pharmaceutical composition or a compound and its target (e.g., CDK7) within a cell). "Direct" binding occurs when two entities physically contact one another (e.g., through a covalent or non-covalent chemical bond) while indirect binding occurs when at least one of the entities physically contacts an intermediate entity that brings the entities into physical proximity with one another (e.g., within a complex). Binding can be assessed in a variety of contexts (e.g., in assays in which the entities are fully or partially isolated or in more complex, naturally occurring or model systems (e.g., in a tissue, organ, or cell in vivo or ex vivo)). Assays for binding may assess biological activity (e.g., the ability of a compound described herein to inhibit the biological activity of a target (e.g., CDK7)).

The term "biological sample" refers to a sample obtained or derived from a biological source of interest (e.g., a tissue or organism (e.g., an animal or human patient) or cell culture). For example, a biological sample can be a sample obtained from an individual (e.g., a patient or an animal model) suffering from a disease (or, in the case of an animal model, a simulation of that disease in a human patient) to be diagnosed and/or treated by the methods of this invention or from an individual serving in the capacity of a reference or control (or whose sample contributes to a reference standard or control population). The biological sample can contain a biological cell, tissue or fluid or any combination thereof. For example, a biological sample can be or can include ascites; blood; blood cells; a bodily fluid, any of which may include or exclude cells (e.g., tumor cells (e.g., circulating tumor cells (CTCs) found in at least blood or lymph vessels)); bone marrow or a component thereof (e.g., hematopoietic cells, marrow adipose tissue, or stromal cells); cerebrospinal fluid (CSF); feces; flexural fluid; free-floating nucleic acids (e.g., circulating tumor DNA); gynecological fluids; hair; immune infiltrates; lymph; peritoneal fluid; plasma; saliva; skin or a component part thereof (e.g., a hair follicle); sputum; surgically-obtained specimens; tissue scraped or swabbed from the skin or a mucus membrane (e.g., in the nose, mouth, or vagina); tissue or fine needle biopsy samples; urine; washings or lavages such as a ductal lavage or broncheoalveolar lavage; or other body fluids, tissues, secretions, and/or excretions. A biological sample may include cancer cells or immune cells, such as NK cells and/or macrophages, which are found in many tissues and organs, including the spleen and lymph nodes. Samples of, or samples obtained from, a bodily fluid (e.g., blood, CSF, lymph, plasma, or urine) may include tumor cells (e.g., CTCs) and/or free-floating or cell-free nucleic acids. Cells (e.g., cancer cells) within the sample may have been obtained from an individual patient for whom a treatment is intended. Samples used in the form in which they were obtained may be referred to as "primary" samples, and samples that have been further manipulated (e.g., by removing one or more components of the sample) may be referred to as "secondary" or "processed" samples. Such processed samples may contain or be enriched for a particular cell type (e.g., a CDK7-expressing cell, which may be a tumor cell), cellular component (e.g., a membrane fraction), or cellular material (e.g., one or more cellular proteins, including CDK7, DNA, or RNA (e.g., mRNA), which may encode CDK7 and may be subjected to amplification).

The term "biologically active" describes an agent (e.g., a compound described herein) that produces an observable biological effect or result in a biological system or model thereof (e.g., in a human, other animal, or a system maintained in cell/tissue culture or in vitro). The "biological activity" of such an agent can manifest upon binding between the agent and a target (e.g., a cyclin-dependent kinase (e.g., CDK7)), and it may result in modulation (e.g., induction, enhancement, or inhibition) of a biological pathway, event, or state (e.g., a disease state). For example, the agent can modulate a cellular activity (e.g., stimulation of an immune response or inhibition of homologous recombination repair), time spent in a phase of the cell cycle (which may alter the rate of cellular proliferation), or initiation of apoptosis or activation of another pathway leading to cell death (which may lead to tumor regression). A biological activity and, optionally, its extent, can be assessed using known methods to detect any given immediate or downstream product of the activity or any event associated with the activity (e.g., inhibition of cell growth or tumor regression).

The term "cancer" refers to a disease in which biological cells exhibit an aberrant growth phenotype characterized by loss of control of cell proliferation to an extent that will be detrimental to a patient having the disease. A cancer can be classified by the type of tissue in which it originated (histological type) and/or by the primary site in the body in which the cancer first developed. Based on histological type, cancers are generally grouped into six major categories: carcinomas; sarcomas; myelomas; leukemias; lymphomas; and mixed types. A cancer treated as described herein may be of any one of these types and may comprise cells that are precancerous (e.g., benign), malignant, pre-metastatic, metastatic, and/or non-metastatic. A patient who has a malignancy or malignant lesion has a cancer. The present disclosure specifically identifies certain cancers to which its teachings may be particularly relevant, and one or more of these cancers may be characterized by a solid tumor or by a hematologic tumor, which may also be known as a blood cancer (e.g., of a type described herein). Although not all cancers manifest as solid tumors, we may use the terms "cancer cell" and "tumor cell" interchangeably to refer to any malignant cell.

The term "carrier" refers to a diluent, adjuvant, excipient, or other vehicle with which an active pharmaceutical agent (e.g., a compound of the invention, or a pharmaceutically acceptable salt, solvate, stereoisomer, tautomer, or isotopic form thereof) is formulated for administration. The carrier, in the amount and manner incorporated into a pharmaceutical composition, will be non-toxic to the subject and will not destroy the biological activity of the active ingredient (e.g., the compound or other specified form thereof) with which it is formulated. The carrier can be a sterile or sterilizable liquid, such as a water (e.g., water for injection) or a natural or synthetic oil (e.g., a petroleum-based or mineral oil, an animal oil, or a vegetable oil (e.g., a peanut, soybean, sesame, or canola oil)). The carrier can also be a solid; a liquid that includes one or more solid components (e.g., a salt, for example, a "normal saline"); a mixture of solids; or a mixture of liquids.

The term "comparable" refers to two or more items (e.g., agents, entities, situations, sets of conditions, etc.) that are not identical to one another but are sufficiently similar to permit comparison therebetween so that one of ordinary skill in the art will appreciate that conclusions may reasonably be drawn based on differences or similarities observed. In some embodiments, comparable sets of conditions, circumstances, individuals (e.g., an individual patient or subject), or populations are characterized by a plurality of substantially identical features and one or a small number of varied features. One of ordinary skill in the art will understand, in context, what degree of identity is required in any given circumstance for two or more items to be considered comparable. For example, two items are comparable to one another when they have in common a sufficient number and type of substantially identical features to warrant a reasonable conclusion that any differences in results obtained or phenomena observed with the items are caused by or are indicative of the variation in those features that are varied. In some embodiments, a comparable item serves as a "control." For example, a "control subject/population" can be an untreated (or placebo-treated) individual/population who/that is afflicted with the same disease as an individual/population being treated.

The term "combination therapy" refers to those situations in which a subject is exposed to two or more therapeutic regimens (e.g., two or more therapeutic agents (e.g., three agents)) to treat a single disease (e.g., a cancer). The two or more regimens/agents may be administered simultaneously or sequentially. When administered simultaneously, a dose of the first agent and a dose of the second agent are administered at about the same time, such that both agents exert an effect on the patient at the same time or, if the first agent is faster- or slower-acting than the second agent, during an overlapping period of time. When administered sequentially, the doses of the first and second agents are separated in time, such that they may or may not exert an effect on the patient at the same time. For example, the first and second agents may be given within the same hour or same day, in which case the first agent would likely still be active when the second is administered. Alternatively, a much longer period of time may elapse between administration of the first and second agents, such that the first agent is no longer active when the second is administered (e.g., all doses of a first regimen are administered prior to administration of any dose(s) of a second regimen by the same or a different route of administration, as may occur in treating a refractory cancer). For clarity, combination therapy does not require that individual agents be administered together in a single composition or at the same time, although in some embodiments, two or more agents, including a compound of the invention and a second agent described herein, may be administered within the same period of time (e.g., within the same hour, day, week, or month).

The term "compound" means a chemical compound (e.g., a compound represented by a structural Formula depicted herein, a sub-genus thereof (e.g., Formula (Ia)), or a species thereof, and any specified forms thereof). Any given compound described herein can be biologically active (e.g., as an inhibitor of CDK7) and may be utilized for a purpose described herein, including therapeutic and prophylactic uses (e.g., when contained in a pharmaceutical composition in a therapeutically effective or prophylactically effective amount, administered to a patient, incorporated into a medicament or into a kit, or otherwise used as described herein). Two compounds that have the same molecular formula but differ in the arrangement of their atoms in space are termed "stereoisomers." The stereoisomers of any referenced or depicted structure can be enantiomers, which are non-superimposable mirror images of each other, or diastereomers, which are not mirror images of each other (e.g., cis trans isomers and conformational isomers). These include the R and S configurations for each asymmetric center, Z and E double bond isomers, and Z and E conformational isomers. Compositions containing a single type of stereochemical isomer as well as enantiomeric, diastereomeric, and geometric (or conformational) mixtures of the present compounds are within the scope of the invention. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The terms "dosage form," "formulation," and "preparation" refer to compositions that contain a compound of the invention, or a salt, solvate, stereoisomer, tautomer, isotopic, or other specified form thereof, or to other biologically or therapeutically active ingredients suitable for use as described herein (e.g., one or more of an additional/second agent useful in a combination therapy described herein). The term "unit dosage form" refers to a physically discrete unit of or containing a compound of the invention, or a salt, solvate, stereoisomer, tautomer, isotopic, or other specified form thereof, any of which can be pharmaceutically acceptable. One or more of an additional/second agent can also be formulated, administered, or used as described herein in a unit dosage form. Each such unit can contain a predetermined quantity of the active ingredient, which may be the amount prescribed for a single dose (i.e., an amount expected to correlate with a desired outcome when administered as part of a therapeutic or prophylactic regimen) or a fraction thereof (e.g., a unit dosage form (e.g., a tablet or capsule) may contain one half of the amount prescribed for a single dose, in which case a patient would take two unit dosage forms (i.e., two tablets or two capsules)). One of ordinary skill in the art will appreciate that the total amount of a composition or agent administered to a particular subject is determined by one or more attending physicians and may involve administration of multiple unit dosage forms (e.g., as described herein).

The term "dosing regimen" refers to the unit dosage form(s) administered to, or prescribed for, a subject, and typically includes more than one dose separated by periods of time (e.g., as described herein). The dosage form(s) administered within a dosing regimen can be of the same unit dose amount or of different amounts. For example, a dosing regimen can include a first dose in a first dose amount, followed by one or more additional doses in a second dose amount that is the same as or different from the first dose amount.

An "effective amount" refers to an amount of an agent (e.g., a compound described herein, whether of the invention or a "second" agent) that produces the desired effect for which it is administered. In some embodiments, the term refers to an amount that is sufficient, when administered to a population suffering from or susceptible to a disease in accordance with a therapeutic dosing regimen, to treat the disease, in which case the effective amount may also be referred to as a "therapeutically effective amount." One of ordinary skill in the art will appreciate that a therapeutically effective amount may not achieve a successful treatment in any particular individual (i.e., in any given individual patient). Rather, a therapeutically effective amount provides a desired pharmacological response in a significant or certain number of subjects when administered to a population of patients in need of such treatment. Where the agent is administered for prophylaxis, the "prophylactically effective amount" provides a desired result (i.e., delaying the onset of one or more signs or symptoms of a disease) in a significant or certain number of subjects in a population that does not exhibit signs and/or symptoms of the disease. A reference to an effective amount may be a reference to an amount of an agent administered or an amount measured in one or more specific tissues (e.g., a tissue affected by the disease) or fluids (e.g., blood, saliva, urine, etc.) after administration.

The term "hydrate" refers to a compound or a specified form thereof that is combined with water; as is understood in the art, a hydrate is a solvate in which the solvent is water. The amount of water contained in the hydrate can be expressed as a ratio of the number of water molecules to the number of compound molecules. Thus, a hydrate of a compound may be represented by a general formula such as R·x $H_2O$, where R is the compound and x is a number greater than 0. For example, where x is 1, the hydrate is a monohydrate; where x is 0.5, the hydrate is a hemihydrate; where x is 2, the hydrate is a dihydrate; and where x is 6, the hydrate is a hexahydrate.

"Improve(s)," "increase(s)" or "reduce(s)/decrease(s)" (and obvious variants thereof, such as "improved" or "improving") are terms used to characterize the manner in which a value changes or has changed relative to a reference value. For example, a measurement obtained from a patient (or a biological sample obtained therefrom) prior to treatment can be increased or reduced/decreased relative to that measurement when obtained during or after treatment in the same patient, a control patient, on average in a patient population, or in biological sample(s) obtained therefrom. The value may be improved in either event, depending on whether an increase or decrease is associated with a positive therapeutic outcome.

As used herein, the term "inflammatory disease" refers to a disease caused by, resulting from, or resulting in inflammation or to a dysregulated inflammatory reaction that causes an exaggerated response by macrophages, granulocytes, and/or T-lymphocytes that leads to abnormal tissue damage and/or cell death. An inflammatory disease can be either acute or chronic and can result from infectious agents or non-infectious causes. Inflammatory diseases include, without limitation, acute anaphylaxis, Adult Respiratory Distress Syndrome (ARDS), an allergy, allograft rejection, ankylosing spondylitis, appendicitis, arteriosclerosis, arteritis (e.g., giant cell arteritis), asbestosis, atherosclerosis, asthma, arthritis (e.g., gouty arthritis, degenerative arthritis, inflammatory arthritis, and rheumatoid arthritis), arthrosteitis, an autoimmune disease, berylliosis, blepharitis, bronchiectasis, bronchiolitis, bronchitis (e.g., chronic bronchitis), bursitis, cellular interstitial pneumonia, cellulitis, cervicitis, cholangitis, chorioamnionitis, conjunctivitis, chronic cholecystitis, Crohn's disease, cystic fibrosis, cystitis, dacryoadenitis, delayed-type hypersensitivity reactions (e.g., poison ivy dermatitis), dermatomyositis, desquamative interstitial pneumonia, diabetes (e.g., Type I), encephalitis, endocarditis, endometritis, enteritis, enterocolitis, epicondylitis, epididymitis, extrinsic allergic alveolitis, fasciitis, fibrositis, gastritis, gastroenteritis, giant cell interstitial pneumonia, gingivitis, glomerulonephritis, Goodpasture's disease, Graves' disease, Hashimoto's thyroiditis, hayfever, hepatitis, host-versus-graft rejection, ileitis, immediate hypersensitivity reactions, inflammatory bowel disease (IBD), inflammatory dermatoses, iritis, ischemia (ischemic injury), laryngitis, lymphoid interstitial pneumonia, mixed connective tissue disease, multiple sclerosis, myasthenia gravis, myelitis, myocarditis, necrotizing enterocolitis, nephritis, omphalitis, oophoritis, orchitis, osteitis, osteomyelitis, optic neuritis, otitis, pancreatitis, parotitis, pemphigoid, pemphigus, pericarditis, pernicious anemia, pharyngitis, phlebitis, pleuritis, pneumoconiosis, pneumonia, pneumonitis, polymyalgia rheumatica (PMR), polymyositis, proctitis, progressive systemic sclerosing cholangitis, prostatis, psoriasis, pyelonephritis, reperfusion injury, respiratory tract inflammation, rheumatic fever, rhinitis, salpingitis, sarcoidosis, sclerosis (scleroderma), silicosis, sinusitis, Sjogren's syndrome, stomatitis, synovitis, systemic lupus erythematosus (SLE), talcosis, temporal arteritis, tendonitis, testitis, tonsillitis, transverse myelitis, necrotizing fasciitis, ulcerative colitis, urethritis, urocystitis, usual interstitial pneumonitis (UIP), uvetis, vaginitis, vasculitis, vulvitis, vulvovaginitis, and Wegener's granulomatosis and related forms of angiitis (temporal arteritis and polyarteritis nodosa).

The term "inhibitor" refers to an agent, including a compound described herein or a specified form thereof, whose presence (e.g., at a certain level or in a certain form) correlates with a decrease in the expression or activity of another agent (i.e., the inhibited agent or target) or a decrease in the occurrence of an event (e.g., cellular proliferation, tumor progression, or metastasis, inflammation, infection, or autoimmunity). In some embodiments, an inhibitor exerts its influence on a target by binding to the target, directly or indirectly, by way of covalent bonds or non-covalent association. Inhibition can be assessed in silico, in vitro (e.g., in a cell, tissue, or organ culture or system), or in vivo (e.g., in a patient or animal model).

The term "isotopic form" is used to describe a compound that contains at least one isotopic substitution; the replacement of an isotope of an atom with another isotope of that atom. For example, the substitution can be of $^2H$ (deuterium) or $^3H$ (tritium) for $^1H$. Thus, we may use the terms "$^1H$," "H," or "hydrogen atom" to refer to the naturally occurring form of hydrogen having a single proton in its nucleus. Other substitutions in isotopic forms include $^{11}C$, $^{13}C$ or $^{14}C$ for $^{12}C$; $^{13}N$ or $^{15}N$ for $^{14}N$; $^{17}O$ or $^{18}O$ for $^{16}O$; $^{36}Cl$ for $^{35}C$; $^{18}F$ for $^{19}F$; $^{131}I$ for $^{127}I$; etc. . . . Such compounds have use, for example, as analytical tools, as probes in biological assays, and/or as therapeutic or prophylactic agents for use in accordance with the present invention. In particular, an isotopic substitution of deuterium ($^2H$) for hydrogen may slow down metabolism, shift metabolism to other sites on the compound, slow down racemization and/or have other effects on the pharmacokinetics of the compound that may be beneficial (e.g., therapeutically beneficial).

The terms "neoplasm" and "tumor" are used herein interchangeably and refer to an abnormal mass of tissue in which the growth of the mass surpasses and is not coordinated with the growth of a normal tissue. A neoplasm or tumor may be "benign" or "malignant" depending on the following characteristics: the degree of cellular differentiation (including morphology and functionality), rate of growth, local invasion, and metastasis. A "benign neoplasm" is generally well differentiated, has a slower growth rate than a malignant neoplasm, and remains localized to the site of origin (i.e., does not have the capacity to infiltrate, invade, or metastasize to distant sites). Benign neoplasms include, but are not limited to, acrochordons, adenomas, chondromas, intraepithelial neoplasms, lentigos, lipomas, sebaceous hyperplasias, seborrheic keratoses, and senile angiomas. The benign neoplasm can also be tuberous sclerosis, or tuberous sclerosis complex (TSC) or epiloia (derived from "epilepsy, low intelligence, adenoma sebaceum"). Benign neoplasms can later give rise to malignant neoplasms (believed to occur as a result of genetic changes in a subpopulation of the tumor's neoplastic cells), and such neoplasms are referred to as "pre-malignant neoplasms." An exemplary pre-malignant neoplasm is a teratoma. In contrast, a "malignant neoplasm" is generally poorly differentiated (anaplasia) and grows rapidly with progressive infiltration, invasion, and destruction of surrounding tissue. Malignant neoplasms also generally have the capacity to metastasize to distant sites.

The terms "patient" and "subject" refer to any organism to which a compound described herein, or a specified form thereof, is administered in accordance with the present invention, e.g., for experimental, prophylactic, and/or therapeutic purposes. Typical subjects include animals (e.g., mammals such as mice, rats, rabbits, non-human primates, and humans; domesticated animals, such as dogs and cats; and livestock or any other animal of agricultural or commercial value). In some embodiments, a subject is suffering from a disease (e.g., a proliferative disease, such as cancer) described herein.

A "pharmaceutical composition" or "pharmaceutically acceptable composition," which we may also refer to as a "pharmaceutical formulation" or "pharmaceutically acceptable formulation," is a composition/formulation in which an active agent (e.g., an active pharmaceutical ingredient (e.g., a compound, salt, solvate, stereoisomer, tautomer, or isotopic form thereof)) is formulated together with one or more pharmaceutically acceptable carriers. The active agent/ingredient can be present in a unit dose amount appropriate for administration in a therapeutic regimen that shows a statistically significant probability of achieving a predetermined therapeutic effect when administered to a relevant population. The pharmaceutical composition may be specially formulated for administration in solid or liquid form, including such forms made for oral or parenteral administration. For oral administration, the pharmaceutical composition can be formulated, for example, as an aqueous or non-aqueous solution or suspension or as a tablet or capsule. For systemic absorption through the mouth, the composition can be formulated for buccal administration, sublingual administration, or as a paste for application to the tongue. For parenteral administration, the composition can be formulated, for example, as a sterile solution or suspension for subcutaneous, intramuscular, intravenous, intra-arterial, intraperitoneal, intra-tumoral, or epidural injection. Pharmaceutical compositions comprising an active agent/ingredient (e.g., a compound described herein or a specified form thereof) can also be formulated as sustained-release formulations or as a cream, ointment, controlled-release patch, or spray for topical application. Creams, ointments, foams, gels, and pastes can also be applied to mucus membranes lining the nose, mouth, vagina, and rectum. Any of the compounds described herein and any pharmaceutical composition containing such a compound may also be referred to as a "medicament."

The term "pharmaceutically acceptable," when applied to a carrier used to formulate a composition disclosed herein (e.g., a pharmaceutical composition), means a carrier that is compatible with the other ingredients of the composition and not deleterious to a patient (e.g., it is non-toxic in the amount required and/or administered (e.g., in a unit dosage form)).

The term "pharmaceutically acceptable," when applied to a salt, solvate, stereoisomer, tautomer, or isotopic form of a compound described herein, refers to a salt, solvate, stereoisomer, tautomer, or isotopic form that is, within the scope of sound medical judgment, suitable for use in contact with the tissues of humans (e.g., patients) and lower animals (including, but not limited to, mice and rats used in laboratory studies) without unacceptable toxicity, irritation, allergic response and the like, and that can be used in a manner commensurate with a reasonable benefit/risk ratio. Many pharmaceutically acceptable salts are well known in the art (see, e.g., Berge et al., *J. Pharm. Sci.* 66:1-19, 1977). Pharmaceutically unacceptable salts, solvates, stereoisomers, tautomers or isotopic forms of the present compounds are also within the scope of the present invention and have utility in, for example, chemical processes and syntheses and in experiments performed in vitro. In pharmaceutically unacceptable compositions, a compound, salt, solvate, stereoisomer, tautomer, or isotopic form thereof may be present in an amount that is too concentrated or too dilute for administration to a patient.

A "polypeptide" is a polymer of amino acid residues, regardless of length, source, or post-translational modification; it encompasses but is not limited to full-length, naturally occurring proteins. Where a polypeptide is bound by (e.g., specifically bound) or otherwise interacts with a composition described herein, we may refer to that polypeptide as the composition's "target."

The terms "prevent(s)," "prevention," "prophylaxis/prophylactic," and the like, when used in connection with the occurrence of disease (e.g., a proliferative disease, such as a cancer), refer to reducing the risk of developing the disease and/or to delaying the onset of a sign or symptom thereof. Prevention can be considered complete when onset has been delayed for a predefined time.

A "proliferative disease" is a disease characterized by an excessive proliferation of cells. Proliferative diseases are associated with: (1) pathological proliferation of normally quiescent or normally proliferating cells; (2) pathological migration of cells from their normal location (e.g., metastasis of neoplastic cells); (3) pathological expression of proteolytic enzymes such as the matrix metalloproteinases (e.g., collagenases, gelatinases, and elastases), which can lead to unwanted turnover of cellular matrices; and/or (4) pathological angiogenesis, as occurs in proliferative retinopathy and tumor metastasis. Exemplary proliferative diseases include cancers, benign neoplasms, and angiogenesis that accompanies and facilitates a disease state (defined above as pathologic angiogenesis).

The term "reference" describes a standard or control relative to which a comparison is made. For example, an agent, animal (e.g., a subject (e.g., an animal used in laboratory studies)), cell or cells, individual (e.g., an individual patient), population, sample (e.g., biological sample), sequence or value of interest is compared with a reference or control agent, animal (e.g., a subject (e.g., an animal used in laboratory studies)), cell or cells, individual (e.g., an individual patient), population, sample, or sequence or value, respectively. In some embodiments, a reference or control is tested and/or determined substantially simultaneously with the testing or determination of interest. In other embodiments, a reference or control is a historical reference or control, optionally embodied in a tangible medium. Typically, as would be understood by one of ordinary skill in the art, a reference or control is determined or characterized under comparable conditions to those under assessment, and one of ordinary skill in the art will appreciate when sufficient similarities are present to justify reliance on and/or comparison to a particular possible reference or control.

The term "response" with respect to a treatment may refer to any beneficial alteration in a subject's or patient's condition that occurs as a result of, or correlates with, treatment. Such an alteration may include stabilization of the condition (e.g., prevention of deterioration that would have taken place in the absence of the treatment (e.g., stable disease)), amelioration of symptoms of the condition, and/or improvement in the prospects for cure of the condition (e.g., tumor regression), etc. The response may be a cellular response (e.g., a tumor's response) and can be measured using a wide variety of criteria, including clinical criteria and objective criteria, known in the art. Techniques for assessing a response include, but are not limited to, assay assessment, clinical examination, positron emission tomography, X-ray, CT scan, MRI, ultrasound, endoscopy, laparoscopy, assessing the presence or level of tumor markers in a sample obtained from a subject, cytology, and/or histology. Regarding measuring tumor response, methods and guidelines for assessing response to treatment are discussed in Therasse et al. (*J. Natl. Cancer Inst.*, 92(3):205-216, 2000). The exact response criteria can be selected by one of ordinary skill in the art in any appropriate manner, provided that when comparing groups of cancers and/or patients, the groups to be compared are assessed based on the same or comparable criteria for determining response rate.

The term "solvate" refers to a compound formed by the combination of molecules of a solute with molecules of solvent. Solvents that can be used to form a solvate include water, methanol, ethanol, acetic acid, DMSO (dimethyl sulfoxide), THF (tetrahydrofuran), diethyl ether, and the like. A solvate in which the solvent is water is referred to as a hydrate. A compound can be prepared as a liquid or solid solvate form, e.g., as a crystalline solvate. The solvate can be pharmaceutically acceptable and can be either a stoichiometric or non-stoichiometric solvate. In certain instances, the solvate will be capable of isolation, for example, when one or more solvent molecules are incorporated in the crystal lattice of a crystalline solid. "Solvate" encompasses both solution-phase and isolable solvates, and representative solvates include hydrates, ethanolates, and methanolates.

The term "specific," as used herein with reference to an agent (e.g., a compound) having an activity (e.g., inhibition of a target), means that the agent discriminates between potential target entities or states. For example, an agent binds "specifically" to its intended target (or otherwise specifically inhibits its target) if it preferentially binds or otherwise inhibits the expression or activity of that target in the presence of one or more alternate targets. Although the invention is not so limited, a specific and direct interaction can depend upon recognition of a particular structural feature of the target (e.g., an epitope, a cleft, or a binding site). Specificity need not be absolute; the degree of specificity need only be enough to result in an effective treatment without unacceptable side effects. The specificity of an agent can be evaluated by comparing the effect of the agent on an intended target or state relative to its effect on a distinct target or state. The effects on the intended and distinct targets can each be determined or the effect on the intended target can be determined and compared to a reference standard developed at an earlier time (e.g., a reference specific binding agent or a reference non-specific binding agent). In some embodiments, the agent does not detectably bind the competing alternative target under conditions in which it detectably (and, preferably, significantly) binds its intended target and/or does not detectably inhibit the expression or activity of the competing target under conditions in which it detectably (and, preferably, significantly) inhibits the expression or activity of its intended target. A compound of the invention or a salt, solvate, stereoisomer, tautomer, or isotopic form thereof, may exhibit, with respect to its target(s), a higher on-rate, lower off-rate, increased affinity, decreased dissociation, and/or increased stability compared with the competing alternative target, and any of these parameters can be assessed in methods of the invention.

The term "substantially" refers to the qualitative condition of exhibiting a characteristic or property of interest to a total or near-total extent or degree. One of ordinary skill in the art will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. For example, a chemical reaction may be characterized as substantially complete even though the yield is well below 100%. Certain features may also be deemed "substantially identical" when they are about the same and/or exhibit about the same activity. For example, two nearly identical compounds that produce about the same effect on an event (e.g., cellular proliferation) may be described as substantially similar. With regard to the purity of a compound or composition, "substantially pure" is defined below.

An individual (e.g., an individual subject or patient) who is "susceptible to" a disease (e.g., a cancer) has a greater than average risk for developing the disease. Such an individual may not display any symptoms of the disease and may not have been diagnosed with the disease but is considered at risk due to, for example, exposure to conditions associated with development of the disease (e.g., exposure to a carcinogen). The risk of developing a disease can be population-based.

A "sign or symptom is reduced" when one or more objective signs or subjective symptoms of a particular disease are reduced in magnitude (e.g., intensity, severity, etc.) and/or frequency. A delay in the onset of a particular sign or symptom is one form of reducing the frequency of that sign or symptom. Reducing a sign or symptom can be achieved by, e.g., a "therapeutically active" compound.

The term "substantially pure," when used to refer to a compound described herein or a specified form thereof, means that a preparation of the compound or the specified form thereof is more than about 85% (w/w) compound or the specified form thereof (e.g., more than about 90%, 95%, 97%, 98%, 99%, or 99.9% compound or a salt, solvate, stereoisomer, tautomer, or isomer).

A "tautomer" is an interchangeable form of a particular compound structure that varies by virtue of displaced hydrogen atoms and electrons. Thus, two chemical structures may be in equilibrium through the movement of $\pi$ electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base. Tautomeric forms can be used to optimize chemical reactivity and biological activity of a compound of interest.

A "therapeutic regimen" refers to a dosing regimen that, when administered across a relevant population, is correlated with a desired therapeutic outcome.

The term "treatment," and linguistic variants thereof, such as "treat(s)" and "treating," refer to any use of a pharmaceutical composition or administration of a therapy that partially or substantially completely alleviates, ameliorates, relives, inhibits, reduces the severity of, and/or reduces the incidence of one or more signs or symptoms of a particular disease (e.g., a proliferative disease such as cancer). The subject being treated (or who has been identified as a candidate for treatment (e.g., a "newly diagnosed" patient) may exhibit only early signs or symptoms of the disease or may exhibit one or more established or advanced signs or symptoms of the disease. "Treatment" is distinguished from "prophylaxis" (defined below). In that case, the subject will not exhibit signs and/or symptoms of the disease and/or may be known to have one or more susceptibility factors that are statistically correlated with increased risk of development of the relevant disease. However, once a patient exhibits signs or symptoms of a disease and has been treated, treatment may be continued to delay progression of the disease (e.g., in the event of a localized cancer, treatment may delay tumor progression (i.e., growth) or metastasis) or to delay or prevent recurrence (e.g., reappearance of a tumor).

The Applicant describes herein compounds of the invention having structural Formula (I):

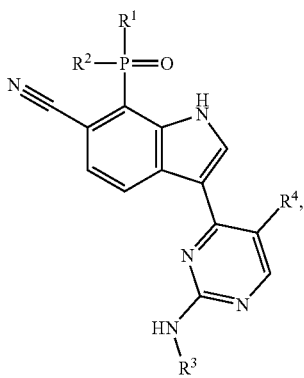

(I)

or a pharmaceutically acceptable salt, solvate (e.g., hydrate), stereoisomer, tautomer, or isotopic form thereof. Within Formula (I), $R^1$ is methyl or ethyl; $R^2$ is methyl or ethyl; $R^3$ is 5-methylpiperidin-3-yl, 5,5-dimethylpiperidin-3-yl, 6-methylpiperidin-3-yl, or 6,6-dimethylpiperidin-3-yl; and $R^4$ is —$CF_3$ or chloro. In some embodiments, in a compound of structural Formula (I), or a specified form thereof (e.g., a pharmaceutically acceptable salt, solvate, stereoisomer, or tautomer thereof), one or more atoms (e.g., one or more carbon and/or hydrogen atoms within, e.g., a monocyclic or bicyclic ring structure, $R^1$, $R^2$, $R^3$, and/or $R^4$) are replaced with an isotope of the originally present atom (e.g., an originally present $^{12}C$ is replaced with $^{13}C$ or 14C and/or an originally present $^1H$ is replaced with $^2H$ or $^3H$). That is, the invention encompasses isotopic forms of a compound of structural Formula (I) as well as isotopic forms of a salt, solvate, stereoisomer, or tautomer thereof. As noted, a compound of structural Formula (I) can be in the form of a solvate (e.g., a hydrate), and the invention encompasses solvates (e.g., hydrates) of a compound of structural Formula (I) as well as solvates of a salt, stereoisomer, tautomer, or isotopic form of a compound of Formula (I). As noted, a compound of structural Formula (I) can be in the form of a salt, and the invention encompasses salts of a compound of Formula (I) when the compound is in another specified form (e.g., the invention encompasses a salt of a solvate, stereoisomer, tautomer, or isotopic form of a compound of Formula (I)). In some embodiments, including those featuring the specified forms just mentioned, the compound has structural Formula (Ia):

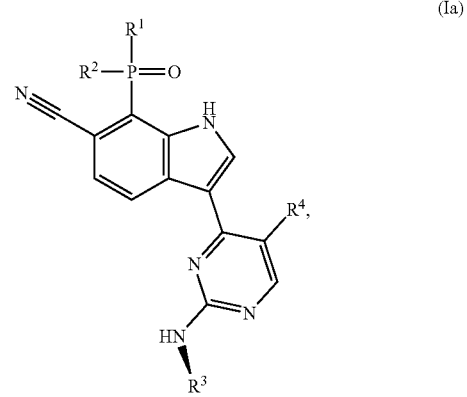

(Ia)

or is a pharmaceutically acceptable salt, solvate (e.g., hydrate), tautomer, isotopic, or other specified form thereof (e.g., a pharmaceutically acceptable salt thereof (e.g., a salt of an isotopic form)). $R^1$, $R^2$, and $R^4$ are as defined for structural Formula (I), and $R^3$ is

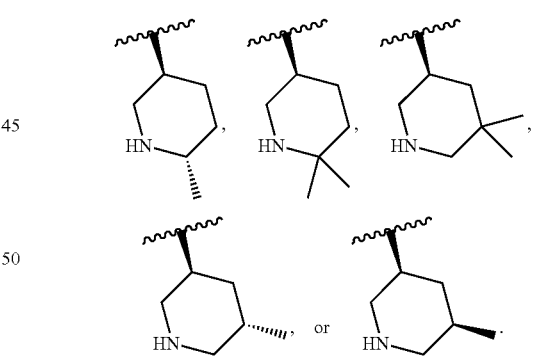

As indicated above with regard to Formula (I), any compound of Formula (Ia) or any salt, solvate, or tautomer thereof can be an isotopic form (e.g., one or more carbon and/or hydrogen atoms in a monocyclic or bicyclic ring structure, $R^1$, $R^2$, $R^3$, and/or $R^4$ is replaced by an isotope thereof (e.g., deuterium for $^1H$)).

In some embodiments of a structural formula disclosed herein (e.g., Formula (I) or (Ia)), each of $R^1$ and $R^2$ is, independently, methyl, —$CD_3$, ethyl, —$CD_2CD_3$, —$CH_2CD_3$, or —$CH_2CD_3$, where "D" represents deuterium.

In some embodiments, the compound of Formula (I) or Formula (Ia) is

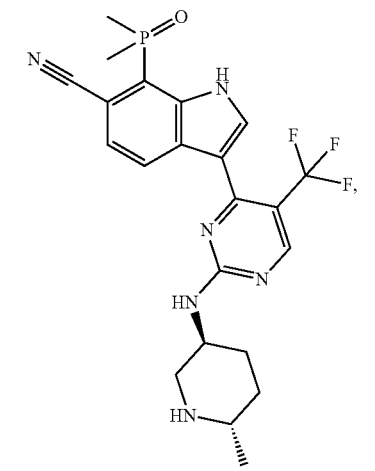

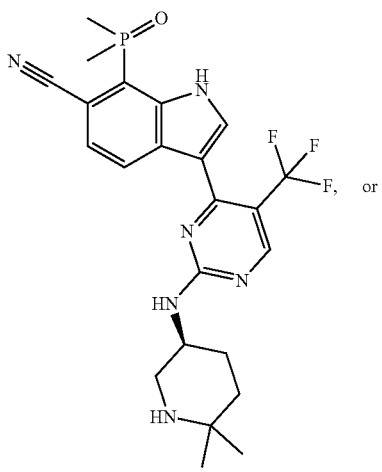 or

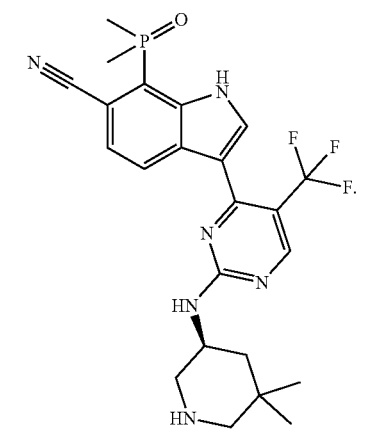

In other embodiments, the invention features a pharmaceutically acceptable salt, solvate (e.g., hydrate), tautomer, or isotopic form of any of the three foregoing compounds. In other embodiments, the invention features another specified form of any of the three foregoing compounds. For example, the invention encompasses a pharmaceutically acceptable salt of a solvate (e.g., hydrate), tautomer, or isotopic form of any of the three foregoing compounds.

In some embodiments, the compound is:

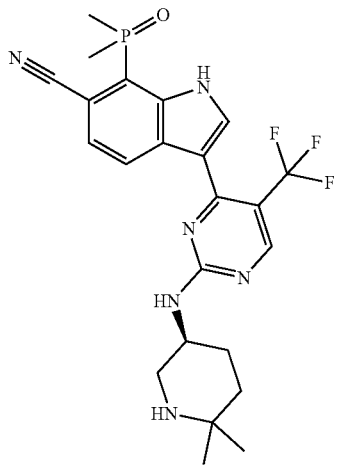 [SMILES: CC1(C)CC[C@H](Nc2ncc(C(F)(F)F)c(-c3c[nH]c4c(P(C)(C)=O)c(C#N)ccc34)n2)CN1]

or a pharmaceutically acceptable salt, solvate (e.g., hydrate), or tautomer thereof (e.g., a pharmaceutically acceptable salt thereof), or an isotopic variant of the compound or any of the foregoing specified forms thereof. The isotopic variant can be as otherwise described above (e.g., one or more hydrogen atoms (e.g., in the substituent

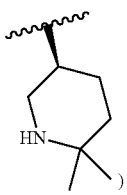 [SMILES: *[C@H]1CCC(C)(C)NC1]
)

is replaced by deuterium). In some embodiments of structural Formula (I) or Formula I(a), $R^3$ is (5S)-5-methylpiperidin-3-yl

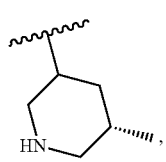

5,5-dimethylpiperidin-3-yl

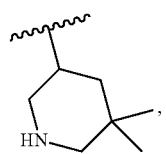 [SMILES: *C1CNCC(C)(C)C1]

(6S)-6-methylpiperidin-3-yl

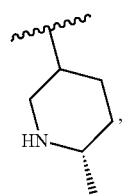 [SMILES: *C1CC[C@H](C)NC1]

6,6-dimethylpiperidin-3-yl,

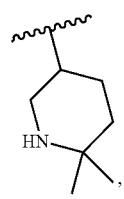 [SMILES: *C1CCC(C)(C)NC1]

(5S)-5-trideuteromethylpiperidin-3-yl

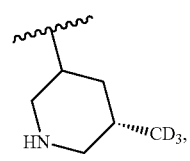 [SMILES: *C1CNC[C@@H](C([2H])([2H])[2H])C1]

5,5-di-trideuteromethylpiperidin-3-yl

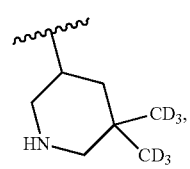

(6S)-6-trideuteromethyl-piperidin-3-yl

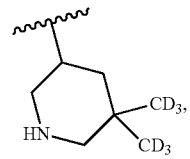

or 6,6-di-trideuteromethylpiperidin-3-yl

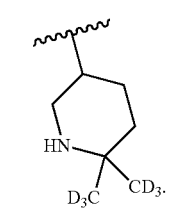 [SMILES: *C1CCC(C([2H])([2H])[2H])(C([2H])([2H])[2H])NC1]

In some embodiments of structural Formula (I) or Formula (Ia), $R^3$ is (3S,5S)-5-methylpiperidin-3-yl

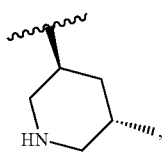 [SMILES: *[C@@H]1CNC[C@@H](C)C1]

(3S)-5,5-dimethylpiperidin-3-yl

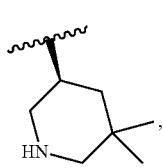

(3S,6S)-6-methylpiperidin-3-yl

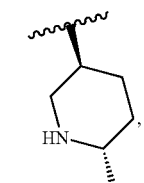

(3S)-6,6-dimethylpiperidin-3-yl

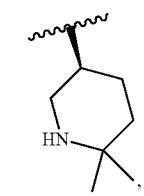 [SMILES: *[C@H]1CCC(C)(C)NC1]

(3S,5S)-5-trideuteromethylpiperidin-3-yl

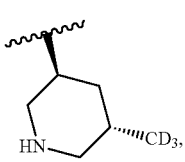 [SMILES: *[C@@H]1CNC[C@@H](C([2H])([2H])[2H])C1]

(3S)-5,5-di-trideuteromethylpiperidin-3-yl

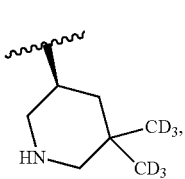

(3S,6S)-6-trideuteromethyl-methylpiperidin-3-yl

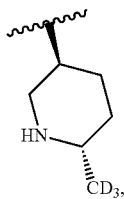

or (3S)-6,6-di-trideuteromethylpiperidin-3-yl

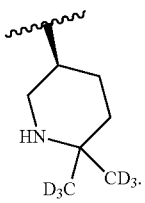

Where $R^3$ is as described above, $R^1$ can be methyl or ethyl; $R^2$ can be methyl or ethyl; and $R^4$ can be —$CF_3$ or chloro. For example, where $R^3$ is as described above, $R^1$ can be methyl, $R^2$ can be methyl, and $R^4$ can be —$CF_3$. It should also be noted that the stereochemical R/S designator for the attachment position of $R^3$ (e.g., the 3-position in the above substituted piperidine examples), is based on the $R^3$ group being attached to the core of Formula (I) or (Ia), which gives the core an R/S priority of "1" in the above examples.

In various, independent embodiments of structural Formula (I), (Ia), a species thereof or a specified form thereof: $R^1$ is methyl or ethyl; $R^2$ is methyl or ethyl; $R^1$ is methyl and $R^2$ is ethyl; $R^1$ and $R^2$ are simultaneously methyl; or $R^1$ and $R^2$ are simultaneously ethyl. In various embodiments, $R^3$ is 5-methylpiperidin-3-yl (e.g., (3S,5S)-5-methylpiperidin-3-yl), 5,5-dimethylpiperidin-3-yl (e.g., (3S)-5,5-dimethylpiperidin-3-yl), 6-methylpiperidin-3-yl (e.g., (3S,5S)-6-methylpiperidin-3-yl), or 6,6-dimethylpiperidin-3-yl (e.g., (3S)-6,6,dimethylpiperidin-3-yl); $R^3$ is (3S,5S)-5-methylpiperidin-3-yl; $R^3$ is (3S)-5,5-dimethylpiperidin-3-yl; $R^3$ is (3S,6S)-6-methylpiperidin-3-yl; or $R^3$ is (3S)-6,6-dimethylpiperidin-3-yl. In more specific embodiments, $R^1$ is methyl or ethyl, $R^2$ is methyl or ethyl, and $R^3$ is 5-methylpiperidin-3-yl (e.g., (3S,5S)-5-methylpiperidin-3-yl); $R^1$ is methyl or ethyl, $R^2$ is methyl or ethyl, and $R^3$ is 5,5-dimethylpiperidin-3-yl (e.g., (3S)-5,5-dimethylpiperidin-3-yl); $R^1$ is methyl or ethyl, $R^2$ is methyl or ethyl, and $R^3$ is 6-methylpiperidin-3-yl (e.g., (3S,6S)-6-methylpiperidin-3-yl); or $R^1$ is methyl or ethyl, $R^2$ is methyl or ethyl, and $R^3$ is 6,6-dimethylpiperidin-3-yl (e.g., (3S)-6,6-dimethylpiperidin-3-yl). In more specific embodiments, $R^1$ is methyl, $R^2$ is ethyl and $R^3$ is 5-methylpiperidin-3-yl (e.g., (3S,5S)-5-methylpiperidin-3-yl); $R^1$ is methyl, $R^2$ is ethyl and $R^3$ is 5,5-dimethylpiperidin-3-yl (e.g., (3S)-5,5-dimethylpiperidin-3-yl); $R^1$ is methyl, $R^2$ is ethyl and $R^3$ is 6-methylpiperidin-3-yl (e.g., (3S,6S)-6-methylpiperidin-3-yl); or $R^1$ is methyl, $R^2$ is ethyl and $R^3$ is 6,6-dimethylpiperidin-3-yl (e.g., (3S)-6,6-dimethylpiperidin-3-yl). In more specific embodiments, $R^1$ and $R^2$ are simultaneously methyl and $R^3$ is 5-methylpiperidin-3-yl (e.g., (3S,5S)-5-methylpiperidin-3-yl); $R^1$ and $R^2$ are simultaneously methyl and $R^3$ is 5,5-dimethylpiperidin-3-yl (e.g., (3S)-5,5-dimethylpiperidin-3-yl); $R^1$ and $R^2$ are simultaneously methyl and $R^3$ is 6-methylpiperidin-3-yl (e.g., (3S,6S)-6-methylpiperidin-3-yl); or $R^1$ and $R^2$ are simultaneously methyl and $R^3$ is 6,6-dimethylpiperidin-3-yl (e.g., (3S)-6,6-dimethylpiperidin-3-yl). In more specific embodiments, $R^1$ and $R^2$ are simultaneously ethyl and $R^3$ is 5-methylpiperidin-3-yl (e.g., (3S,5S)-5-methylpiperidin-3-yl); $R^1$ and $R^2$ are simultaneously ethyl and $R^3$ is 5,5-dimethylpiperidin-3-yl (e.g., (3S)-5,5-dimethylpiperidin-3-yl); $R^1$ and $R^2$ are simultaneously ethyl and $R^3$ is 6-methylpiperidin-3-yl (e.g., (3S,6S)-6-methylpiperidin-3-yl); or $R^1$ and $R^2$ are simultaneously ethyl and $R^3$ is 6,6-dimethylpiperidin-3-yl (e.g., (3S)-6,6-dimethylpiperidin-3-yl).

In some embodiments of structural Formula (I) or Formula (Ia), $R^4$ is —$CF_3$. In more specific embodiments, $R^1$ is methyl or ethyl, $R^2$ is methyl or ethyl, $R^3$ is 5-methylpiperidin-3-yl (e.g., (3S,5S)-5-methylpiperidin-3-yl) and $R^4$ is —$CF_3$; $R^1$ is methyl or ethyl, $R^2$ is methyl or ethyl, $R^3$ is 5,5-dimethylpiperidin-3-yl (e.g., (3S)-5,5-dimethylpiperidin-3-yl), and and $R^4$ is —$CF_3$; $R^1$ is methyl or ethyl, $R^2$ is methyl or ethyl, $R^3$ is 6-methylpiperidin-3-yl (e.g., (3S,6S)-6-methylpiperidin-3-yl), and $R^4$ is —$CF_3$; or $R^1$ is methyl or ethyl, $R^2$ is methyl or ethyl, $R^3$ is 6,6-dimethylpiperidin-3-yl (e.g., (3S)-6,6-dimethylpiperidin-3-yl), and $R^4$ is —$CF_3$. In more specific embodiments, $R^1$ is methyl, $R^2$ is ethyl, $R^3$ is 5-methylpiperidin-3-yl (e.g., (3S,5S)-5-methylpiperidin-3-yl) and $R^4$ is —$CF_3$; $R^1$ is methyl, $R^2$ is ethyl, $R^3$ is 5,5-dimethylpiperidin-3-yl (e.g., (3S)-5,5-dimethylpiperidin-3-yl) and $R^4$ is —$CF_3$; $R^1$ is methyl, $R^2$ is ethyl, $R^3$ is 6-methylpiperidin-3-yl (e.g., (3S,6S)-6-methylpiperidin-3-yl) and $R^4$ is —$CF_3$; or $R^1$ is methyl, $R^2$ is ethyl, $R^3$ is 6,6-dimethylpiperidin-3-yl (e.g., (3S)-6,6-dimethylpiperidin-3-yl), and $R^4$ is —$CF_3$. In more specific embodiments, $R^1$ and $R^2$ are simultaneously methyl, $R^3$ is 5-methylpiperidin-3-yl (e.g., (3,S,5S)-5-methylpiperidin-3-yl), and $R^4$ is —$CF_3$; $R^1$ and $R^2$ are simultaneously methyl, $R^3$ is 5,5-dimethylpiperidin-3-yl (e.g., (3S)-5,5-dimethylpiperidin-3-yl), and $R^4$ is —$CF_3$; $R^1$ and $R^2$ are simultaneously methyl, $R^3$ is 6-methylpiperidin-3-yl (e.g., (3S,6S)-6-methylpiperidin-3-yl), and $R^4$ is —$CF_3$; or $R^1$ and $R^2$ are simultaneously methyl, $R^3$ is 6,6-dimethylpiperidin-3-yl (e.g., (3S)-6,6-dimethylpiperidin-3-yl), and $R^4$ is —$CF_3$. In more specific embodiments, $R^1$ and $R^2$ are simultaneously ethyl, $R^3$ is 5-methylpiperidin-3-yl (e.g., (3S,5S)-5-methylpiperidin-3-yl), and $R^4$ is —$CF_3$; $R^1$ and $R^2$ are simultaneously ethyl, $R^3$ is 5,5-dimethylpiperidin-3-yl (e.g., (3S)-5,5-dimethylpiperidin-3-yl), and $R^4$ is —$CF_3$; $R^1$ and $R^2$ are simultaneously ethyl, $R^3$ is 6-methylpiperidin-3-yl (e.g., (3S,6S)-6-methylpiperidin-3-yl), and $R^4$ is —$CF_3$; or $R^1$ and $R^2$ are simultaneously ethyl, $R^3$ is 6,6-dimethylpiperidin-3-yl (e.g., (3S)-6,6-dimethylpiperidin-3-yl), and $R^4$ is —$CF_3$.

In some embodiments of structural Formula (I) or Formula (Ia), $R^4$ is chloro. In more specific embodiments, $R^1$ is methyl or ethyl, $R^2$ is methyl or ethyl, $R^3$ is 5-methylpiperidin-3-yl (e.g., (3S,5S)-5-methylpiperidin-3-yl) and $R^4$ is chloro; $R^1$ is methyl or ethyl, $R^2$ is methyl or ethyl, $R^3$ is 5,5-dimethylpiperidin-3-yl (e.g., (3S)-5,5-dimethylpiperidin-3-yl), and $R^4$ is chloro; $R^1$ is methyl or ethyl, $R^2$ is methyl or ethyl, $R^3$ is 6-methylpiperidin-3-yl (e.g., (3S,6S)-6-methylpiperidin-3-yl), and $R^4$ is chloro; or $R^1$ is methyl or ethyl, $R^2$ is methyl or ethyl, $R^3$ is 6,6-dimethylpiperidin-3-yl (e.g., (3S)-6,6-dimethylpiperidin-3-yl), and $R^4$ is chloro. In more specific embodiments, $R^1$ is methyl, $R^2$ is ethyl, $R^3$ is 5-methylpiperidin-3-yl (e.g., (3S,5S)-5-methylpiperidin-3-yl) and $R^4$ is chloro; $R^1$ is methyl, $R^2$ is ethyl, $R^3$ is 5,5-dimethylpiperidin-3-yl (e.g., (3S)-5,5-dimethylpiperidin-3-yl) and $R^4$ is chloro; $R^1$ is methyl, $R^2$ is ethyl, $R^3$ is 6-methylpiperidin-3-yl (e.g., (3S,6S)-6-methylpiperidin-3- yl) and R⁴ is chloro; or R¹ is methyl, R² is ethyl, R³ is 6,6-dimethylpiperidin-3-yl (e.g., (3S)-6,6-dimethylpiperidin-3-yl), and R⁴ is chloro. In more specific embodiments, R¹ and R² are simultaneously methyl, R³ is 5-methylpiperidin-3-yl (e.g., (3S,5S)-5-methylpiperidin-3-yl), and R⁴ is chloro; R¹ and R² are simultaneously methyl, R³ is 5,5-dimethylpiperidin-3-yl (e.g., (3S)-5,5-dimethylpiperidin-3-yl), and R⁴ is chloro; R¹ and R² are simultaneously methyl, R³ is 6-methylpiperidin-3-yl (e.g., (3S,6S)-6-methylpiperidin-3-yl), and R⁴ is chloro; or R¹ and R² are simultaneously methyl, R³ is 6,6-dimethylpiperidin-3-yl (e.g., (3S)-6,6-dimethylpiperidin-3-yl), and R⁴ is chloro. In more specific embodiments, R¹ and R² are simultaneously ethyl, R³ is 5-methylpiperidin (e.g., (3S,5S)-5-methylpiperidin-3-yl), and R⁴ is chloro; R¹ and R² are simultaneously ethyl, R³ is 5,5-dimethylpiperidin-3-yl (e.g., (3S)-5,5-dimethylpiperidin-3-yl), and R⁴ is chloro; R¹ and R² are simultaneously ethyl, R³ is 6-methylpiperidin-3-yl (e.g., (3S,6S)-6-methylpiperidin-3-yl), and R⁴ is chloro; or R¹ and R² are simultaneously ethyl, R³ is 6,6-dimethylpiperidin-3-yl (e.g., (3S)-6,6-dimethylpiperidin-3-yl), and R⁴ is chloro.

Pharmaceutically acceptable salts of a compound described herein or a solvate, stereoisomer, tautomer, or isotopic form of the salts (or any other specified form described herein), include those derived from suitable inorganic and organic acids and bases. That is, the invention encompasses salt forms of a compound of structural Formula (I), I(a) or species thereof as well as salt forms of a solvate, stereoisomer, tautomer, or isotopic form thereof. Examples of pharmaceutically acceptable, acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods known in the art, such as ion exchange. Other pharmaceutically acceptable salts include adipate, alginate, ascorbate, aspartate, benzenesulfonate, benzoate, besylate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, and valerate salts.

The salt of any compound described herein can also be derived from appropriate bases including alkali metal, alkaline earth metal, ammonium and N⁺(C₁₋₄alkyl)₄ salts. Representative alkali or alkaline earth metal salts include sodium, lithium, potassium, calcium, and magnesium. Other pharmaceutically acceptable salts include, when appropriate, ammonium, quaternary ammonium, and amine cations formed using counterions such as halide, hydroxide, carboxylate, sulfate, phosphate, nitrate, lower alkyl sulfonate and aryl sulfonate.

A compound of the present invention, or a specified form as described herein (e.g., a pharmaceutically acceptable salt, solvate, stereoisomer, tautomer, or isotropic form), may have one or more of the following properties: (1) at least or about 25-fold (e.g., at least or about 50-fold, 100-fold, 200-fold, 300-fold, or 400-fold) greater specificity for CDK7 than for each of CDK2, CDK9 and CDK12 in an enzymatic assay in terms of $K_i$; (2) at least or about 200-fold (e.g., at least or about 300-fold, 400-fold, or 500-fold) greater specificity for CDK7 than for each of CDK2, CDK9 and CDK12 in an enzymatic assay in terms of $IC_{50}$; (3) less than 150 pM (e.g., less than 120 pM, 110 pM, or 100 pM) $K_d$ binding to a CDK7/cyclin H complex as measured by surface plasmon resonance (SPR); and (4) an $EC_{50}$ of less than 10 nM (e.g., less than 5 nM, 4 nM, 3 nM, 2 nM or 1 nM) in an anti-proliferation assay using HCC70 cells. These properties render a compound or a specified form thereof particularly useful in therapies that require strong and specific inhibition of CDK7 without concomitant inhibition of other CDKs, particularly CDK2, CDK9 and CDK12.

Pharmaceutical Compositions and Kits: The present invention provides pharmaceutical compositions that include a compound of Formula (I), (Ia), a species thereof, or a specified form as described herein (e.g., a pharmaceutically acceptable salt, solvate (e.g., hydrate), stereoisomer, tautomer, or isotopic form thereof) and, optionally, a pharmaceutically acceptable carrier. In certain embodiments, the pharmaceutical composition includes: a compound of Formula (I) or (Ia), or a species thereof, or a pharmaceutically acceptable salt thereof; a compound of Formula (I) or (Ia), or a species thereof, in the form of a solvate (e.g., a hydrate); a compound of Formula (I) or (Ia), or a species thereof, in a stereoisomeric form or a mixture thereof (e.g., where the stereoisomer is an enantiomer or a racemic mixture thereof); a compound of Formula (I) or (Ia), or a species thereof, in the form of a tautomer; or any of the foregoing in an isotopic form. As noted, a pharmaceutical composition can include one or more pharmaceutically acceptable carriers, and the active agent/ingredient (i.e., compound, regardless of form) can be provided therein in an effective amount (e.g., a therapeutically effective amount or a prophylactically effective amount). In case of any doubt, any of the specified forms of a compound of Formula (I), (Ia), or a species thereof can be included in a pharmaceutical composition of the invention.

Pharmaceutical compositions of the invention can be prepared by relevant methods known in the art of pharmacology. In general, such preparatory methods include the steps of bringing a compound described herein, including compounds of Formula (I), (Ia), a species thereof, or a specified form thereof (e.g., a pharmaceutically acceptable salt, solvate, stereoisomer, tautomer, or isotopic form thereof) into association with a carrier and/or one or more other active ingredients (e.g., one or more of the second agents described herein) and/or accessory ingredients, and then, if necessary and/or desirable, shaping and/or packaging the product into a desired single-dose or multi-dose unit (e.g., for oral dosing). The accessory ingredient may improve the bioavailability of a compound of Formula (I), (Ia), a species thereof, or a specified form thereof, may reduce and/or modify its metabolism, may inhibit its excretion, and/or may modify its distribution within the body (e.g., by targeting a diseased tissue (e.g., a tumor). The pharmaceutical compositions can be packaged in various ways, including in bulk containers and as single unit doses (containing, e.g., discrete, predetermined amounts of the active agent) or a plurality thereof, and any such packaged or divided dosage forms are within the scope of the present invention. The amount of the active ingredient can be equal to the amount constituting a unit dosage or a convenient fraction of a dosage such as, for example, one-half or one-third of a dose.

Relative amounts of the active agent/ingredient, the pharmaceutically acceptable carrier(s), and/or any additional ingredients in a pharmaceutical composition of the invention can vary, depending upon the identity, size, and/or condition of the subject treated and further depending upon the route by which the composition is to be administered and the disease to be treated. By way of example, the composition may comprise between about 0.1% and 99.9% (w/w or w/v) of an active agent/ingredient.

Pharmaceutically acceptable carriers useful in the manufacture of the pharmaceutical compositions described herein are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable carriers useful in the manufacture of the pharmaceutical compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutical compositions of the present invention may be administered orally and oral formulations are within the scope of the present invention. Such orally acceptable dosage forms may be solid (e.g., a capsule, tablet, sachet, powder, granule, and orally dispersible film) or liquid (e.g., an ampoule, semi-solid, syrup, suspension, or solution (e.g., aqueous suspensions or dispersions and solutions). In the case of tablets, carriers commonly used include lactose and corn starch. Lubricating agents, such as magnesium stearate, can also be included. In the case of capsules, useful diluents include lactose and dried cornstarch. When aqueous suspensions are formulated, the active agent/ingredient can be combined with emulsifying and suspending agents. In any oral formulation, sweetening, flavoring or coloring agents may also be added. In any of the various embodiments described herein, an oral formulation can be formulated for immediate release or sustained/delayed release and may be coated or uncoated. A provided composition can also be in a micro-encapsulated form.

Compositions suitable for buccal or sublingual administration include tablets, lozenges and pastilles. Formulations can also be prepared for subcutaneous, intravenous, intramuscular, intraocular, intravitreal, intra-articular, intra-synovial, intrasternal, intrathecal, intrahepatic, intraperitoneal intralesional and by intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Although the descriptions of pharmaceutical compositions provided herein are principally directed to pharmaceutical compositions which are suitable for administration to humans, it will be understood by one of ordinary skill in the art that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification.

Compounds described herein are typically formulated in dosage unit form, e.g., single unit dosage form, for ease of administration and uniformity of dosage. The specific therapeutically or prophylactically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount can vary from subject to subject, depending, for example, on species, age, and general condition of a subject, severity of the side effects, disease to be treated, identity of the particular compound(s) to be administered, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day (e.g., once) to a 70 kg adult human may comprise about 1-100 mg, about 1-50 mg, about 1-35 mg (e.g., about 1-5, 1-10, 1-15, 1-20, 1-25, or 1-30 mg), about 2-20 mg, about 3-15 mg or about 10-30 mg (e.g., 10-20 or 10-25 mg). Here, and wherever ranges are referenced, the end points are included. The dosages provided in this disclosure can be scaled for patients of differing weights or body surface and may be expressed per $m^2$ of the patient's body surface.

In certain embodiments, compositions of the invention may be administered once per day. The dosage of a compound of Formula I or a subgenus or species thereof or a specified form thereof (e.g., a salt thereof) can be about 1-100 mg, about 1-50 mg, about 1-25 mg, about 2-20 mg, about 5-15 mg, about 10-15 mg, or about 13-14 mg.

In certain embodiments, a composition of the invention may be administered twice per day. In some embodiments, the dosage of a compound of Formula I or a subgenus or species thereof for each administration is about 0.5 mg to about 50 mg, about 0.5 mg to about 25 mg, about 0.5 mg to about 1 mg, about 1 mg to about 10 mg, about 1 mg to about 5 mg, about 3 mg to about 5 mg, or about 4 mg to about 5 mg.

Dose ranges as described herein provide guidance for the administration of provided pharmaceutical compositions to an adult. The amount to be administered to, for example, a child or an adolescent can be determined by one of ordinary skill in the art and can be lower or the same as that administered to an adult.

A compound or other composition described herein (e.g., a pharmaceutical composition) can be administered in a combination therapy (e.g., as defined and further described herein). The additional/second agent employed in a combiation therapy (and, where present, the third agent) is most likely to achieve a desired effect for the same disorder (e.g., the same cancer), however it may achieve different effects that aid the patient. Accordingly, the invention features pharmaceutical compositions containing a compound of Formula (I), (Ia), a species thereof, or a specified form thereof (e.g., a pharmaceutically acceptable salt), in a therapeutically effect amount; one or more additional agents, including any of the additional/second agents described herein; and a pharmaceutically acceptable carrier. The second/additional agent can be selected from a Bcl-2 inhibitor such as venetoclax, a PARP inhibitor such as olaparib or niraparib, a platinum-based anti-cancer agent such as carboplatin, cisplatin, or oxaliplatin, a taxane such as docetaxel or paclitaxel (or paclitaxel protein-bound (available as Abraxane®)), a CDK4/6 inhibitor such as palbociclib, ribociclib, abemaciclib, or trilaciclib, a selective estrogen receptor modulator (SERM) such as tamoxifen (available under the brand names Nolvadex™ and Soltamox™), raloxifene (available under the brand name Evista™), and toremifene (available as Fareston™), and a selective estrogen receptor degrader such as fulvestrant (available as Faslodex™), each in a therapeutically effective amount.

Methods of Treatment and Use: A compound of Formula (I), (Ia), a species thereof, or a specified form thereof (e.g., a salt, solvate, stereoisomer, tautomer, or isotopic form thereof) and other compositions described herein (e.g., pharmaceutical compositions, including those formulated in unit dosage forms) have a variety of uses, including in research and/or in clinical settings (e.g., in prophylactic or therapeutic methods). In some embodiments, the compounds and other compositions described herein (e.g., pharmaceutical compositions and kits) are configured for and used in preventing or treating a proliferative disease (e.g., a cancer, benign neoplasm, or pathologic angiogenesis) in a patient in need thereof. The cancer can be selected from among those disclosed herein (e.g., a blood cancer, a cancer characterized by the presence of a solid tumor in the breast, GI tract (e.g., a CRC), lung (e.g., NSCLC), pancreas, or prostate, or Ewing's sarcoma). In any embodiment of the methods of the invention, one may obtain information by carrying out or procuring the results of tests that characterize the type or grade of cancer afflicting the patient. For example, the methods and uses described herein can be applied to a patient who has been determined to have a "high grade" cancer (e.g., high grade serous ovarian cancer); determined to have tumor cells that exhibit a certain phenotype (e.g., to have breast cancer cells that are estrogen receptor-positive (ER+) or "triple negative"); and/or determined to have become resistant to treatment with a previously administered therapeutic agent (e.g., a chemotherapeutic agent such as another CDK inhibitor (e.g., palbociclib) or a receptor-degrading agent (e.g., fulvestrant)). The methods and uses described herein can include a step to make the determinations just mentioned; a step of determining whether a patient has a high-grade cancer, tumor cells of a specified phenotype, or has developed resistance to a previously administered therapeutic agent. The methods of treatment require administering to a patient in need thereof a therapeutically effective amount of a compound described herein (e.g., a compound having the structure depicted in Formula I or a subgenus or species thereof, in a form specified herein (e.g., as a salt or mixture of enantiomers) in a pharmaceutically acceptable composition to reduce a sign or symptom of the disease).

Each therapeutic or prophylactic method that employs a compound of Formula (I), (Ia), a species thereof, or a specified form thereof, or other composition described herein (e.g., a pharmaceutical composition) and involves administration of the compound or composition to a patient may also be expressed in terms of "use" and vice versa. For example, the invention encompasses the use of a compound described herein, in any specified form, or the use of a composition described herein for: the treatment of a disease described herein (e.g., a proliferative disease such as cancer (e.g., any blood/hematological cancer described herein or a solid tumor in, e.g., the breast, GI tract (e.g., CRC), lung (e.g., NSCLC), pancreas, or prostate)); the treatment of an inflammatory disease, autoimmune disease, or autoinflammatory disease, including any one or more of the specific diseases set out herein within the definitions of these types of diseases); the preparation a medicament for treating a disease described herein (e.g., a proliferative disease such as cancer, or an inflammatory, autoimmune, or autoinflammatory disease).

The methods of the invention that concern treating a disease described herein (e.g., a proliferative disease such as cancer (e.g., a blood cancer, breast cancer, GI tract cancer (e.g., a CRC), lung cancer (e.g., NSCLC), pancreatic cancer, prostate cancer, or Ewing's sarcoma) may specifically exclude any one or more of the types of diseases (e.g., any one or more of the types of cancer) described herein. For example, the invention features methods of treating cancer by administering a compound of Formula (I), (Ia), a species thereof, or a specified form thereof) with the proviso that the cancer is not a breast cancer; with the proviso that the cancer is not a breast cancer or a blood cancer (e.g., leukemia); with the proviso that the cancer is not a breast cancer, a blood cancer (e.g., leukemia), or an ovarian cancer; and so forth, with exclusions selected from any of the diseases/cancer types listed herein and with the same notion of variable exclusion from lists of elements relevant to other aspects and embodiments of the invention (e.g., chemical substituents of a compound described herein or components of kits and pharmaceutical compositions). Thus, where elements are presented as lists (e.g., in Markush group format), every possible subgroup of the elements is also disclosed, and any element(s) can be removed from the group.

In various embodiments, the subject being treated is: a mammal; a human; a domesticated or companion animal, such as a dog, cat, cow, pig, horse, sheep, or goat; a zoo animal; or a research animal such as a rodent, dog, non-human primate (e.g. a cynomolgus monkey or rhesus monkey), or non-human transgenic animal such as a transgenic mouse or transgenic pig. Where the patient is a human, the human may be a male, female, or transgendered person of any age group (e.g., a pediatric patient (e.g., an infant, child, or adolescent) or an adult patient (e.g., a young adult, middle-aged adult, or senior adult)). Similarly, where the patient is a non-human animal (e.g., a mammal), it may be a male or female of any age or developmental stage. Birds, particularly those having commercial value, are also suitable patients.

The proliferative disease to be treated or prevented using the compounds of Formula I or a subgenus or species thereof in any specified form can be associated with aberrant activity of CDK7. Aberrant activity of CDK7 may be an elevated and/or an inappropriate (e.g., abnormal) activity of CDK7. In certain embodiments, CDK7 is not overexpressed, and the activity of CDK7 is elevated and/or inappropriate (e.g., the CDK7 is a mutant CDK7 with increased activity, additional unwanted activity, resistance to native activity modulation, resistance to degradation, etc., as compared to wild-type CDK7). In certain other embodiments, CDK7 is overexpressed (at the mRNA and/or protein level), and the activity of CDK7 is elevated and/or inappropriate. The compounds of Formula (I), (Ia), or of a subgenus or species thereof, and pharmaceutically acceptable salts, solvates, stereoisomers, tautomers, isotopic forms, and compositions as described herein (i.e., compositions containing one or more of the foregoing), may inhibit the activity of CDK7 and be useful in treating and/or preventing proliferative diseases, including those described herein.

A proliferative disease may also be associated with inhibition of apoptosis of a cell in a biological sample or subject. Although the invention is not limited by any underlying mechanism of action, inhibiting the activity of CDK7 is expected to cause cytotoxicity via induction of apoptosis. The compositions of the invention may induce apoptosis, and therefore, be useful in treating and/or preventing proliferative diseases, particularly proliferative diseases in which CDK7 is overexpressed or overly active.

As noted, in certain embodiments, the proliferative disease to be treated or prevented using a composition of the invention is cancer. All types of cancers disclosed herein or known in the art are contemplated as being within the scope of the invention, but particularly those that are known to be associated with CDK7 activity (e.g., overactivity, overexpression, or misexpression).

In certain embodiments, the proliferative disease is a blood cancer, which may also be referred to as a hematopoietic or hematological cancer or malignancy. More specifically and in various embodiments, the blood cancer can be a leukemia such as acute lymphocytic leukemia (ALL; e.g., B cell ALL or T cell ALL), acute myelocytic leukemia (AML; e.g., B cell AML or T cell AML), chronic myelocytic leukemia (CML; e.g., B cell CML or T cell CML), chronic lymphocytic leukemia (CLL; e.g., B cell CLL (e.g., hairy cell leukemia) or T cell CLL), chronic neutrophilic leukemia (CNL), or chronic myelomonocytic leukemia (CMML). The blood cancer can also be a lymphoma such as Hodgkin lymphoma (HL; e.g., B cell HL or T cell HL), non-Hodgkin lymphoma (NHL, which can be deemed aggressive; e.g., B cell NHL or T cell NHL), follicular lymphoma (FL), chronic lymphocytic leukemia/small lymphocytic lymphoma (CLL/SLL), mantle cell lymphoma (MCL), a marginal zone lymphoma (MZL), such as a B cell lymphoma (e.g., splenic marginal zone B cell lymphoma), primary mediastinal B cell lymphoma (e.g., splenic marginal zone B cell lymphoma), primary mediastinal B cell lymphoma, Burkitt lymphoma (BL), lymphoplasmacytic lymphoma (i.e., Waldenstrom's macroglobulinemia), immunoblastic large cell lymphoma, precursor B lymphoblastic lymphoma, or primary central nervous system (CNS) lymphoma. The B cell NHL can be diffuse large cell lymphoma (DLCL; e.g., diffuse large B cell lymphoma (DLBCL; e.g., germinal center B cell-like (GCB) DLBCL or activated B-cell like (ABC) DLBCL)), and the T cell NHL can be precursor T lymphoblastic lymphoma or a peripheral T cell lymphoma (PTCL). In turn, the PTCL can be a cutaneous T cell lymphoma (CTCL) such as mycosis fungoides or Sezary syndrome, angioimmunoblastic T cell lymphoma, extranodal natural killer T cell lymphoma, enteropathy type T cell lymphoma, subcutaneous anniculitis-like T cell lymphoma, or anaplastic large cell lymphoma. While the invention is not limited to treating or preventing blood cancers having any particular cause or presentation, stem cells within the bone marrow may proliferate, thereby becoming a dominant cell type within the bone marrow and a target for a compound described herein. Leukemic cells can accumulate in the blood and infiltrate organs such as the lymph nodes, spleen, liver, and kidney. In some embodiments, a compound of the present disclosure or a specified form thereof is useful in the treatment or prevention of a leukemia or lymphoma.

In other embodiments, the proliferative disease is characterized by a solid tumor considered to be either of its primary location or metastatic. For example, in various embodiments, the cancer or tumor treated or prevented as described herein is an acoustic neuroma; adenocarcinoma; adrenal gland cancer; anal cancer; angiosarcoma (e.g., lymphangiosarcoma, lymphangio-endotheliosarcoma, hemangiosarcoma); appendix cancer; benign monoclonal gammopathy (also known as monoclonal gammopathy of unknown significance (MGUS); biliary cancer (e.g., cholangiocarcinoma); bladder cancer; breast cancer (e.g., adenocarcinoma of the breast, papillary carcinoma of the breast, mammary cancer, medullary carcinoma of the breast; any of which may be present in subjects having a particular profile, such as an HR+(ER+ or PR+), HER2+, HR− (having neither estrogen nor progesterone receptors), a triple negative breast cancer (TNBC; ER−/PR−/HER2−), or a triple-positive breast cancer (ER+/PR+/HER2+); a brain cancer (e.g., meningioma, glioblastoma, glioma (e.g., astrocytoma, oligodendroglioma), medulloblastoma); bronchus cancer; carcinoid tumor, which may be benign; cervical cancer (e.g., cervical adenocarcinoma); choriocarcinoma; chordoma; craniopharyngioma; a cancer present in the large intestine, such as colorectal cancer (CRC, e.g., colon cancer, rectal cancer, or colorectal adenocarcinoma); connective tissue cancer; epithelial carcinoma; ependymoma; endothelio-sarcoma (e.g., Kaposi's sarcoma or multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma (or other pediatric sarcoma, such as embryonal rhabdomyosarcoma or alveolar rhabdomyosarcoma); eye cancer (e.g., intraocular melanoma, retinoblastoma); familiar hypereosinophilia; gallbladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma, squamous cell carcinoma, or large cell carcinoma of the lung); leiomyosarcoma (LMS); mastocytosis (e.g., systemic mastocytosis); mouth cancer; muscle cancer; myelodys-plastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma, HGSOC, LGSOC, epithelial ovarian cancer (e.g., ovarian clear cell carcinoma or mucinous carcinoa), sex cord stromal tumors (granulosa cell), and endometroid tumors); papillary adenocarcinoma; pancreatic cancer (whether an exocrine tumor (e.g., pancreatic adenocarcinoma, pancreatic ductal adenocarcinoma (PDAC)), intraductal papillary mucinous neoplasm (IPMN), or a neuroendocrine tumor (e.g., PNETs or islet cell tumors); penile cancer (e.g., Paget's disease of the penis and scrotum); pinealoma; primary peritoneal cancer, primitive neuroectodermal tumor (PNT); plasma cell neoplasia; paraneoplastic syndromes; prostate cancer, which may be castration-resistant (e.g., prostate adenocarcinoma); rhabdomyosarcoma; salivary gland cancer; skin cancer (e.g., squamous cell carcinoma (SCC), keratoacanthoma (KA), melanoma, basal cell carcinoma (BCC)); small bowel or small intestine cancer; soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). We use the term "gastrointestinal (GI) tract cancer" to refer to a cancer present anywhere in the GI tract, including cancers of the mouth, throat, esophagus, stomach, large or small intestine, rectum, and anus. In some embodiments, the proliferative disease is associated with pathologic angiogenesis, and the methods of the invention and uses of a compound described herein (or any specified form thereof) encompass inhibiting pathologic angiogenesis in the context of cancer treatment (e.g., of a blood cancer or solid tumor). As noted above, the cancer can be a neuroendocrine cancer, and such tumors can be treated as described herein regardless of the organ in which they present.

In certain embodiments, the proliferative disease is an inflammatory disease. All types of inflammatory diseases disclosed herein (see the definition above) or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein (see the definition above) or known in the art are contemplated as being within the scope of the invention. In some embodiments, the disease is an autoimmune disease (see the definition of autoimmune disease above). All types of autoimmune diseases disclosed herein or known in the art are contemplated as being within the scope of the invention.

The therapeutic or prophylactic methods and "uses" described herein can include a step of administering one or more additional therapeutically active agents (i.e., a "second" agent that is distinct from a compound or other composition of the invention (e.g., a specified form of a compound described herein)) in combination with a composition of the invention (e.g., a compound of Formula (I), (Ia), a species thereof, or a pharmaceutically acceptable salt, solvate, stereoisomer, tautomer, or isotopic form thereof, or a composition containing such a compound or a specified form thereof (e.g., a pharmaceutically acceptable salt thereof, optionally in an isomeric form). We may refer to such methods and uses as "combination therapies," and we reiterate that any compound described herein or any specified form thereof can be the "first" therapeutically active agent administered or in use in a combination therapy; the designations "first" and "second" provide a convenient way to refer to two distinct agents without limiting the order or manner in which the first and second agents are administered. Thus, a patient may receive one or more of the second agents described herein prior to receiving a compound of the invention. In fact, and as noted, a patient may have a cancer that has become refractory to the second agent prior to administration of a compound of the invention. For example, a compound or pharmaceutical composition of the invention can be used or administered to treat a patient who has become or is at risk of becoming resistant to treatment with a CDK4/6 inhibitor when used alone or in combination with one or more of an aromatase inhibitor, a selective estrogen receptor modulator or a selective estrogen receptor degrader.

Second agents include, but are not limited to, anti-proliferative agents, anti-cancer agents, anti-diabetic agents, anti-inflammatory agents, immunosuppressant agents, and pain-relieving agents. The second agents may, but do not necessarily, synergistically augment inhibition of CDK7 induced by the compounds or compositions of this invention (i.e., the "first" agent) in the biological sample or subject. The combination of the first and second agent(s) may be useful in treating proliferative diseases resistant to a treatment using the second agent(s) without the first agent(s). In this event, and as noted above, a compound of the invention or a specified form thereof, or a composition of the invention (e.g., a pharmaceutical composition described herein) can be administered after the patient has been determined to have become resistant to a previously administered therapeutic agent. One of ordinary skill in the medical arts will understand the phenomenon of resistant cancer, in which a patient's cancer does not respond to treatment at either the beginning of treatment or during treatment. A resistant cancer may also be called refractory, and any treatment method or use described herein may be applied to a resistant or refractory cancer (e.g., a blood cancer, including any of the types described above, or a proliferative disease characterized by a solid tumor, including any cancer selected from those listed above (e.g., an acoustic neuroma, adenocarcinoma, adrenal gland cancer, etc., and in case of any doubt includes a cancer of the breast, intestine, lung, pancreas, prostate, and Ewing's sarcoma)). Accordingly, the methods of treating a patient as described herein can include the step of identifying or selecting a patient having a cancer that is resistant or refractory to treatment with a prior therapeutic agent, including any of those described herein as an additional/second agent, and a compound of the invention, any specified form thereof, and pharmaceutical compositions containing such a compound or any specified form thereof have utility/use in treating such patients. CDK7 over-expression has been associated with hormone-receptor positive breast cancer ($HR^+$ breast cancer), triple-negative breast cancer (TNBC), acute myelogenous luekemia (AML), small cell lung cancer (SCLC, e.g., neuroendocrine SCLC (NE SCLC)), esophageal squamous cell carcinoma, neuroblastoma, high grade gliomas, ovarian cancer, solid tumors, and other hematological malignancies. Accordingly, in the methods of treatment described herein, the patient can have any of these types of cancer, and the compounds of the invention, any specified form thereof, and pharmaceutical compositions containing them find utility/use in treating such patients.

In combination therapies of the invention, the compound of Formula (I), (Ia), a species thereof, or a specified form as described herein (e.g., a pharmaceutically acceptable salt, solvate, stereoisomer, tautomer, or isotopic form thereof) can be administered concurrently with, prior to, or subsequent to, the one or more additional (i.e., distinct) therapeutic agents. Each additional therapeutic agent may be administered at a dose and/or according to a dosing regimen determined for that particular agent (e.g., a dose or dosing regimen approved by a regulatory agency (e.g., the U.S. Food and Drug Administration (FDA) or agencies of similar purpose in other countries), which may be set out in the product insert accompanying the commercially-supplied agent). The additional therapeutic agents may also be administered together with each other and/or with a compound or composition described herein in a single dose or administered separately in different doses. The particular combination to employ in a regimen will take into account the compatibility of a compound of the invention with one or more of the additional/second therapeutic agents and/or the desired therapeutic and/or prophylactic effect to be achieved. In general, it is expected that the additional/second therapeutic agents utilized in combination will be utilized at levels that do not exceed the levels at which they are utilized individually. Thus, in some embodiments, the levels utilized in combination will be lower than those utilized individually.

The second agent can be, but is not limited to, an anti-proliferative agent, an anti-cancer agent, an anti-diabetic agent, an anti-inflammatory agent, an immunosuppressant agent, or a pain-relieving agent. Such therapeutic agents include small organic molecules such as drug compounds (e.g., compounds approved by the FDA or the European Medicines Agency), polypeptides (including nucleoproteins, mucoproteins, glycoproteins, lipoproteins, and antibodies of any target-binding configuration, with the polypeptide being synthetic or naturally occurring), carbohydrates (e.g., mono-, oligo-, and polysaccharides), small molecules linked to proteins, steroids, nucleotides, nucleosides, and nucleic acids (e.g., DNAs and RNAs, including any RNA configured for RNAi, regardless of length (e.g., an antisense oligonucleotide or shRNA), lipids, vitamins, and cells (e.g., genetically modified cells (e.g., a genetically engineered immune cell suitable for CAR-T therapy) or cells administered as an allogeneic hematopoietic cell transplantation (HCT)).

In certain embodiments, the additional/second therapeutic agent is a Bcl-2 inhibitor such as APG-1252, APG-2575, BP1002 (prexigebersen), the antisense oligonucleotide known as oblimersen (G3139), S55746/BCL201, or venetoclax (e.g., venetoclax tablets marketed as Venclexta®); a CDK9 inhibitor such as alvocidib/DSP-2033/flavopiridol, AT7519, AZD5576, BAY1251152, BAY1143572, CYC065, nanoflavopiridol, NVP2, seliciclib (CYC202), TG02, TP-1287, VS2-370 or voruciclib (formerly P1446A-05); a hormone receptor (e.g., estrogen receptor) degradation agent, such as fulvestrant (e.g., marketed as Faslodex® and others); a Flt3 (FMS-like tyrosine kinase 3) inhibitor such as CDX-301, CG'806, CT053PTSA, crenolanib (e.g., crenolanib besylate), ENMD-2076, FF-10101-01, FLYSYN, gilteritinib (ASP2215), HM43239, lestautinib, ponatinib (e.g., marketed as Iclusig®, previously AP24534), NMS-088, sorafenib (e.g., marketed as Nexavar®), sunitinib, pacritinib, pexidartinib/PLX3397, quizartinib, midostaurin (e.g., marketed as Rydapt®), SEL24, SKI-G-801, or SKLB1028; a PARP inhibitor such as olaparib (e.g., marketed as Lynparza®), rucaparib (e.g., marketed as Rubraca®), talazoparib (e.g., marketed as Talzenna®), veliparib (ABT-888), or niraparib (e.g., marketed as Zejula®); a BET inhibitor such as ABBV-075, BAY-299, BAY-1238097, BMS-986158, CPI-0610, CPI-203, FT-1101, GS-5829, GSK-2820151, GSK-525762, I-BET151, I-BET762, INCB054329, JQ1, MS436, OTX015, PFI-1, PLX51107, RVX2135, TEN-010, ZEN-3694, or a compound disclosed in U.S. application Ser. No. 12/810,564 (now U.S. Pat. No. 8,476,260), which is hereby incorporated herein by reference in its entirety; a platinum-based therapeutic agent such as cisplatin, oxaliplatin (e.g., marketed as Eloxatin®), nedaplatin, carboplatin (e.g., marketed as Paraplatin®), phenanthriplatin, picoplatin, satraplatin (JM216), or triplatin tetranitrate; a CDK4/6 inhibitor such as BPI-1178, G1T38, palbociclib (e.g., marketed as Ibrance®), ribociclib (e.g., marketed as Kisqali®), ON 123300, trilaciclib, or abemaciclib (e.g., marketed as Verzenio®); a MEK inhibitor such as trametinib (e.g., marketed as Mekinist®), cobimetinib, or binemetinib; an inhibitor of the PI3K/AKT/mTOR pathway (e.g., gedatolisib); or a phosphoinositide 3-kinase (PI3 kinase) inhibitor, optionally of Class I (e.g., Class IA) and/or optionally directed against a specific PI3K isoform. The PI3K inhibitor can be apitolisib (GDC-0980), idelalisib (e.g., marketed as Zydelig®), copanlisib (e.g., marketed as Aligopa®), duvelisib (e.g., marketed as Copiktra®), pictilisib, alpelisib (e.g., marketed as Piqray®) or capecitabine.

In other embodiments, the additional/second agent can be capecitabine (e.g., marketed as Xeloda®). In other embodiments, the additional/second agent can be gemcitabine (combined with a compound of the invention to treat, e.g., TNBC, CRC, SCLC, or a pancreatic cancer (e.g., PDAC)). In other embodiments, the additional/second agent can be an antimetabolite, such as the pyrimidine analog 5-fluorouracil (5-FU), which may be used in combination with a compound of Formula (I), (Ia), a species thereof, or a specified form thereof, and one or more of leucovorin, methotrexate, or oxaliplatin. In other embodiments, the additional/second agent can be an aromatase inhibitor, such as exemestane or anastrasole.

APG-1252 is a dual Bcl-2/Bcl-xL inhibitor that has shown promise in early clinical trials when patients having SCLC or another solid tumor were dosed between 10-400 mg (e.g., 160 mg) intravenously twice weekly for three weeks in a 28-day cycle (see Lakhani et al., *J. Clin. Oncol.* 36:15_suppl, 2594, and ClinicalTrials.gov identifier NCT03080311). APG-2575 is a Bcl-2 selective inhibitor that has shown promise in preclinical studies of FL and DLBCL in combination with ibrutinib (see Fang et al., AACR Annual Meeting 2019, *Cancer Res.* 79(13 Suppl):Abstract No. 2058) and has begun clinical trials as a single-agent treatment for patients with blood cancers; in a dose escalation study, patients are given 20 mg, once daily, by mouth, for four consecutive weeks as one cycle. Escalations to 50, 100, 200, 400, 600 and 800 mg are planned to identify the MTD (see ClinicalTrials.gov identifier NCT03537482). BP1002 is an uncharged P-ethoxy antisense oligodeoxynucleotide targeted against Bcl-2 mRNA that may have fewer adverse effects than other antisense analogs and has shown promise in inhibiting the growth of human lymphoma cell lines inclubated with BP1002 for four days and of CJ cells (transformed FL cells) implanted into SCID mice (see Ashizawa et al., AACR Annual Meeting 2017, *Cancer Res.* 77(13 Suppl):Abstract No. 5091). BP1002 has also been administered in combination with cytarabine (LDAC) to patients having AML (see ClinicalTrials.gov identifier NCT04072458). S55746/BCL201 is an orally available, selective Bcl-2 inhibitor that, in mice, demonstrated antitumor efficacy in two blood cancer xenograft models (Casara et al., *Oncotarget* 9(28):20075-88, 2018). A phase I dose-escalation study was designed to administer film-coated tablets containing 50 or 100 mg of S55746, in doses up to 1500 mg, to patients with CLL or a B cell NHL including FL, MCL, DLBCL, SLL, MZL, and MM (see ClinicalTrials.gov identifier NCT02920697). Venetoclax tablets have been approved for treating adult patients with CLL or SLL and, in combination with azacytidine, or decitabine, or low-dose cytarabine, for treating newly-diagnosed AML in patients who are at least 75 years old or who have comorbidities that preclude the use of intensive induction chemotherapy. Dosing for CLL/SLL can follow the five-week ramp-up schedule and dosing for AML can follow the four-day ramp-up, both described in the product insert, together with other pertinent information (see also U.S. Pat. Nos. 8,546,399; 9,174,982; and 9,539,251, which are hereby incorporated by reference in their entireties). Alvocidib was studied in combination with cytarabine/mitoxantrone or cytarabine/daunorubicin in patients with AML, with the details of administration being available at ClinicalTrials.gov with the identifier NCT03563560 (see also Yeh et al., *Oncotarget* 6(5):2667-2679, 2015, Morales et al., *Cell Cycle* 15(4):519-527, 2016, and Zeidner et al., *Haematologica* 100(9):1172-1179, 2015). AT7519 has been administered in a dose escalation format to eligible patients having refractory solid tumors. While there was some evidence of clinical activity, the appearance of QTc prolongation precluded further development at the dose schedule described by Mahadevan et al. (*J Clin. Oncol.* ASCO Abstract No. 3533; see also Santo et al., *Oncogene* 29:2325-2336, 2010, describing the preclinical activity of AT7519 in MM). AZD5576 induced apoptosis in breast and lung cancer cell lines at the nanomolar level (see Li et al., *Bioorg. Med. Chem. Lett.* 27(15):3231-3237, 2017) and has been examined alone and in combination with acalabrutinib for the treatment of NHL (see AACR 2017 Abstract No. 4295). BAY1251152 was the subject of a phase I clinical trial to characterize the MTD in patients with advanced blood cancers; the agent was infused weekly in 21-day cycles (see ClinicalTrials.gov identifier NCT02745743; see also Luecking et al., AACR 2017 Abstract No. 984). Voruciclib is a clinical stage oral CDK9 inhibitor that represses MCL-1 and sensitizes high-risk DLBCL to BCL2 inhibition. Dey et al. (*Scientific Reports* 7:18007, 2017) suggest that the combination of voruciclib and venetoclax is promising for a subset of high-risk DLBCL patients (see also ClinicalTrials.gov identifier NCT03547115). Fulvestrant has been approved for administration to postmenopausal women with advanced hormone receptor (HR)-positive, HER2-negative breast cancer, with HR-positive metastatic breast cancer whose disease progressed after treatment with other anti-estrogen therapies, and in combination with palbociclib (Ibrance®). Fulvestrant is administered by intramuscular injection at 500 or 250 mg (the lower dose being recommended for patients with moderate hepatic impairment) on days 1, 15, and 29, and once monthly thereafter (see the product insert for additional information; see also U.S. Pat. Nos. 6,744,122; 7,456,160; 8,329,680; and 8,466,139, each of which are hereby incorporated by reference herein in their entireties). Ponatinib has been administered in clinical trials to patients with CML or ALL (see ClinicalTrials.gov identifiers NCT0066092072, NCT012074401973, NCT02467270, NCT03709017, NCT02448095, NCT03678454, and NCT02398825) as well as solid tumors, such as biliary cancer and NSCLC (NCT02265341, NCT02272998, NCT01813734, NCT02265341, NCT02272998, NCT01813734, NCT02265341, NCT02272998, NCT01813734, NCT01935336, NCT03171389, and NCT03704688; see also the review article by Tan et al., *Onco. Targets Ther.* 12:635-645, 2019). Additional information regarding the dosing regimen can be found in the product insert; see also U.S. Pat. Nos. 8,114,874; 9,029,533; and 9,493,470, each of which is hereby incorporated by reference herein in its entirety. Sorafenib has been approved for the treatment of kidney and liver cancers, AML, and radioactive iodine resistant advanced thyroid cancer, and a clinical trial was initiated in patients with desmoid-type fibromatosis (see ClinicalTrials.gov identifier NCT02066181). Information regarding dosage can be found in the product insert, which advises administration of two, 400 mg tablets twice daily; see also U.S. Pat. Nos. 7,235,576; 7,351,834; 7,897,623; 8,124,630; 8,618,141; 8,841,330; 8,877,933; and 9,737,488, each of which is hereby incorporated by reference herein in its entirety. Midostaurin has been administered to patients having AML, MDS, or systemic mastocytosis, and has been found to significantly prolong survival of FLT3-mutated AML patients when combined with conventional induction and consolidation therapies (see Stone et al., ASH 57th Annual Meeting, 2015 and Gallogly et al., *Ther. Adv. Hematol.* 8(9):245-251, 2017; clin see also the product insert, ClinicalTrials.gov identifier NCT03512197, and U.S. Pat. Nos. 7,973,031; 8,222,244; and 8,575,146, each of which is hereby incorporated by reference herein in its entirety. Alpelisib is a kinase inhibitor indicated in combination with fulvestrant for the treatment of postmenopausal women, and men, with HR+/HER2−/PIK3CA-mutated, advanced or metastatic breast cancer as detected by an FDA-approved test following progression on or after an endocrine-based regimen. The recommended dose is 300 mg (two 150 mg tablets) taken orally once daily with food, which, as for all chemotherapeutic agents, may be interrupted, reduced, or discontinued to manage adverse reactions. Paclitaxel is supplied as a nonaqueous solution intended for dilution with a suitable parenteral fluid prior to intravenous infusion. Under the brand name Taxol®, it is supplied in 30 mg, 100 mg, and 300 mg vials and can be used in a combination therapy described herein to treat a variety of cancers, including those of the bladder, breast, esophagus, fallopian tube or ovary, lung, skin (melanoma), and prostate. Palbociclib has been approved for use in HR+/HER2− advanced or metastatic breast cancer at a recommended dose of 125 mg daily, by mouth. It can be used with a compound of the invention either alone or in combination with an aromatase inhibitor or fulvestrant. The information provided here and publicly available can be used to practice the methods and uses of the invention. In case of doubt, the invention encompasses combination therapies that require a compound of the invention or a specified form thereof and any one or more additional/second agents, which may be administered at or below a dosage currently approved for single use (e.g., as described above), to a patient as described herein. Triplet combinations include a compound of Formula (I), (Ia), a species thereof, or a specified form thereof with: alpelisib and fulvestrant or alpelisib and a taxane (for, e.g., treating NSCLC).

In one embodiment, the method of treatment includes administering, to a patient who is suffering from a sarcoma (e.g., an osteosarcoma, rhabdomyosarcoma, or Ewing's sarcoma), a therapeutically effective amount of a compound described herein (e.g., a compound of Formula I or (Ia) (e.g., Compound 100, 101, or 102)) or a specified form thereof and a therapeutically effective amount of a PARP inhibitor (e.g., olaparib (e.g., marketed as Lynparza®), rucaparib (e.g., marketed as Rubraca®), talazoparib (e.g., marketed as Talzenna®), veliparib (ABT-888), or niraparib (e.g., marketed as Zejula®). Such "uses" are also within the scope of the present invention.

Also encompassed by the invention are kits (e.g., pharmaceutical packs). The kits may be used for preventing and/or treating any of the diseases set forth herein. The kits provided may comprise a pharmaceutical composition or compound of the present invention; and a container (e.g., a vial, ampule, bottle, syringe, and/or dispenser package, or other suitable container) for storing, reconstituting, and/or administering the compound or composition. In some embodiments, provided kits may optionally further include a second container comprising a pharmaceutical excipient for dilution or suspension of the pharmaceutical composition or compound of the invention. In some embodiments, the pharmaceutical composition or compound provided in the container and the second container are combined to form one unit dosage form. In some embodiments, provided kits may optionally further include a second or third container comprising an additional therapeutic agent to be administered in combination with the pharmaceutical composition or compound of the invention. The kit can also include any type of paraphernalia useful in administering the active agent(s) contained therein (e.g., tubing, syringes, needles, sterile dressings, tape, and the like). In certain embodiments, the kits are useful in preventing and/or treating a proliferative disease in a subject. In certain embodiments, the kits further include instructions for administering the compound, or a pharmaceutically acceptable salt, solvate, hydrate, tautomer, isotopically and labeled derivative thereof, or a pharmaceutical composition thereof, to a subject to prevent and/or treat a proliferative disease.

In yet another aspect, the present invention provides the compounds of Formula I or Formula Ia and pharmaceutically acceptable salts, solvates, and hydrates thereof for use in the treatment of a proliferative disease in a subject. In certain embodiments, provided by the invention are the compounds described herein, and pharmaceutically acceptable salts and compositions thereof, for use in the treatment of a proliferative disease in a subject. In certain embodiments, provided by the invention are the compounds described herein, and pharmaceutically acceptable salts and compositions thereof, for use in inhibiting cell growth. In certain embodiments, provided by the invention are the compounds described herein, and pharmaceutically acceptable salts and compositions thereof, for use in inducing apoptosis in a cell. In certain embodiments, provided by the invention are the compounds described herein, and pharmaceutically acceptable salts and compositions thereof, for use in inhibiting transcription.

EXAMPLES

The compounds described herein can be prepared from readily available starting materials and according to the synthetic protocols described below. Alternatively, one of ordinary skill in the art may readily modify the disclosed protocols. For example, it will be appreciated that where process conditions (e.g., reaction temperatures, reaction times, mole ratios of reactants, solvents, pressures, etc.) are given, other process conditions can also be used.

Additionally, and as will be apparent to one of ordinary skill in the art, protecting groups may be used to prevent certain functional groups from undergoing undesired reactions. The choice of a suitable protecting group for a particular functional group as well as suitable conditions for protection and deprotection are well known in the art. For example, numerous protecting groups and guidance for their introduction and removal are disclosed by Greene et al. (*Protecting Groups in Organic Synthesis, Second Edition, Wiley, New York,* 1991, and references cited therein).

Example 1: Synthesis of Benzyl (2R, 5R)-5-amino-2-methyl-piperidine-1-carboxylate and benzyl (2S, 5S)-5-amino-2-methyl-piperidine-1-carboxylate Step 1: Benzyl 5-(tert-butoxycarbonylamino)-2-methyl-piperidine-1-carboxylate

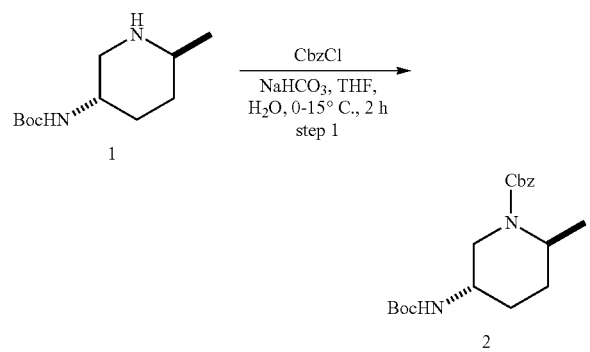

To a solution containing commercially available racemic trans tert-butyl N-(6-methyl-3-piperidyl)carbamate (5 g, 23.33 mmol, 1 eq,) and NaHCO$_3$ (13.72 g, 163.32 mmol, 7 eq) in tetrahydrofuran (THF; 50 mL) and H$_2$O (50 mL), we added CbzCl (5.97 g, 35.00 mmol, 4.98 mL, 1.5 eq) dropwise at 0° C. The mixture was stirred at 15° C. for 2 hours then poured into water (50 mL) and extracted with ethyl acetate (EtOAc; 50 mL×3). The combined organic layer was washed with brine (50 mL×3), dried over Na$_2$SO$_4$, and filtered. The filtrate was concentrated under reduced pressure, and the residue was purified by medium pressure liquid chromatography (MPLC; SiO$_2$, PE:EtOAc=5:1 to 1:1) to give the title compound as a yellow solid (9.7 g, 18.04 mmol, 77.32% yield, 64.8% purity).

Step 2: Benzyl (2R, 5R)-5-amino-2-methyl-piperidine-1-carboxylate and benzyl (2S, 5S)-5-amino-2-methyl-piperidine-1-carboxylate

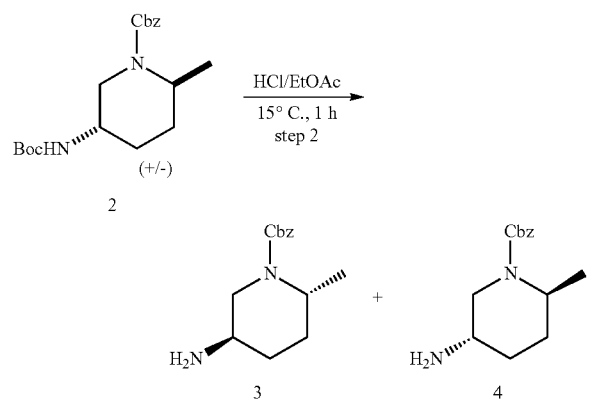

To a mixture of racemic trans benzyl 5-(tert-butoxycarbonylamino)-2-methyl-piperidine-1-carboxylate (9.7 g, 27.84 mmol, 1 eq) in EtOAc (100 mL) we added HCl/EtOAc (15 mL, 4 M), and the mixture was stirred at 15° C. for 1 hour. We then filtered the mixture and collected the filter cake. The solid was dissolved in methanol (MeOH; 15 mL)

and the pH was adjusted to 9 using a strongly acidic cation exchange resin (here, AMBERLYST® A21) before the mixture was filtered and the filtrate was concentrated. The residue was separated by supercritical fluid chromatography (SFC; column: marketed by Daicel as CHIRALCEL® (chemicals for use in chromatography) ODH (250 mm×30 mm, 5 μm); mobile phase: [0.1% $NH_3 \cdot H_2O$ MeOH]; B %: 28%-28%, 16 min) to afford title compound 1 (1.9 g, SFC: Rt=2.264 min, 93.2% ee, peak 1) and title compound 2 (1.9 g, SFC: Rt=2.593 min, 98.6% ee, peak 2), both as light yellow solids. Peak 1 is structure 3. Peak 2 is structure 4.

Example 2: Synthesis of 7-dimethylphosphoryl-3-[2-[[(3S, 6S)-6-methyl-3-piperidyl]amino]-5-(trifluoromethyl)pyrimidin-4-yl]-1H-indole-6-carbonitrile (Compound 100)

Step 1: Benzyl (2S, 5S)-5-[[4-(7-chloro-6-cyano-1H-indol-3-yl)-5-(trifluoromethyl)pyrimidin-2-yl]amino]-2-methyl-piperidine-1-carboxylate

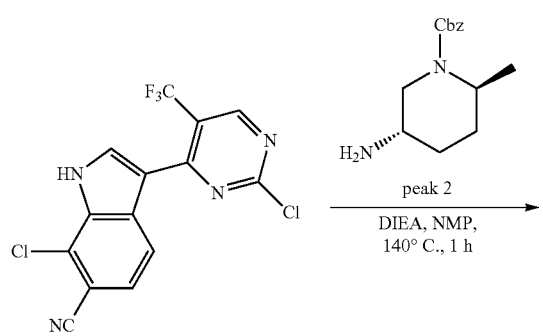

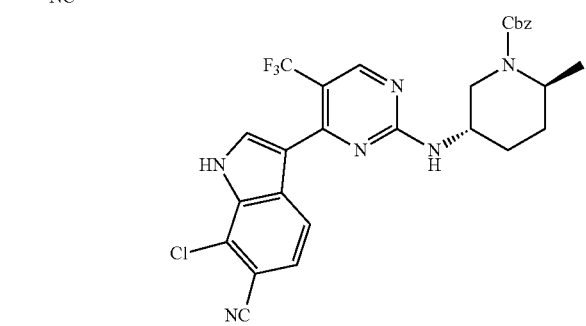

We stirred a mixture of 7-chloro-3-[2-chloro-5-(trifluoromethyl)pyrimidin-4-yl]-1H-indole-6-carbonitrile (0.81 g, 2.27 mmol, 1 eq), benzyl (2S,5S)-5-amino-2-methyl-piperidine-1-carboxylate (732.20 mg, 2.95 mmol, 1.3 eq) and N,N-diisopropylethylamine (DIEA or DIPEA; 879.41 mg, 6.80 mmol, 1.19 mL, 3 eq) in N-methyl-2-pyrrolidone (NMP; 8 mL) at 140° C. for 1 hour. The reaction mixture was diluted with $H_2O$ (100 mL) and extracted with EtOAc (50 mL×2). The combined organic layers were washed with brine (100 mL×2), dried over $Na_2SO_4$, filtered, and concentrated under reduced pressure to give a residue that was purified by column chromatography ($SiO_2$, petroleum ether/ethyl acetate=10:1 to 4:1) to afford title compound as a yellow solid (1.1 g).

Step 2: Benzyl (2S, 5S)-5-[[4-(6-cyano-7-dimethylphosphoryl-1H-indol-3-yl)-5-(trifluoromethyl)pyrimidin-2-yl]amino]-2-methyl-piperidine-1-carboxylate

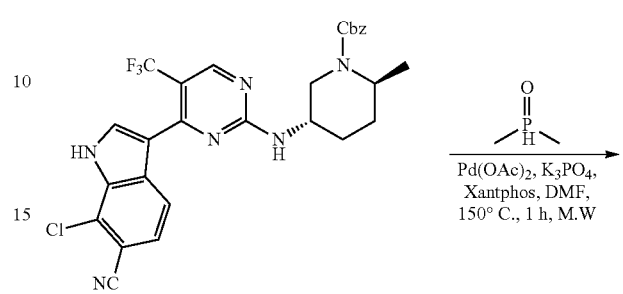

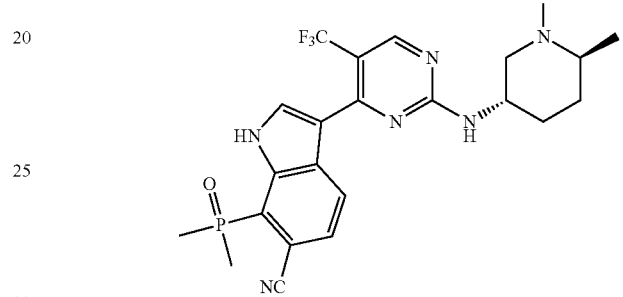

We prepared a mixture of benzyl (2S,5S)-5-[[4-(7-chloro-6-cyano-1H-indol-3-yl)-5-(trifluoromethyl) pyrimidin-2-yl]amino]-2-methyl-piperidine-1-carboxylate (1.05 g, 1.85 mmol, 1 eq), methylphosphonoylmethane (720.17 mg, 9.23 mmol, 5 eq), $K_3PO_4$ (783.45 mg, 3.69 mmol, 2 eq), $Pd(OAc)_2$ (41.43 mg, 184.54 μmol, 0.1 eq), xantphos ($C_{39}H_{32}OP_2$; 106.78 mg, 184.54 μmol, 0.1 eq) and dimethylformamide (DMF; 10 mL) in a microwave sealed tube, degassed it, and purged it with $N_2$ (×3). The mixture was then stirred at 150° C. for 1 hour in microwave. The reaction mixture was diluted with $H_2O$ (100 mL) and extracted with ethyl acetate (EtOAc; 50 mL×3). The combined organic layers were washed with brine (150 mL×2), dried over $Na_2SO_4$, filtered, and concentrated under reduced pressure to give a residue that we purified by column chromatography ($SiO_2$, petroleum ether/ethyl acetate=10:1 to 1:1) to afford the title compound as a yellow oil (490 mg).

Step 3: 7-dimethylphosphoryl-3-[2-[[(3S, 6S)-6-methyl-3-piperidyl]amino]-5-(trifluoromethyl)pyrimidin-4-yl]-1H-indole-6-carbonitrile

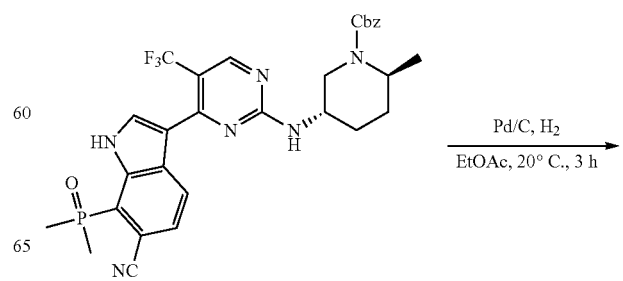

-continued

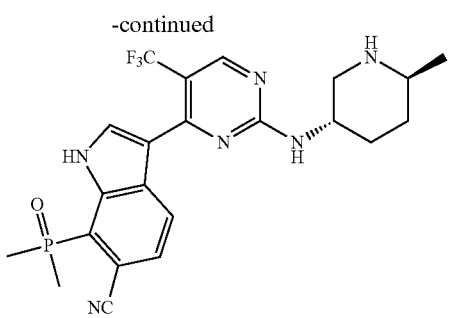

To a solution of benzyl(2S,5S)-5-[[4-(6-cyano-7-dimethylphosphoryl-1H-indol-3-yl)-5-(trifluoromethyl)pyrimidin-2-yl]amino]-2-methyl-piperidine-1-carboxylate (440 mg, 720.64 µmol, 1 eq) in EtOAc (5 mL), we added Pd/C (200 mg, 10% purity) under $N_2$. We degassed the suspension under vacuum, purged it with $H_2$ several times, then stirred the mixture under $H_2$ (15 psi) at 20° C. for 3 hours before filtering it. The filtrate was concentrated to give a residue we purified by prep-HPLC (high performance liquid chromatography; neutral condition) to yield the title compound as a white solid (142.2 mg).

The reaction was combined with another reaction in 50 mg scale for purification by liquid chromatography mass spectrometry (LCMS). LCMS: ET6034-1492-P1C: (M+H$^+$): 477.1 @2.572 (10-80% ACN (acetonitrile) in $H_2O$ 4.5 minutes). $^1$H NMR (400 MHz, DMSO (dimethylsulfoxide)-d6) δ 8.74 (br d, J=7.89 Hz, 1H), 8.65-8.44 (m, 2H), 8.17 (br d, J=15.35 Hz, 1H), 7.84 (br t, J=8.11 Hz, 1H), 7.67 (br t, J=7.02 Hz, 1H), 3.81 (br s, 1H), 3.10 (br d, J=11.40 Hz, 1H), 2.45-2.38 (m, 1H), 2.02 (d, J=13.59 Hz, 8H), 1.64 (br d, J=11.40 Hz, 1H), 1.49-1.34 (m, 1H), 1.11 (br d, J=10.96 Hz, 1H), 0.97 (br d, J=5.70 Hz, 3H)

Example 3: Synthesis of (S)-6,6-dimethylpiperidin-3-amine

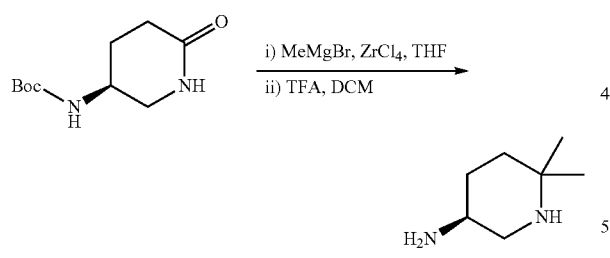

We dissolved (S)-tert-butyl (6-oxopiperidin-3-yl)carbamate (1.00 g, 4.67 mmol) (*Tetrahedron Letters*, 36:8205, 1995) in THF (47 mL) and cooled the solution to −10° C. Zirconium (IV) chloride (2.61 g, 11.22 mmol) was added, and the mixture was stirred for 30 minutes at this temperature. A methylmagnesium bromide solution (3M in ether, 20.25 mL, 60.75 mmol) was added, and the reaction mixture was allowed to slowly warm up to room temperature, at which it was stirred overnight. The solution was quenched with 30% aqueous NaOH, diluted with EtOAc, filtered, and then extracted 3 times with EtOAc. The organics were combined, dried over sodium sulfate, filtered, and concentrated in vacuo to provide the crude product as a yellow oil that was used without purification. The oil was dissolved in dichloromethane (DCM; 47 mL) and trifluoroacetic acid (TFA; 3.58 mL, 46.73 mmol) was added. We stirred the reaction mixture at room temperature for 16 hours, concentrated it in vacuo and co-evaporated it a few times with DCM to provide the crude title compound as a brown oil, which we used in the next step without further purification.

Example 4: Synthesis of (S)-7-(dimethylphosphoryl)-3-(2-((6,6-dimethylpiperidin-3-yl)amino)-5-(trifluoromethyl)pyrimidin-4-yl)-1H-indole-6-carbonitrile (Compound 101)

Step 1: 7-Bromo-1H-indole-6-carboxylic acid

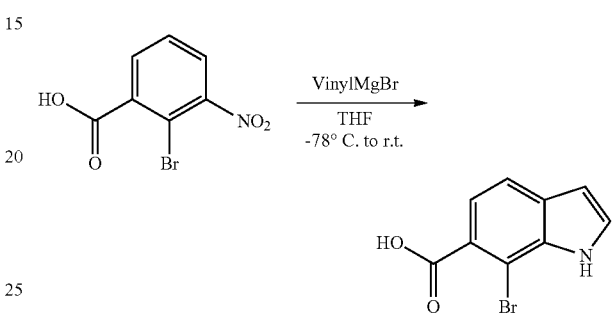

We stirred a solution of vinylmagnesium bromide (1.0 M in THF (159 mL, 159 mmol) at −78° C. and added to it, dropwise, over a period of 1 hour, a solution of 2-bromo-3-nitrobenzoic acid (10.0 g, 39.8 mmol) in THF (159 mL). The reaction mixture was allowed to reach room temperature and was stirred at that temperature overnight. The reaction mixture was then poured over saturated aqueous ammonium chloride (150 mL) and acidified to a pH 2, using aqueous 1M HCl. We extracted the crude product with EtOAc (3×200 mL), dried the extract over sodium sulfate, filtered it, and concentrated it in vacuo. The residue was then triturated in DCM (100 mL) and dried overnight with a flow of air to provide the title compound as a light brown solid (7.58 g, 31.58 mmol, 79% yield).

Step 2: 7-Bromo-1H-indole-6-carboxamide

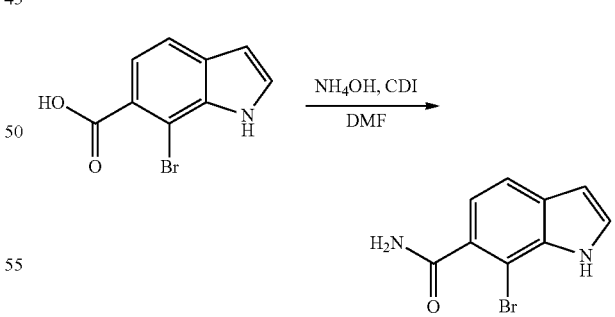

We stirred a solution of 7-bromo-1H-indole-6-carboxylic acid (6.58 g, 27.4 mmol) in DMF (54.8 mL) at 0° C. and added 1,1'-carbonyldiimidazole (CDI; 8.89 g, 54.8 mmol) to it portion wise. The mixture was stirred for 5 minutes, and the intermediate was observed by LCMS. We then added NH$_4$OH (39.5 mL, 274 mmol) at 0° C., and the solution was stirred for 5 minutes. The reaction was quenched with saturated aqueous ammonium chloride (25 mL) and saturated aqueous sodium chloride (25 mL) then diluted with 2-methyltetrahydrofuran (MeTHF; 50 mL). We separated the phases and washed the organic layer again with saturated aqueous ammonium chloride (25 mL) and saturated aqueous sodium chloride (25 mL). The organic layer was then dried over sodium sulfate, filtered, and concentrated in vacuo to provide the title compound, which was carried over to the next step assuming the quantitative yield.

Step 3: 7-Bromo-1H-indole-6-carbonitrile

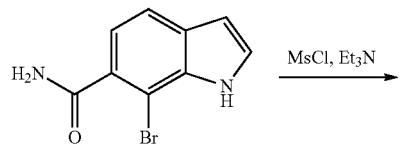

We added Et₃N (triethylamine; 44.1 mL, 315 mmol) to a suspension of 7-bromo-1H-indole-6-carboxamide (7.53 g, 31.5 mmol) in DCM (315 mL) at 0° C. and stirred the resulting orange solution at that temperature until we obtained a homogeneous solution. MsCl (12.2 mL, 157 mmol) was then added dropwise, and the solution was stirred at 0° C. for 5 minutes. We diluted the mixture with ethyl acetate and washed it with saturated aqueous sodium bicarbonate before extracting the aqueous layer twice more with ethyl acetate. The organic layers were combined, washed with brine, dried over sodium sulfate, filtered, and concentrated in vacuo. The residue was purified by filtering it through a pad of silica (eluting with ethyl acetate) to provide the title compound as a brown solid (5.80 g, 26.24 mmol, 83% yield).

Step 4: 7-Bromo-3-(2-chloro-5-(trifluoromethyl)pyrimidin-4-yl)-1H-indole-6-carbonitrile

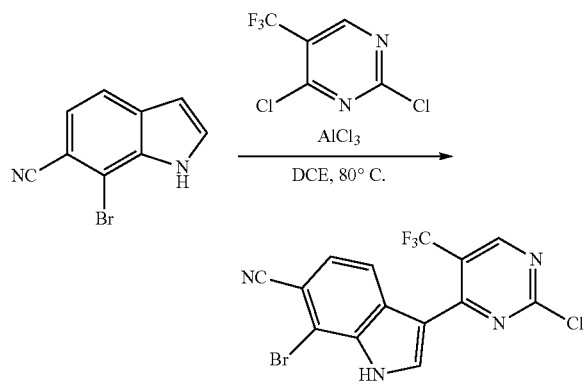

We added AlCl₃ (1.83 g, 13.6 mmol) to a solution of 2,4-dichloro-5-trifluoromethylpyrimidine (3.66 mL, 27.2 mmol) in 1,2-dichloroethane (DCE; 36.2 mL) and stirred the resulting 1,2-suspension at 80° C. for 30 minutes. We added 7-bromo-1H-indole-6-carbonitrile (2.00 g, 9.05 mmol) to the mixture and stirred the resulting red solution at 80° C. until full conversion (4 hours). The reaction mixture was then diluted with MeTHF (100 mL) and washed with water (100 mL). The aqueous layer was extracted with 2-MeTHF (100 mL), and the organic extracts were combined, dried over sodium sulfate, filtered, and concentrated in vacuo. Formation of two possible regioisomers was observed in a ratio of 3:1 (desired/undesired). We purified the residue by reverse phase chromatography on C18 (MeCN (acetonitrile) in water, 15 to 80% gradient) to provide the title compound as a beige solid (1.51 g, 3.76 mmol, 42% yield). ¹H NMR (500 MHz, DMSO) δ 13.00 (brs, 1H), 9.17 (s, 1H), 8.35 (d, J=8.4 Hz, 1H), 8.16 (d, J=2.6 Hz, 1H), 7.71 (d, J=8.4 Hz, 1H).

Step 5: (S)-7-Bromo-3-2-((6,6dimethylpiperidin-3-yl)amino-3-(trifluoromethyl)pyrimidin-4-yl)-1H-indole-6-carbonitrile

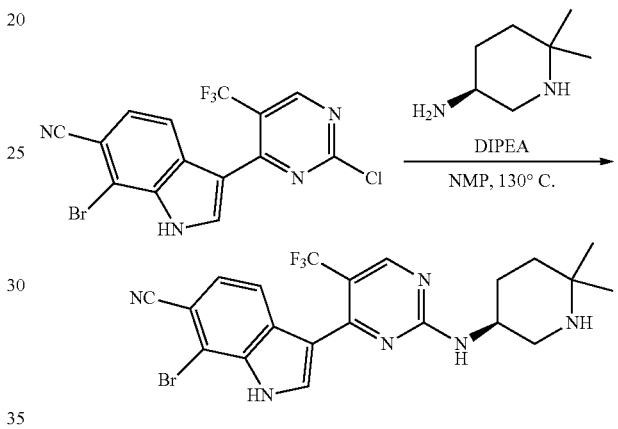

We dissolved 7-bromo-3-(2-chloro-5-(trifluoromethyl)pyrimidin-4-yl)-1H-indole-6-carbonitrile (200 mg, 0.498 mmol), (S)-6,6-dimethylpiperidin-3-amine (95.8 mg, 0.747 mmol), and DIPEA (074 µL, 0.996 mmol) in NMP (4 mL) then stirred the reaction mixture at 130° C. in an oil bath until full conversion (3 hours). The mixture was cooled to room temperature, loaded directly onto a C18 column and purified by reverse phase chromatography (MeCN with 0.1% FA (formic acid) in water also containing 0.1% FA, 0 to 100% gradient). The title compound was obtained as a beige solid (245 mg, 0.497 mmol, quantitative yield).

Step 6: (S)-7-(dimethylphosphoryl)-3-(2-((6,6dimethylpiperidin-3-yl)amino)-5-(trifluoromethyl)-pyrimidin-4-yl)-1H-indole-6-carbonitrile

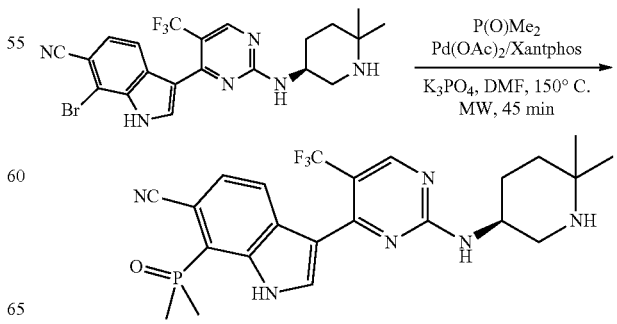

We combined (S)-7-bromo-3-(2-((6,6-dimethylpiperidin-"3-yl)amino)-5-(trifluoromethyl)-pyrimidin-4-yl)-1H-indole-6-carbonitrile (180.0 mg, 0.365 mmol) Xantphos (21.5 ng, 36.5 μmol), palladium (II) acetate (4.14 ng, 18.2 μmol), and $K_3PO_4$ (85.2 mg, 0.401 mmol) in a 2.5 mL microwave vial under nitrogen Dimethylphosphine oxide (73 mg, 0.912 mmol) was dissolved in anhydrous DMF (1 mL), and the solution was degassed before combining with the other reactants in a microwave vial. The sealed vial with the reaction mixture was then submitted to heat in a microwave reactor at 150° C. for 45 minutes. The reaction mixture was cooled to room temperature, loaded directly onto a C18 column, and purified by reverse phase chromatography (MeCN in aqueous 10 mM ammonium formate pH 3.8, 15 to 35% gradient). The title compound was obtained as an off-white solid (76 mg, 0.155 mmol, 42% yield).

Example 5: Synthesis of (3S)-1-benzyl-5,5-dimethyl-piperidin-3-amine

Step 1: Methyl (2S)-5-oxopyrrolidine-2-carboxylate

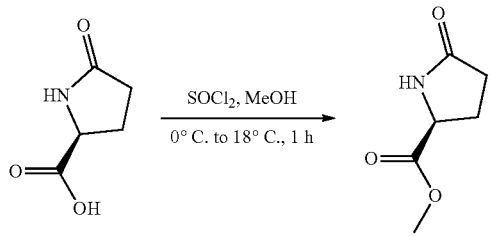

We added $SOCl_2$ (215.62 g, 1.81 mol, 131.47 mL, 2 eq) to a solution of (2S)-5-oxopyrrolidine-2-carboxylic acid (117 g, 906.18 mmol, 1 eq) in MeOH (500 mL) at 0° C. The mixture was stirred at 18° C. for 1 hour before the reaction mixture was concentrated. We diluted the residue with EtOAc (1000 mL) and TEA (triethylamine; 150 mL) and filtered the solid that was formed. The filtrate was evaporated to afford the title compound as a light yellow oil (147 g, crude) to be used directly in the next step without any further purification.

Step 2: (S)-1-tert-butyl 2-methyl 5-oxopyrrolidine-1,2-dicarboxylate

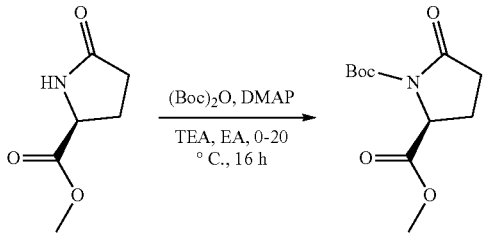

To a solution of methyl (2S)-5-oxopyrrolidine-2-carboxylate (147 g, 1.03 mol, 1 eq), DMAP (4-dimethylaminopyridine; 15.06 g, 123.24 mmol, 0.12 eq) and TEA (259.80 g, 2.57 mol, 357.35 mL, 2.5 eq) in EtOAc (500 mL) we added tert-butoxycarbonyl tert-butyl carbonate (291.37 g, 1.34 mol, 306.71 mL, 1.3 eq), dropwise, at 0° C. The mixture was then stirred at 20° C. for 16 hours. We then washed the reaction mixture with HCl (0.5 M, 1000 mL), saturated $NaHCO_3$ (1000 mL), brine (1500 mL), dried it over $Na_2SO_4$, and filtered and concentrated it under reduced pressure to give a residue that was then purified by re-crystallization from methyl tert-butyl ether (MTBE; 250 mL). The reaction mixture was filtered and evaporated to afford the title compound as a white solid (2 batches obtained; Batch 1: 108 g, 100% HPLC purity; Batch 2: 53 g, 90% $^1$H NMR purity).

Step 3: (S)-1-tert-butyl 2-methyl 4,4-dimethyl-5-oxopyrrolidine-1,2-dicarboxylate

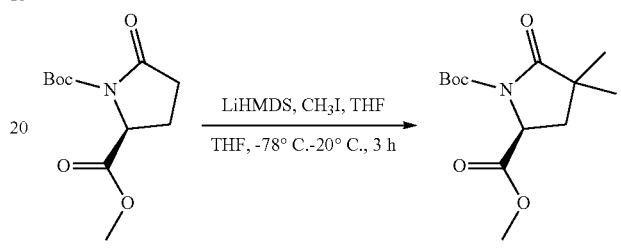

We added LiHMDS (lithium hexamethyldisilazide; 1 M, 172.66 mL, 2.1 eq), dropwise, to a solution of (S)-1-tert-butyl 2-methyl 5-oxopyrrolidine-1, 2-dicarboxylate (20 g, 82.22 mmol, 1 eq) in THF (500 mL) at −78° C. under $N_2$ atmosphere. After addition, the mixture was stirred at that temperature for 30 minutes before we added $CH_3I$ (35.01 g, 246.65 mmol, 15.36 mL, 3 eq), dropwise, at −78° C. under $N_2$ atmosphere. The resulting mixture was stirred at 20° C. for 2.5 hours. The reaction mixture was diluted with saturated aqueous $NH_4Cl$ (1000 mL) and extracted with EtOAc (300 mL×3). The combined organic layers were washed with brine (500 mL), dried over $Na_2SO_4$, filtered, and concentrated under reduced pressure to give a residue that was purified by MPLC ($SiO_2$, PE:EtOAc=4: 1-3:1) to afford the title compound as a light yellow solid (8 g, 25.95 mmol, 31.56% yield, 88% purity).

Step 4: tert-butyl N-[(1S)-4-hydroxy-1-(hydroxymethyl)-3,3-dimethyl-butyl]carbamate

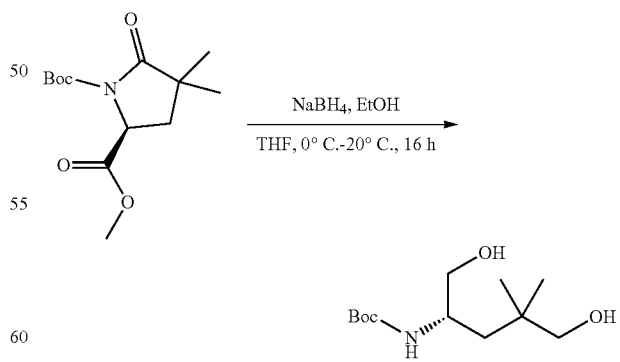

To a solution of (S)-1-tert-butyl 2-methyl 4, 4-dimethyl-5-oxopyrrolidine-1,2-dicarboxylate (4.3 g, 15.85 mmol, 1 eq) in THF (35 mL) we added $NaBH_4$ (1.80 g, 47.55 mmol, 3 eq), by portions, at 0° C. under $N_2$. After addition, EtOH (ethanol; 8.25 g, 179.09 mmol, 10.47 mL, 11.3 eq) was added dropwise at 0° C. The resulting mixture was stirred at 20° C. for 16 hours then poured into saturated aqueous NH₄Cl (250 mL) and extracted with EtOAc (100 mL×3). The combined organic layers were washed with brine (250 mL), dried over Na₂SO₄, filtered and concentrated under reduced pressure to afford the title compound as a colorless oil (3.67 g, crude), which was used directly in the next step without any further purification Step 5: [(2S)-2-(tert-butoxycarbonylamino)-4,4-dimethyl-5-methylsulfonyloxy-pentyl]methane-sulfonate

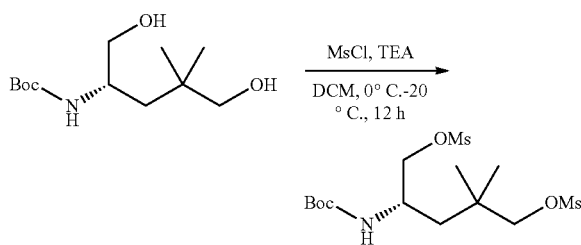

To a solution of tert-butyl N-[(1S)-4-hydroxy-1-(hydroxymethyl)-3,3-dimethyl-butyl]carbamate (3.67 g, 14.84 mmol, 1 eq) and TEA (6.01 g, 59.35 mmol, 8.26 mL, 4 eq) in EtOAc (25 mL) we added methanesulfonyl chloride (5.10 g, 44.52 mmol, 3.45 mL, 3 eq), dropwise, at 0° C. The resulting mixture was stirred at 20° C. for 12 hours then poured into H₂O (200 mL). EtOAc (50 mL×3) was used to extract the product. The organic layer was washed with brine (30 mL), dried over Na₂SO₄, filtered and evaporated to afford the title compound as a colorless oil (6.06 g crude) that was used directly in the next step without any further purification.

Step 6: Tert-butyl N-[(3S)-1-benzyl-5,5-dimethyl-3-piperidyl] carbamate

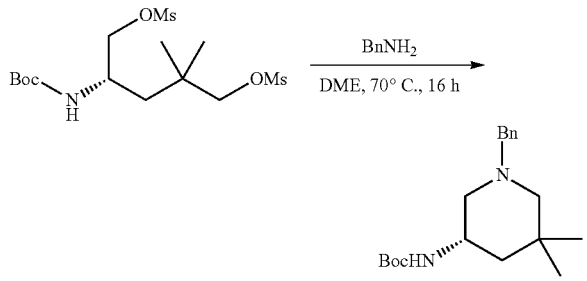

A flask was fitted with [(2S)-2-(tert-butoxycarbonylamino)-4, 4-dimethyl-5-methyl-sulfonyloxypentyl] methanesulfonate (6.06 g, 15.02 mmol, 1 eq), phenylmethanamine (5.15 g, 48.06 mmol, 5.24 mL, 3.2 eq) and dimethoxyethane (DME; 50 mL). We heated the reaction mixture to 70° C. for 16 hours then poured it into H₂O (40 mL). DCM (40 mL×3) was used to extract the product. The organic layer was washed with brine (30 mL), dried over Na₂SO₄, filtered and evaporated to afford the crude product, which was purified twice by MPLC (SiO₂, PE:EtOAc=20: 1-10:1) to afford the title compound as a colorless oil (580 mg, 1.49 mmol, 9.91% yield, 81.7% purity).

Step 7: (3S)-1-benzyl-5,5-dimethyl-piperidin-3-amine

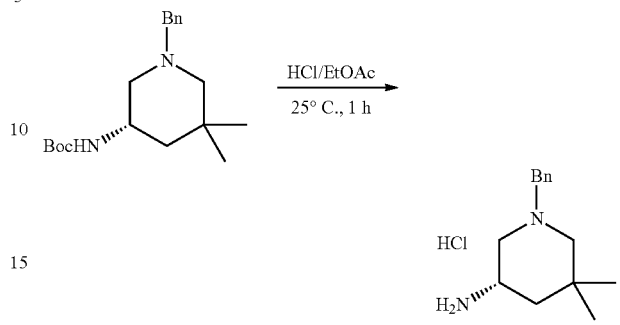

A flask was fitted with tert-butyl N-[(3S)-1-benzyl-5,5-dimethyl-3-piperidyl] carbamate (300 mg, 942.05 μmol, 1 eq) in HCl/EtOAc (15 mL). The mixture was stirred at 25° C. for 1 hour, after which some white precipitate formed. We filtered the mixture, and the cake was washed by EtOAc (5 mL), collected and dried over vacuum to afford the title compound as a white solid (220 mg, 738.23 μmol, 78.36% yield, 85.5% purity, HCl) as a white solid to be used directly in the next step.

Example 6: Synthesis of (S)-7-(dimethylphosphoryl)-3-(2-((5,5-dimethylpiperidin-3-yl)amino)-5-(trifluoromethyl)pyrimidin-4-yl)-1H-indole-6-carbonitrile (Compound 102)

Step 1: (S)-3-(2-((1-benzyl-5,5-dimethylpiperidin-3-yl)amino)-5-(trifluoromethyl)pyrimidin-4-yl)-7-bromo-1H-indole-6-carbonitrile

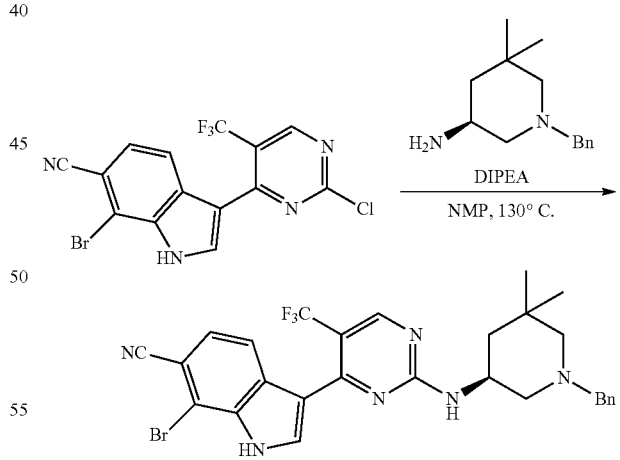

We dissolved 7-bromo-3-(2-chloro-5-(trifluoromethyl) pyrimidin-4-yl)-1H-indole-6-carbonitrile (168 mg, 0,418 mmol), (S)-1-benzyl-5,5-dimethylpiperidin-3-anine (128 ng, 0.585 mmol), and DIPEA (221 μL, 1.26 mmol) in NMP (2 mL). We stirred the reaction mixture at 130° C. in an oil bath until full conversion (4 hours). The mixture was cooled to room temperature, diluted with EtOAc and washed with saturated aqueous LiCl. The organic layer was separated, dried over sodium sulfate, filtered, and concentrated in vacuo to provide the crude title compound (240 ng, 0.41 mmol, quant. yield), which was used in the next step without further purification.

Step 2: (S)-3-(2-((1-benzyl-5,5-dimethylpiperidin-3-yl)amino)-5-(trifluoromethyl)pyrimidin-4-yl)-7-(dimethylphosphoryl)-1H-indole-6-carbonitrile

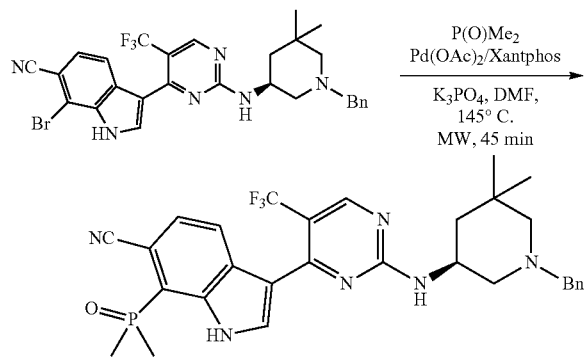

We combined (S)-3-(2-((1-benzyl-5,5-dimethylpiperidin-3-yl)amino)-5-(trifluoro-methyl)pyrimidin-4-yl)-7-bromo-1H-indole-6-carbonitrile (240 mg, 0.411 mmol), Xantphos (24.3 mg, 41.1 μmol), palladium (II) acetate (4.6 mg, 20.6 μmol), and $K_3PO_4$ (96.0 mg, 0.452 mmol) in a 2.5 mL microwave vial under nitrogen. Dimethylphosphine oxide (39.2 mg, 0.494 mmol) was dissolved in anhydrous DMF (1 mL), and the solution was degassed before combining with the other reactants in a microwave vial. The sealed vial with the reaction mixture was then submitted to heat in a microwave reactor at 145° C. for 45 minutes. The reaction mixture was then cooled to room temperature, diluted with 2-MeTHF and washed with saturated aqueous $NaHCO_3$ and brine. The organic layer was separated, dried over sodium sulfate, filtered, and concentrated in vacuo before the residue was purified by reverse phase chromatography on C18 (MeCN in aqueous 10 mM ammonium formate pH 3.8, 0 to 100% gradient). The title compound was obtained as a pale brown oil (58.0 mg, 0.10 mi ol, 24% yield).

Step 3: (S)-7-(dimethylphosphoryl)-3-(2-((5,5-dimethylpiperidin-3-yl)amino)-5-(trifluoromethyl)pyrimidin-4-yl)-1H-indole-6-carbonitrile

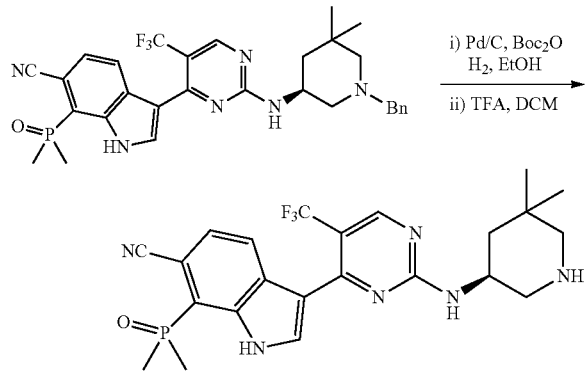

Under a nitrogen atmosphere, to a stirring solution of (S)-3-(2-((1-benzyl-5,5-dimethylpiperidin-3-yl)amino)-5-(trifluoromethyl)pyrimidin-4-yl)-7-(dimethylphosphoryl)-1H-indole-6-carbonitrile (58.0 mg, 0.10 mmol) in EtOH (12.5 mL), we added Pd/C 10% w/w (1.1 mg, 0.01 mmol) and $Boc_2O$ (di-t-butyl decarbonate; 65.5 mg, 0.30 mmol). The reaction mixture was evacuated and back-filled with nitrogen (×3) before being filled with hydrogen. The reaction mixture was then stirred at room temperature overnight under hydrogen atmosphere. After 16 hours, we observed an incomplete conversion and therefore filtered the reaction mixture through a pad of CELITE® and concentrated it under reduced pressure. The reaction was then repeated with the residue as described above. After almost complete consumption of starting material (48 hours), the reaction mixture was filtered through a pad of CELITE® and concentrated in vacuo to provide the crude product, which was engaged in the next step. Thus, the obtained oil was redissolved in DCM (5 mL), and TFA (0.23 mL, 3.0 mmol) was added. The reaction mixture was stirred at room temperature overnight. The mixture was then concentrated in vacuo, and the residue was purified by reverse phase chromatography on C18 (MeCN in aqueous 10 mM ammonium formate pH 3.8, 0 to 100% gradient) to provide the title compound as a white solid (11.11 mg, 0.023 mmol, 23% yield over two steps).

Example 7: Inhibition of CDK Kinase Activity

We assayed some compounds for inhibition of CDK7, CDK9, CDK12, and CDK2 activity at Biortus Biosciences (Jiangyin, Jiangsu Province, P.R. of China) using kinase assays for each CDK developed with a Caliper/LabChip EZ Reader (Perkin Elmer, Waltham, MA). These assays measure the amount of phosphorylated peptide substrate produced as a fraction of the total peptide following an incubation period at 27° C. with the following components: test compounds (variable concentrations from 10 μM down to 0.508 nM in a series of 3-fold serial dilutions), active CDK protein (with the indicated cyclin, listed below for each CDK), ATP (at either the $K_m$ concentrations listed below for each CDK/cyclin or 2 mM ATP), and substrate peptide (listed below) in the following buffer: 2-(N-morpholino)ethanesulfonate (MES buffer, 20 mM), pH 6.75, 0.01% (v/v) Tween 20 detergent, 0.05 mg/mL bovine serum albumin (BSA), and 2% DMSO.

Specifically, the CDK7 inhibition assay used CDK7/Cyclin H/MAT1 complex (6 nM) and "5-FAM-CDK7tide" peptide substrate (2 ™, synthesized fluorophore-labeled peptide with the sequence 5-FAM-YSPTSPSYSPTSPSYS-PTSPSKKKK (SEQ ID NO:1), where "5-FAM" is 5-carboxyfluorescein) with 6 mM $MgCl_2$ in the buffer composition listed above where the apparent ATP $K_m$ for CDK7/Cyclin H/MAT1 under these conditions is 50 μM. The CDK9 inhibition assay used CDK9/Cyclin T1 complex (8 nM) and "5-FAM-CDK9tide" peptide substrate (2 μM, synthesized fluorophore-labeled peptide with the sequence: 5-FAM-GSRTPMY-$NH_2$ (SEQ ID NO:2), where 5-FAM is defined above and $NH_2$ signifies a C-terminal amide with 10 mM $MgCl_2$ in the buffer composition listed above. The CDK12 inhibition assay used CDK12 (aa686-1082)/Cyclin K complex (50 nM) and "5-FAM-CDK9tide" (2 μM) as defined above, with 2 mM $MgCl_2$ in the buffer composition above. The CDK2 inhibition assay used CDK2/Cyclin E1 complex (0.5 nM) and "5-FAM-CDK7tide" (2 μM) as defined above, with 2 mM $MgCl_2$ in the buffer composition listed above.

The incubation period at 27° C. for each CDK inhibition assay was chosen such that the fraction of phosphorylated peptide product produced in each assay, relative to the total peptide concentration, was approximately 20% (±5%) for the uninhibited kinase (35 minutes for CDK7, 35 minutes for CDK2, 3 hours for CDK12, and 15 minutes for CDK9). In cases where the compound titrations were tested and resulted in inhibition of peptide product formation, these data were fit to produce best-fit $IC_{50}$ values. The best-fit $IC_{50}$ values at $K_m$ ATP for each CDK/Cyclin, except for CDK7/Cyclin H/MAT1, were used to calculate $K_i$ values, or the apparent affinity of each inhibitor for each CDK/Cyclin from the kinase activity inhibition assay, according to the Cheng-Prusoff relationship for ATP substrate-competitive inhibition (Cheng and Prusoff, *Biochem. Pharmacol.*, 22(23)3099-3108, 1973), with a correction term for inhibitor depletion due to the enzyme concentration (Copeland, "Evaluation of Enzyme Inhibitors in Drug Disclover: A Guide for Medicinal Chemists and Pharmacologists," Second Edition, March, 2013; ISBN: 978-1-118-48813-3):

$$IC_{50} = K_i\left(1 + \frac{[\text{Substrate}]}{K_m}\right) + \frac{[\text{Enzyme}]}{2}$$

Due to tight-binding inhibition and the limits of the CDK7/Cyclin H/MAT1 assay, instead of calculating the apparent $K_i$ values for each inhibitor, the $K_d$, or direct compound binding affinity, was measured using surface plasmon resonance (SPR) as described below.

Example 8: CDK7/Cyclin H Surface Plasmon Resonance (SPR) Assay Method

We measured binding kinetics and affinities of selected compounds to the CDK7/Cyclin H dimer using a Biacore T200 surface plasmon resonance (SPR) instrument (GE Healthcare). The dimer was amine-coupled to a CM5 sensor chip at pH 6.5 in 10 mM MES buffer at a concentration of 12.5 µg/mL with a flow rate of 10 µL/min. Target protein was immobilized on two flow cells for 12-16 seconds to achieve immobilized protein levels of 200-400 Response Units.

Compounds were titrated from 0.08-20 nM in a 9-step, 2-fold serial dilution in 10 mM HEPES buffer at pH 7.5 with 150 mM NaCl, 0.05% Surfactant P20, and 0.0002% DMSO. Each compound concentration cycle was run at 100 µL/min with 70 second contact time, 300 second dissociation time, 60 second regeneration time with 10 mM glycine pH 9.5, and 400 second stabilization time. For each compound, 0 nM compound controls and reference flow-cell binding were subtracted to remove background and normalize data. Compound titrations were globally fit by Biacore T200 Evaluation Software (GE Healthcare) using kinetics mode. Best-fit values for compound binding on-rate ($k_{on}$) and dissociation off-rate ($k_{off}$) for CDK7/Cyclin H were determined and these values were used to calculate the compound affinity ($K_d$) for CDK7/Cyclin H using the following equation:

$$K_d(M) = \frac{k_{off}(s^{-1})}{k_{on}(M^{-1}s^{-1})}$$

Compound selectivity for CDK7 over CDK2, CDK9, or CDK12 was determined based on the ratios of $K_i$ values for the off-target CDKs relative to the direct compound binding $K_d$ for CDK7 measured by SPR according to:

$$\text{Selectivity} = \frac{K_{i,\text{off target}}}{K_{d,CDK7}}$$

The inhibitory and dissociation constants and selectivity of the indicated compounds (three compounds of the invention and four comparators) against CDK2, CDK7, CDK9, and CDK12 are shown in the table of FIG. 1. As can be seen, each of the compounds of the invention is at least 1300-fold and up to 40,000-fold more specific for CDK7 than for the other CDKs tested.

Example 9: Inhibition of Cell Proliferation (Compounds 100-102)

The HCC70 cell line was derived from human TNBC, and we tested representative compounds of the invention, at different concentrations (from 4 µM to 126.4 µM; 0.5 log serial dilutions), for their ability to inhibit the proliferation of those cells. More specifically, we tested the same compounds tested above for CDK7 selectivity (the structures of which are shown in FIG. 1), and we used the known CDK inhibitors dinaciclib (or N-((1S,3R)-3-((5-chloro-4-(1H-indol-3-yl) pyrimidin-2-yl)amino)cyclohexyl)-5-((E)-4-(dimethylamino)but-2-enamido)picolinamide) and triptolide as positive controls. The cells were grown in ATCC-formulated RPMI-1640 medium (ATCC 30-2001) supplemented with 10% fetal bovine serum (FBS), at 37° C. in a humidified chamber in the presence of 5% $CO_2$. We conducted proliferation assays over a 72-hour time period using a CyQUANT® Direct Cell Proliferation Assay (Life Technologies, Chicago, IL USA) according to the manufacturer's directions and utilizing the reagents supplied with the kit. The results of the assay are shown in the Table below.

| Compound | HCC70 $EC_{50}$ (nM) |
| --- | --- |
| Compound 100 | 0.98 |
| Compound 101 | 5.6 |
| Compound 102 | 2.1 |
| Comparator 1 | 0.53 |
| Comparator 2 | 260 |
| Comparator 3 | 24 |
| Comparator 4 | 110 |

Example 10: Tumor Growth Inhibition in Patient-Derived Xenograft (PDX) Models Tumor growth inhibition was evaluated in estrogen receptor-positive breast cancer (ER+BC) PDX models selected in vivo for resistance to the CDK4/6 inhibitor palbociclib (ST1799, n=1) or resistance to both palbociclib and fulvestrant (ST941, n=1). Dosing was initiated when tumors were 100-200 mm³. Mice were treated with either Compound 101, QD (6 mg/kg, once daily, by mouth); fulvestrant, SC (2.5 mg/kg, once weekly dosing, by subcutaneous injection); palbociclib, QD (50 mpk, once daily, by mouth) or in combination of Compound 101 (6 mg/kg, once daily, by mouth) and fulvestrant (2.5 mg/kg, once weekly, by subcutaneous injection) over the course of 28 days, followed by 21 days of observation. Tumor growth inhibition (TGI) was calculated on the last day of dosing using the formula: $TGI=(V_{c1}-V_{t1})/(V_{c0}-V_{t0})$, where $V_{c1}$ and $V_{t1}$ are the mean volumes of control and treated groups at the time of tumor extraction, while $V_{c0}$ and $V_{t0}$ are the same groups at the start of dosing.

In the palbociclib-resistant ER+BC PDX (ST1799) model, the combination of Compound 101 and fulvestrant induced significant TGI (89%) with no evident tumor regrowth up to 21 days after dosing cessation, distinguishing the observed effects from Compound 101 (83%), fulvestrant (60%) or palbociclib (21%) when administered as single agents. Additionally, the combination of Compound 101 and fulvestrant was superior to the standard of care (SOC) combination of palbociblib and fulvestrant (75%). In a palbociclib and fulvestrant double-resistant ER+BC PDX model (ST941), Compound 101 administered as a single agent resulted in 33% TGI and fulvestrant and palbociclib as single agents or fulvestrant and palbociclib in combination had no activity. In contrast, the combination of Compound 101 and fulvestrant demonstrated significant TGI (68%; p<0.0001 vs fulvestrant as a single agent), suggesting re-sensitization to fulvestrant.

Figure 3:
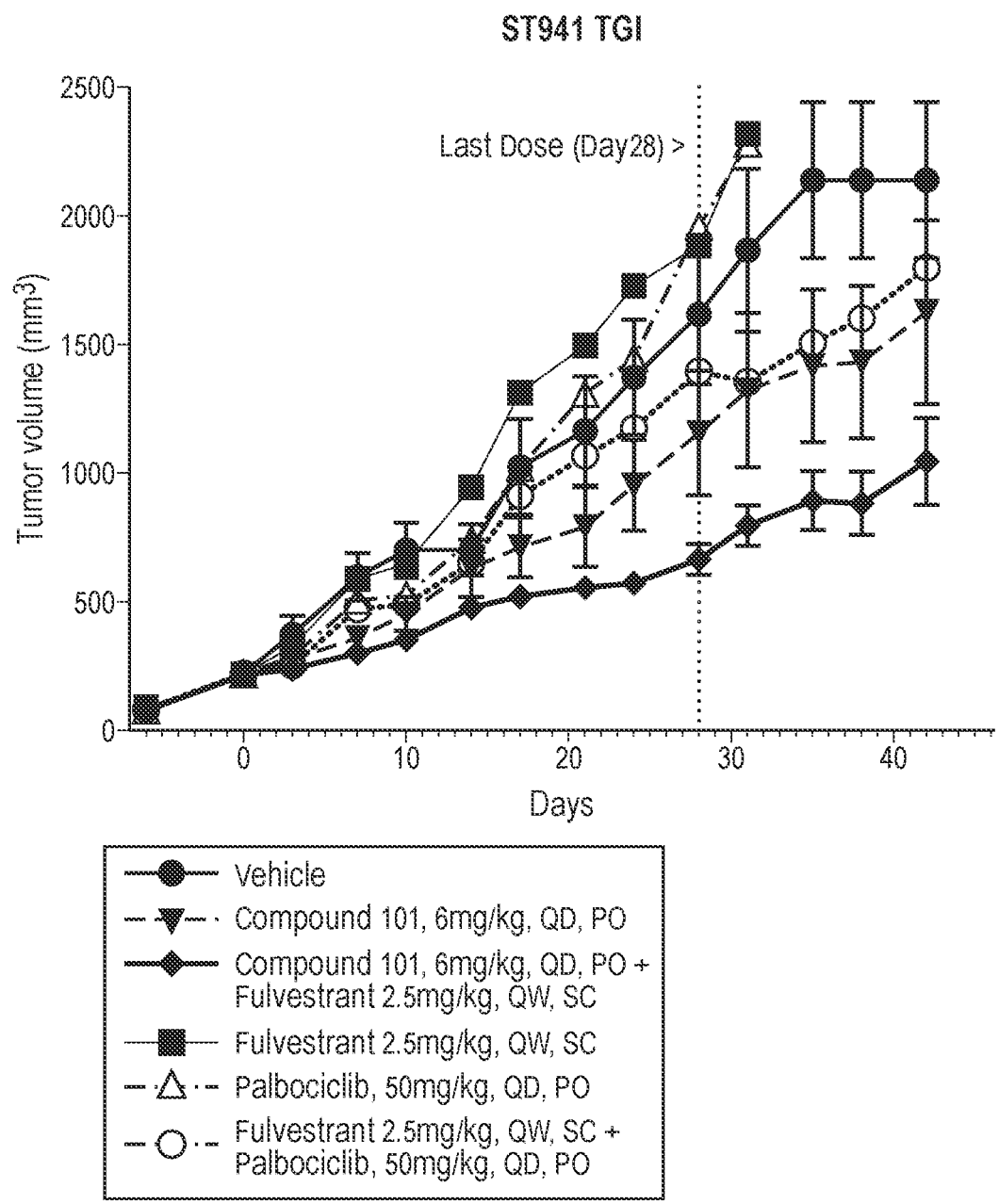
FIG. 3 is a line graph depicting changes in tumor volume (mm$^3$) over time (days) in the palbociclib- and fulvestrant-resistant HR+BC PDX model ST941 (as described further in the Examples below).
Figure 4:
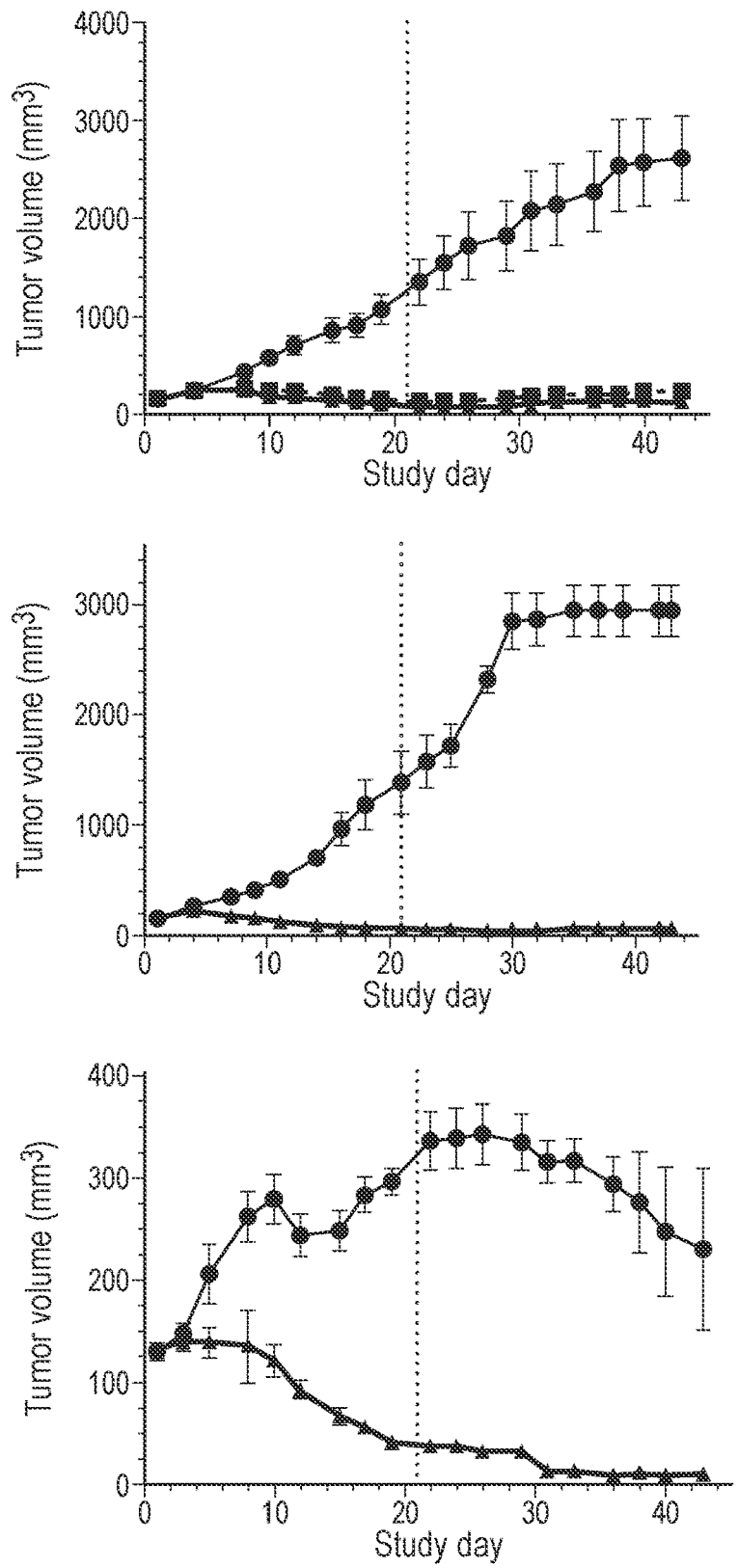
FIG. 4 is a panel showing three line graphs that depict changes in tumor volume (mm$^3$) over time (days) in PDX models of TNBC (BR5010; top), small cell lung cancer (LU5178; middle), and ovarian cancer (OV15398; bottom). The animals were treated with Compound 101 as described in Example 10. Data obtained from vehicle-treated (control) animals is represented by filled circles (upper traces in each graph). Data from animals modeling TNBC and given 10 mg/kg Compound 101 QD are represented in the top graph by filled squares; the dose of 5 mg/kg BID is represented by triangles. Triangles also represent data obtained from the animal models of SCLC and ovarian cancer treated with Compound 101 in the middle and bottom graphs.

FIG. 2 illustrates the TGI results from the palbociclib resistant HR+BC PDX model ST1799, and FIG. 3 illustrates the TGI results from the palbociclib and fulvestrant resistant HR+BC PDX model ST941. We also observed TGI in four additional PDX models; BR5010 (modeling TNBC), LU5178 (modeling small cell lung cancer (SCLC)), OV15398 (modeling high grade serous ovarian cancer (HGSOC)), and ST390 (modeling pancreatic ductal adenocarcinoma (PDAC)). In the TNBC model, Compound 101 was orally administered to tumor-bearing NOD/SCID mice at 10 mg/kg QD or 5 mg/kg BID for 21 days. In the SCLC and HGSOC models, Compound 101 was orally administered to tumor-bearing NOD/SCID mice at 3 mg/kg BID for 21 days. In the PDAC model, Compound 101 was orally administered to tumor-bearing NOD/SCID mice at 6 mg/kg QD. In the TNBC, SCLC, and HGSOC models, tumor volume was measured during the treatment period and for an additional 21 days after treatment ceased. The % TGI observed at the end of treatment (day 21) was calculated as: 1−[(Mean TV Compound 101 @ EOT−Mean TV Compound 101 @ Day 0)/(Mean TV Veh @ EOT−Mean TV Veh @ Day 0)]×100. The % regression was calculated as: (Mean TV Compound 101 @ EOT)/(Mean TV Compound 101 @ Day 0)×100. The same calculations were used for end of study (day 42). The results are shown in FIG. 4. These results demonstrate deep and sustained TGI, including regressions, at well tolerated doses, in a variety of tumor types. Dose-dependent transcriptional responses in xenograft tissue were observed within 4 hours of dosing and were sustained for 24 hours. Similar TGI was seen when the same total dose was administered either QD or BID in the TNBC PDX model, suggesting that the effect was AUC or $C_{min}$ driven. Moreover, the TGI observed in SCLC (in the LU5178 PDX model) had not been observed in previous studies with a covalent CDK7 inhibitor (data not shown). Regarding the model of PDAC, we found Compound 101 induced 100% TGI over the time examined (~28 days) at a dose well below the MTD: at day 21, tumor volume was ~1,250 mm³ in vehicle-treated mice but only about 250 mm³ in Compound 1-treated mice (6 mg/kg QD, PO). While Compound 101 could achieve 100% TGI at sub-MTD doses in the tested PDAC PDX tumors, a covalent CDK7 inhibitor achieved only modest TGI at its MTD (40 mg/kg BIW, by IV administration, with evident body weight loss (8.4%) and necrosis at the injection site; data not shown).

One of ordinary skill in the art will recognize or be able to ascertain using no more than routine experimentation many equivalents to the specific embodiments described herein. The embodiments described in detail herein are not intended to limit the scope of the invention. One of ordinary skill in the art will appreciate that various changes and modifications to the embodiments described may be made without departing from the spirit or scope of the present invention, as defined in the following claims.

Example 11. In Vitro Studies of Compound 101 in Combination with Various Second Agents In the studies described here, cancer cell lines from HR+ breast cancers (lines T47D; PIK3CA p.H1047R, MCF7; PIK3CA p.E545K), SCLC, (NCI-H1048) and CRCs (lines RKO; BRAF p.V600E, SW480; KRAS p.G12V) were grown to 70% confluency in their media of preferences based on the manufacturer recommendations. In the SCLC cell line (NCI-H1048), Compound 101 was tested in combination with SOC chemotherapy agents gemcitabine (a DNA synthesis inhibitor) and carboplatin (a DNA damage agent). In a CRC cell line (RKO; BRAF p.V600E), Compound 101 was tested in combination with SOC chemotherapy agent oxaliplatin (a DNA damage agent). Additionally, in CRC, Compound 101 was tested in combination with the selective MAPK pathway inhibitor trametinib in two CRC cell lines harboring MAPK pathway alterations; RKO (BRAF p.V600E mutant) and SW480 (KRAS p.G12V mutant). Compound 101 was tested in combination with the SOC agent capecitabine (an antimetabolite) in HR+MCF-7 cells. In the HR+ cell lines MCF7 and T47D, which have activating mutations in the PIK3CA kinases, Compound 101 was tested in combination with the PIK3CA selective inhibitor alpelisib. On the day of assay, cells were lifted and counted using the Countess II FL (Life Technologies). Using an automated dispenser (here, Multidrop™ Combi Reagent Dispenser), 50 µL of preferred cell media containing 20,000-50,000 cells/ml was distributed into black 384-well Nunc plates (Thermo) and allowed to adhere overnight prior to compound addition. Compound arrays were distributed to 384 well assay plates using Synergy Plate Format with an HP D300e Digital Dispenser (HP). Compound 101 and other TEST agents were dissolved in DMSO to make a stock solution that allowed for more accurate dispensing. However, due to solubility and reactivity, platinum agents were dissolved in water with an addition of 0.03% Tween-20 to allow for dispensing with digital printer. Compounds were plated in each quadrant of a 384-well plate in quadruplicate. Each quadrant contained test wells with combination of SY-1365 and carboplatin or oxaliplatin (TEST/test agent) as well as single agent columns, and vehicle wells. Compound 101 was plated in across from left to right in a high to low concentration (8 columns), and the varying concentrations of carboplatin or oxaliplatin (TEST) plated in synergy wells from top to bottom (7 rows). Concentrations were selected to cover the full isobologram of activity based on activity of single agents. Single agents were plated in dose in two columns, with a third separate column of just DMSO/vehicle treated wells. A separate plate for each cell line was seeded to allow for determination of a "Time Zero"/"Day Zero" number of cells to parse the differential cytostatic vs cytotoxic effects. On the day compounds were added, viability of the time zero plate was determined to identify growth inhibition from cell killing effects. After addition of compound, cell plates were incubated for 5 days in a 37° C. incubator. Cell viability was evaluated using CellTiter-Glo®

2.0 (Promega) following manufacturer protocols. Data was analyzed in CalcuSyn utilizing the median effect principle of presented by Chou-Talalay and visualized using GraphPad Prism Software. Key parameters assessed were combination index and dose reduction index.

Figure 5:
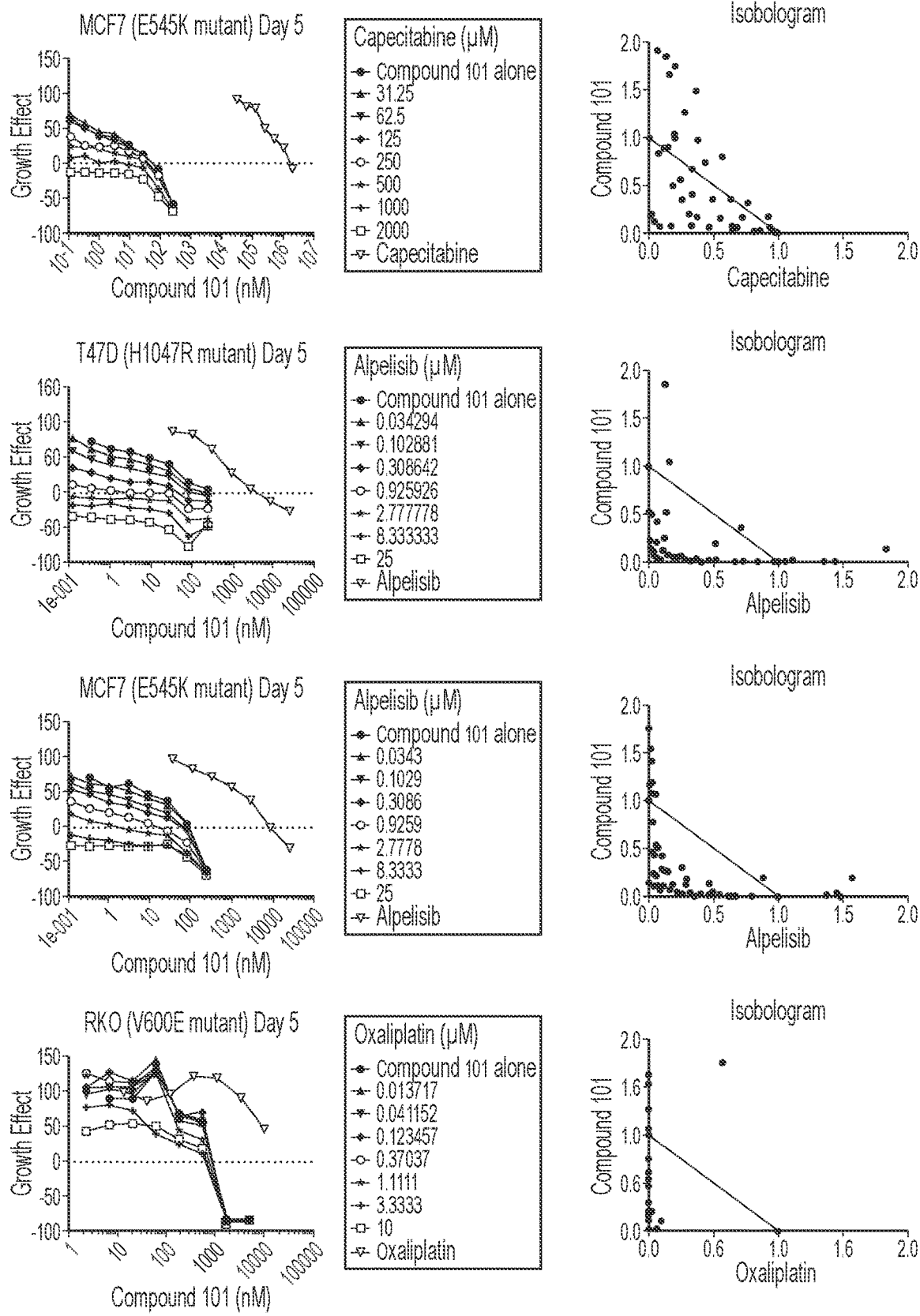
FIG. 5 is a panel of line graphs showing tumor growth in the PDX models indicated and the corresponding isobolograms, each generated as described in Example 11. Compound 101 was applied to cells in combination with the indicated second agents at the concentrations shown.

We found the combination of Compound 101 with SOC chemotherapy (gemcitabine or carboplatin in SCLC, oxaliplatin in CRC, or capecitabine in HR+ breast cancer) showed synergy and was superior to either agent alone. The combination of Compound 101 with the targeted agent trametinib, a selective MAPK pathway inhibitor approved for the treatment of BRAF p.V600E mutant melanoma and NSCLC, show significant synergy in BRAF p.V600E mutant CRC as well as in KRAS p.G12V mutant CRC, which harbors a different mutation within the MAPK pathway. The combination of Compound 101 with the targeted agent alpelisib, a selective PIK3CA inhibitor approved for the treatment of PIK3CA mutant HR+BC, showed significant synergy in both HR+ cell lines representing the two most common activating mutation of PIK3CA (p.E545K and p.H1047R). All synergy was determined using CalcuSyn utilizing the median effect principle of presented by Chou-Talalay and visualized using GraphPad Prism Software. Combination effect is reflected by shift in IC50 of Compound 101 with addition of carboplatin or oxaliplatin or increased antiproliferative effect with lower amounts of either single agent. This is visualized in the isobolograms of FIG. 5, where points below the diagonal line reflect synergy.

Example 12. Deep and Sustained Responses to Compound 101 in TNBC, HGSOC, and SCLC PDX Models We evaluated TGI in 12 different PDX models (Crown Biosciences) in various tumor indications with PDXs representing SCLC (n=5; LU5180, LU5178, LU5192, LU5173, LU5210), TNBC (n=4; BR5010, BR1458, BR5399, BR10014) and HGSOC (n=3; OV15398, OV5392, OV15631). Dosing was initiated when tumors were 150-300 mm$^3$. Mice were treated with either Compound 101, QD (6 or 10 mg/kg once daily, by mouth) or BID (3 or 5 mg/kg twice daily, by mouth) over the course of 21 days, followed by 21 days of observation. TGI was calculated on the last day of dosing using the formula: $TGI=(V_{c1}-V_{t1})/(V_{c0}-V_{t0})$, where $V_{c1}$ and $V_{t1}$ are the mean volumes of control and treated groups at the time of tumor extraction, while $V_{c0}$ and $V_{t0}$ are the same groups at the start of dosing.

To perform whole exome sequencing (WES), we isolated DNA from passage matched tumors using DNeasy® Blood and Tissue Kit via manufacturer protocol and sent it to Wuxi Aptec for WES using Agilent's SureSelectXT Human All Exon V6 kit. Samples were sequenced to a depth of ~300×. Reads were trimmed to remove adapter sequences via Skewer (v0.2.1). Reads were then mapped and further processed using Sentieon tools: BWA, DeDup, Realigner, and QualCal (v201808.03). Variants were called using Sentieon's Haplotyper tool, and initial annotations were performed using Ensembl's Variant Effect Predictor (VEP, release_96.2). FATIMM-MLK was also used to annotate variant effects. Variants that met the following qualifications were included in sample characterizations: (1) variant is located in a protein-coding gene; (2) variant affects protein sequence or results in a frameshift; (3) missense mutations are classified as damaging by SIFT, PolyPhen, or FATHMM-MLK (≥0.75); (4) variant allele frequency is ≥10%. Copy-number (CN) variation across capture regions were called using CNVkit (v0.9.1), and CNs for individual genes were calculated by using the mean CN across its capture regions. For model LU5210 mutation/CNV data was made available from WES data provided by the PDX vendor (Crown Biosciences Inc.).

Figure 6:
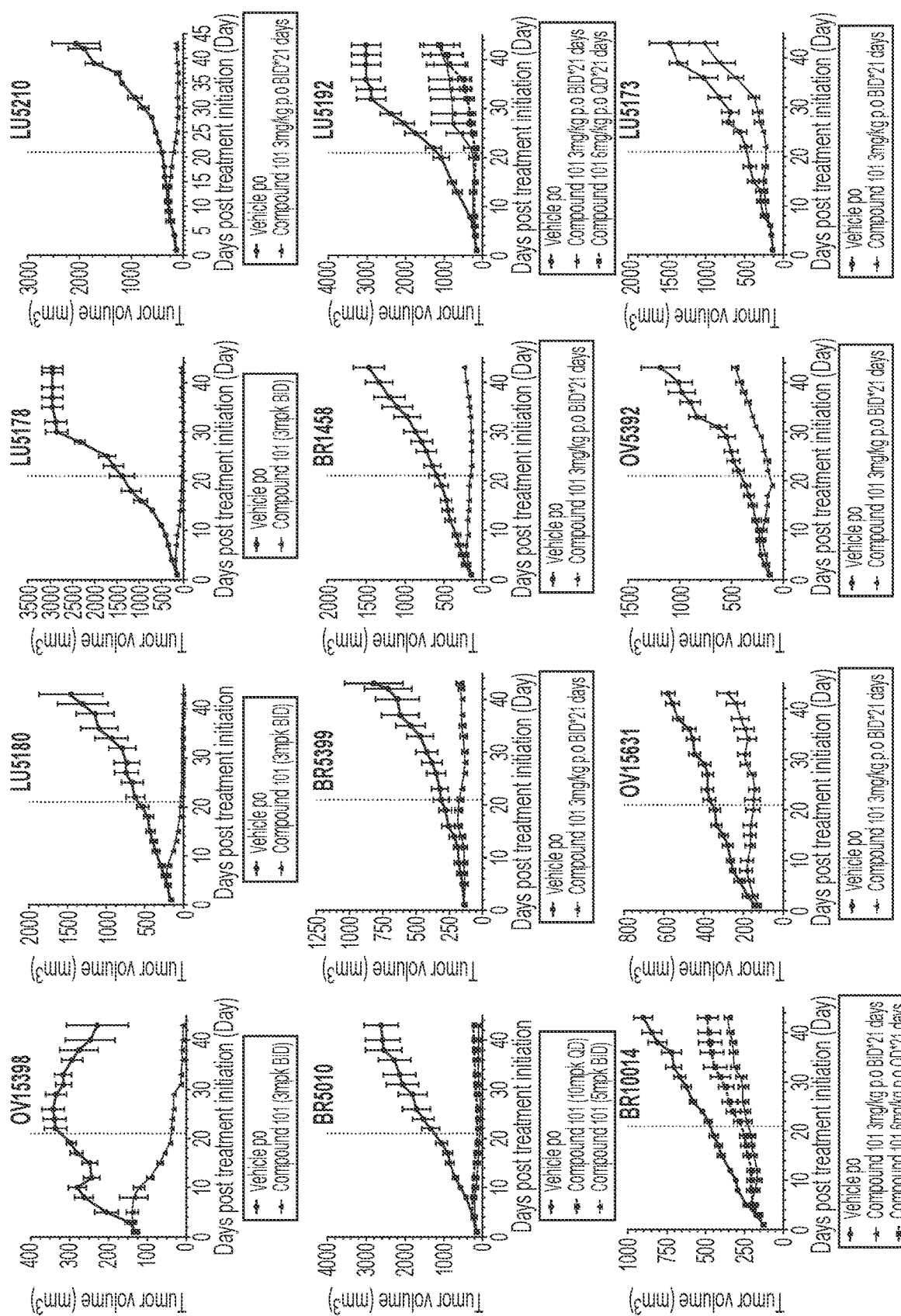
FIG. 6 is a panel of graphs generated from the data collected in the Compound 101-treated PDX models described in Example 12. Black lines with squares represent vehicle-treated animals. Gray lines represent Compound 101-treated animals. Error bars are SEM. BID=twice daily; CNV=copy number variation; MPK=mg per kg body weight; PO=oral; QD=once daily; RB=retinoblastoma; SCLC=small cell lung cancer; TNBC=triple negative breast cancer. The dotted line in the graph represents the last day of treatment.

At these doses, Compound 101 induced at least 50% TGI at the end of the 21-day dosing period in all models. In a subset of models (58%, 7/12), Compound 101 responses were deep (>95% TGI or regression) and sustained, with no evidence of tumor regrowth for 21 days after treatment discontinuation (see FIG. 6). Compound 101 was well tolerated, with no evident body weight loss at all once-daily doses tested, indicating that the MTD is above 10 mg/kg once daily in tumor-bearing mice. Deep and sustained responses were observed in each indication tested.

---

What is claimed is:

1. A compound of structural Formula (I):

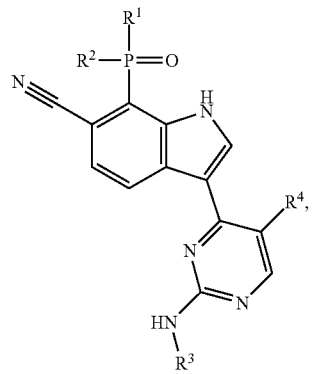
(I)

or a pharmaceutically acceptable salt thereof, wherein:
- $R^1$ is methyl or ethyl;
- $R^2$ is methyl or ethyl;
- $R^3$ is 5-methylpiperidin-3-yl, 5,5-dimethylpiperidin-3-yl, 6-methylpiperidin-3-yl, or 6,6-dimethylpiperidin-3-yl, wherein one or more hydrogen atoms in $R^3$ is optionally replaced by deuterium; and
- $R^4$ is —$CF_3$ or chloro.

2. The compound of claim 1 or the pharmaceutically acceptable salt thereof, wherein (i) $R^1$ is methyl and $R^2$ is methyl or (ii) $R^1$ is methyl and $R^2$ is ethyl.

3. The compound of claim 1 or the pharmaceutically acceptable salt thereof, wherein $R^4$ is —$CF_3$.

4. The compound of claim 1 or the pharmaceutically acceptable salt thereof, wherein $R^4$ is chloro.

5. The compound of claim 1 or the pharmaceutically acceptable salt thereof, wherein $R^3$ is 5-methylpiperidin-3-yl.

6. The compound of claim 1 or the pharmaceutically acceptable salt thereof, wherein $R^3$ is 5,5-dimethylpiperidin-3-yl.

7. The compound of claim 1 or the pharmaceutically acceptable salt thereof, wherein $R^3$ is 6-methylpiperidin-3-yl.

8. The compound of claim 1 or the pharmaceutically acceptable salt thereof, wherein $R^3$ is 6,6-dimethylpiperidin-3-yl.

9. The compound of claim 1, having structural Formula (Ia):

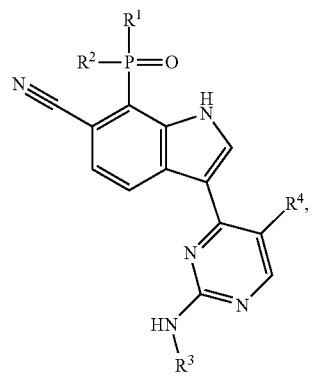
(Ia)

or the pharmaceutically acceptable salt thereof, wherein $R^3$ is

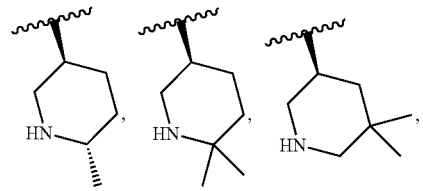

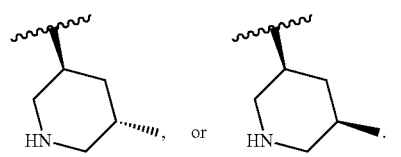

10. The compound of claim 9 or the pharmaceutically acceptable salt thereof, wherein (i) $R^1$ is methyl and $R^2$ is methyl or (ii) $R^1$ is methyl and $R^2$ is ethyl.

11. The compound of claim 9 or the pharmaceutically acceptable salt thereof, wherein $R^4$ is —$CF_3$.

12. The compound of claim 9 or the pharmaceutically acceptable salt thereof, wherein $R^4$ is chloro.

13. The compound of claim 9, wherein the compound is:

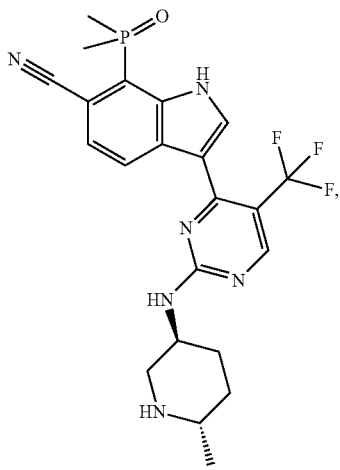

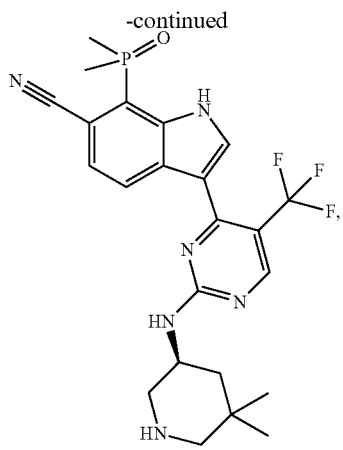

or is a pharmaceutically acceptable salt of any one of the foregoing compounds.

14. The compound of claim 1 or the pharmaceutically acceptable salt thereof, wherein one or more hydrogen atoms in $R^3$ is replaced with deuterium.

15. The compound of claim 1 or the pharmaceutically acceptable salt thereof, wherein none of the hydrogen atoms in $R^3$ are replaced with deuterium.

16. The compound of claim 1, wherein the compound is in the form of the pharmaceutically acceptable salt.

17. The compound of claim 16, wherein the pharmaceutically acceptable salt is an acid addition salt.

18. The compound of claim 4, wherein the acid addition salt is formed with lactic acid, hydrochloric acid, hydrobromic acid, phosphoric acid, sulfuric acid, perchloric acid, acetic acid, oxalic acid, maleic acid, tartaric acid, citric acid, succinic acid, or malonic acid.

19. A pharmaceutical composition comprising a therapeutically effective amount of the compound of claim 1, or the pharmaceutically acceptable salt thereof, and a pharmaceutically acceptable carrier.

20. The pharmaceutical composition of claim 19, wherein the composition is formulated for oral administration.

21. The pharmaceutical composition of claim 19, wherein the composition is formulated as an aqueous or non-aqueous solution or suspension.

22. The pharmaceutical composition of claim 19, wherein the composition is formulated as a tablet or capsule.

23. The pharmaceutical composition of claim 19, wherein the composition is formulated in unit dosage form.

24. The pharmaceutical composition of claim 19, wherein the pharmaceutically acceptable carrier comprises an inert diluent, a dispersing or granulating agent, a surface active agent or emulsifier, a disintegrating agent, a binding agent, a preservative, a buffering agent, or an emulsifier.

25. The pharmaceutical composition of claim 19, wherein the pharmaceutically acceptable carrier comprises a cellulose-based substance.

26. The pharmaceutical composition of claim 19, wherein the pharmaceutically acceptable carrier comprises lactose and/or corn starch.

27. The pharmaceutical composition of claim 19, wherein the pharmaceutically acceptable carrier is a sterile liquid.

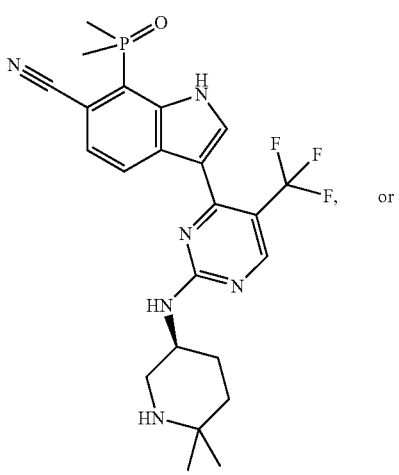 or

* * * * *

SEQUENCE LISTING

```
<160> NUMBER OF SEQ ID NOS: 2

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Ser Pro Thr Ser Pro Ser Tyr Ser Pro Thr Ser Pro Ser Tyr Ser
1               5                   10                  15

Pro Thr Ser Pro Ser Lys Lys Lys Lys
            20                  25

<210> SEQ ID NO 2
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Gly Ser Arg Thr Pro Met Tyr
1               5
```